US012571051B2

(12) United States Patent
Eccleston et al.

(10) Patent No.: US 12,571,051 B2
(45) Date of Patent: Mar. 10, 2026

(54) METHOD OF ISOLATING CIRCULATING NUCLEOSOMES

(71) Applicant: Belgian Volition SRL, Isnes (BE)

(72) Inventors: Mark Edward Eccleston, Isnes (BE); Jacob Vincent Micallef, London (GB)

(73) Assignee: Belgian Volition SRL, Isnes (BE)

( * ) Notice: Subject to any disclaimer, the term of this patent is extended or adjusted under 35 U.S.C. 154(b) by 960 days.

(21) Appl. No.: 17/638,136

(22) PCT Filed: Aug. 27, 2020

(86) PCT No.: PCT/EP2020/074026
§ 371 (c)(1),
(2) Date: Feb. 24, 2022

(87) PCT Pub. No.: WO2021/038010
PCT Pub. Date: Mar. 4, 2021

(65) Prior Publication Data
US 2022/0290252 A1      Sep. 15, 2022

(30) Foreign Application Priority Data

Aug. 27, 2019   (GB) ...................................... 1912251
Nov. 18, 2019   (GB) ...................................... 1916735
May 4, 2020   (GB) ...................................... 2006547

(51) Int. Cl.
*C12Q 1/6886*        (2018.01)
*C12Q 1/6806*        (2018.01)
(Continued)

(52) U.S. Cl.
CPC ..... *C12Q 1/6886* (2013.01); *G01N 33/57488* (2013.01); *C12Q 1/6806* (2013.01);
(Continued)

(58) Field of Classification Search
CPC .. C12Q 1/6886; C12Q 1/6806; C12Q 1/6851; C12Q 1/6804; C12Q 2600/154;
(Continued)

(56) References Cited

U.S. PATENT DOCUMENTS 9,222,937 B2 *   12/2015   Micallef ............ G01N 33/5308
2013/0230858 A1   9/2013   Cantor et al.
(Continued)

FOREIGN PATENT DOCUMENTS

WO    WO 2005/019826 A1    3/2005
WO    WO 2013/030577 A1    3/2013
(Continued)

OTHER PUBLICATIONS

Chakravarthy, The basic linker of macroH2A stabilizes DNA at the entry/exit site of the nucleosome, Nucleic Acids Research, Sep. 2012, 40, 8285-8295 (Year: 2012).*
(Continued)

*Primary Examiner* — Anne M. Gussow
*Assistant Examiner* — Allison E Schloop
(74) *Attorney, Agent, or Firm* — McDermott Will & Schulte LLP; Judy M. Mohr; Brennen P. Baylor

(57) ABSTRACT

The invention relates to methods for separating circulating cell free nucleosomes comprising linker DNA from a biological fluid sample, in particular nucleosomes of disease origin. Such methods allow for improved analysis of genetic and epigenetic markers associated with nucleosomes of disease origin.

12 Claims, 17 Drawing Sheets

Frequency

Tumor
145bp   Non-tumor
167bp 50      100      150      200      250

Circulating chromatin fragment
associated DNA length (bp)

(51) Int. Cl.
    *C12Q 1/6851*        (2018.01)
    *G01N 33/574*        (2006.01)
(52) U.S. Cl.
    CPC ..... *C12Q 1/6851* (2013.01); *C12Q 2600/154*
                    (2013.01); *C12Q 2600/156* (2013.01)
(58) Field of Classification Search
    CPC ........ C12Q 2600/156; C12Q 2563/131; C12Q
                    2565/531; G01N 33/57488; G01N
                    33/6875
    See application file for complete search history.

(56)                    References Cited

U.S. PATENT DOCUMENTS

2018/0024141 A1 *   1/2018   Micallef .............. G01N 27/622
                                                                435/6.14
    2019/0390253 A1    12/2019   Kennedy et al.

FOREIGN PATENT DOCUMENTS

WO        WO 2013/030578 A1     3/2013
    WO        WO 2013/030579 A1     3/2013
    WO        WO 2013/084002 A2     6/2013
    WO        WO-2017068371 A1 *    4/2017   .............. A61P 35/00

OTHER PUBLICATIONS

Nalabothula, The chromatin architectural proteins HMGD1 and H1 bind reciprocally and have opposite effects on chromatin structure and gene regulation, BMC Genomics, Feb. 2014, 15, 1-14 (Year: 2014).*
Yi and Kim, Histone tail cleavage as a novel epigenetic regulatory mechanism for gene expression, BMB Reports, May 2018, 51, 211-218 (Year: 2018).*
Bao et al., "Nucleosomes containing the histone variant H2A.Bbd organize only 118 base pairs of DNA", EMBO J., vol. 23, No. 16, pp. 3314-3324 (2004).
Bönisch et al., "H2A.Z.2.2 is an alternatively spliced histone H2A.Z variant that causes severe nucleosome destabilization", Nucleic Acids Res., vol. 40, No. 13, pp. 5951-5964 (2012).
Bowerman and Wereszczynski, "Effects of MacroH2A and H2A.Z on Nucleosome Dynamics as Elucidated by Molecular Dynamics Simulations", Biophys. J., vol. 110, No. 2, pp. 327-337 (2016).
Church et al., "Prospective evaluation of methylated SEPT9 in plasma for detection of asymptomatic colorectal cancer", Gut, vol. 63, No. 2, pp. 317-325 (2014).
Conde E Silva et al., "CENP-A-containing Nucleosomes: Easier Disassembly versus Exclusive Centromeric Localization", J. Mol. Biol., vol. 370, pp. 555-573 (2007).
Crowley et al., "Liquid biopsy: monitoring cancer-genetics in the blood", Nat. Rev. Clin. Oncol., vol. 10, No. 8, pp. 472-484 (2013).
Dai et al., "Detection of post-translational modifications on native intact nucleosomes by ELISA", J. Vis. Exp., Issue 50, No. e2593, 4 pages (2011).
Dhaenens et al., "Histone proteolysis: a proposal for categorization into 'clipping' and 'degradation'", Bioessays vol. 37, No. 1, pp. 70-79 (2014).
Dhasarathy and Wade, "The MBD protein family-reading an epigenetic mark?", Mutat. Res., vol. 647, No. 1-2, pp. 39-43 (2008).
Fong et al., "Comparison of 7 methods for extracting cell-free DNA from serum samples of colorectal cancer patients", Clin. Chem., vol. 55, No. 3, pp. 587-589 (2009).
Go et al., "Non-invasive aneuploidy detection using free fetal DNA and RNA in maternal plasma: recent progress and future possibilities", Human Reproductive Update, vol. 17, No. 3, pp. 372-382 (*Advanced Access Publication* 2010).
Guerrero-Preston et al., "Global DNA hypomethylation in liver cancer cases and controls: a phase I preclinical biomarker development study", Epigenetics, vol. 2, No. 4, pp. 223-226 (2007).

Holdenrieder et al., "nucleosomes in serum of patients with benign and malignant diseases", Int. J. Cancer (Pred. Oncol.), vol. 95, pp. 114-120 (2001).
Holdenrieder and Stieber, "Clinical use of circulating nucleosomes", Crit. Rev. Clin. Lab. Sci., vol. 46, No. 1, pp. 1-24 (2009).
Jung et al., "Cell-free DNA in the blood as a solid tumor biomarker—a critical appraisal of the literature", Clin. Chimica Acta., vol. 411, No. 21-22, pp. 1611-1624 (2010).
Marsman et al., "Extracellular histones, cell-free DNA, or nucleosomes: differences in immunostimulation", Cell Death and Disease, vol. 7, No. (12) Article # e2518, pp. 1-9 (2016).
Mouliere et al., "Enhanced detection of circulating tumor DNA by fragment size analysis", Sci. Transl. Med., vol. 10, No. 466, 1-28, doi:10.1126/scitranslmed.aat4921 (2018).
Nalabothula et al., "The chromatin architectural proteins HMGD1 and H1 bind reciprocally and have opposite effects on chromatin structure and gene regulation", BMC Genomics, vol. 15, No. 92, pp. 1-14, (2014).
Newman et al., "An ultrasensitive method for quantitating circulating tumor DNA with broad patient coverage", Nat. Med., vol. 20, No. 5, pp. 548-554 (2014).
Rasmussen et al., "Circulating cell-free nucleosomes as biomarkers for early detection of colorectal cancer", Oncotarget, vol. 9, No. 12, pp. 10247-10258 (2017).
Sakamoto et al., "Immunoprecipitation of nucleosomal DNA is a novel procedure to improve the sensitivity of serum screening for the p16 hypermethylation associated with colon cancer", Cancer Epidemiology, vol. 34, No. 2, pp. 194-199 (2010).
Salgame et al., "An ELISA for detection of apoptosis", Nucleic Acids Res., vol. 25, No. 3, pp. 680-681 (1997).
Schrader et al., "Characterization of Dnmt1 Binding and DNA Methylation on Nucleosomes and Nucleosomal Arrays", PLoS One, vol. 10, No. 10, Article # e0140076, pp. 1-22 (2015).
Schwarzenbach et al., "Cell-free nucleic acids as biomarkers in cancer patients", Nat. Rev. Cancer, Nov. 11, No. 6, pp. 426-437 (2011).
Sina et al., "Epigenetically reprogrammed methylation landscape drives the DNA self-assembly and serves as a universal cancer biomarker", Nat. Commun., vol. 9, No. 1, Article # 4915, pp. 1-13 (2018).
Snyder et al., "Cell-free DNA Comprises an In Vivo Nucleosome Footprint that Informs Its Tissues-Of-Origin", Cell, vol. 164, No. 1-2, pp. 57-68 (2016).
Soares et al., "Global DNA hypomethylation in breast carcinoma: correlation with prognostic factors and tumor progression", Cancer, vol. 85, No. 1, pp. 112-118 (1999).
Sultanov et al., "Unfolding of core nucleosomes by PARP-1 revealed by spFRET microscopy", AIMS Genetics, vol. 4, No. 1, pp. 21-31 (2017).
Underhill et al., "Fragment Length of Circulating Tumor DNA", PLOS Genet., vol. 12, No. 7, pp. 1-24, DOI:10.1371/journal.pgen. 1006162 (2016).
UniProt ID: O14646, "CHD1_Human", 11 pages (1998).
UniProt ID: P26358, "DNMT1_Human", 21 pages (1992).
UniProt ID: P09429, "HMGB1_Human", 23 pages (1989).
UniProt ID: P09874, "PARP1_Human", 29 pages (1989).
UniProt ID: Q9UIS9, "MBD1_Human", 15 pages (2004).
UniProt ID: Q9UBB5, "MBD2_Human", 8 pages (2000).
UniProt ID: O95983, "MBD3_Human", 9 pages (1999).
UniProt ID: O95243, "MBD4_Human", 8 pages (1991).
UniProt ID: P51608, "MECP2_Human", 23 pages (1996).
Van Nieuwenhuijze et al., "Time between onset of apoptosis and release of nucleosomes from apoptotic cells: putative implications for systemic lupus erythematosus", Ann. Rheum. Dis., vol. 62, No. 1, pp. 10-14 (2003).
Wiesler and Weinzierl, "Robotic high-throughput purification of affinity-tagged recombinant proteins", Methods Mol. Biol., vol. 1286, pp. 97-106 (2015).
Yang et al., "H2A.Z regulates tumorigenesis, metastasis and sensitivity to cisplatin in intrahepatic cholangiocarcinoma", Int. J. Oncol., vol. 52, No. 4, pp. 1235-1245 (2018).

(56) References Cited

OTHER PUBLICATIONS

Yi and Kim, "Histone tail cleavage as a novel epigenetic regulatory mechanism for gene expression", BMB Reports, vol. 51, No. 5, pp. 211-218 (2018).

Zhou et al., "Circulating cell-free nucleic acids: promising biomarkers of hepatocellular carcinoma", Semin. Oncol., vol. 39, No. 4, pp. 440-448 (2012).

* cited by examiner

Frequency

A. Immunoassay for nucleosomes
using antibody pair 1 and pair 2

B. Immunoassay for nucleosomes
containing clipped histone H3

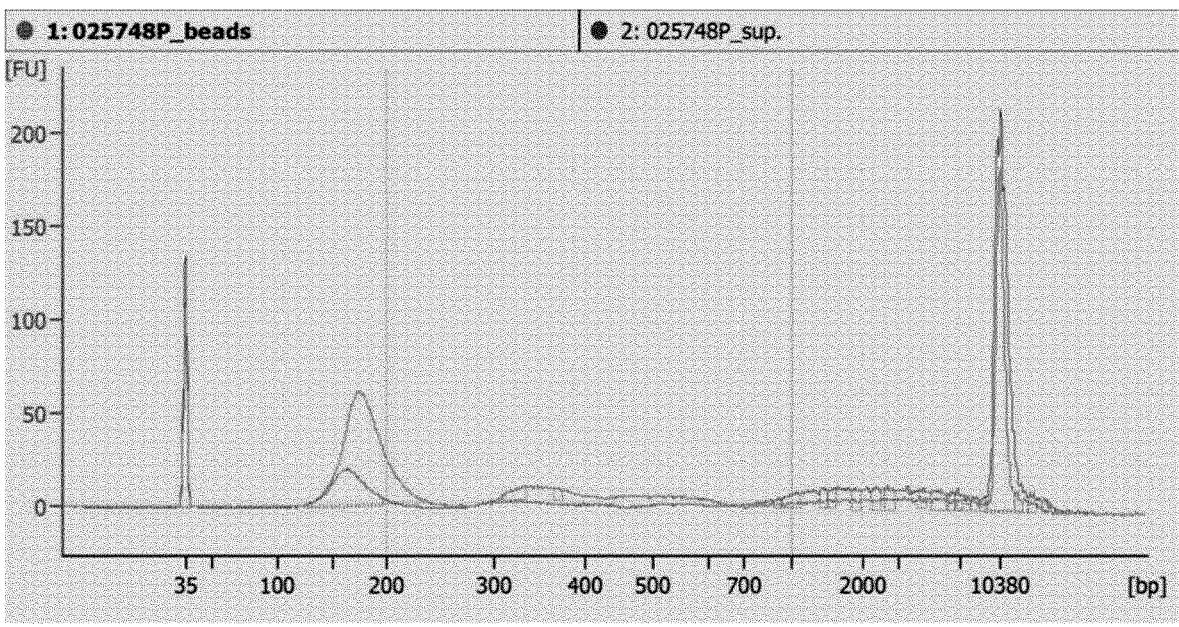
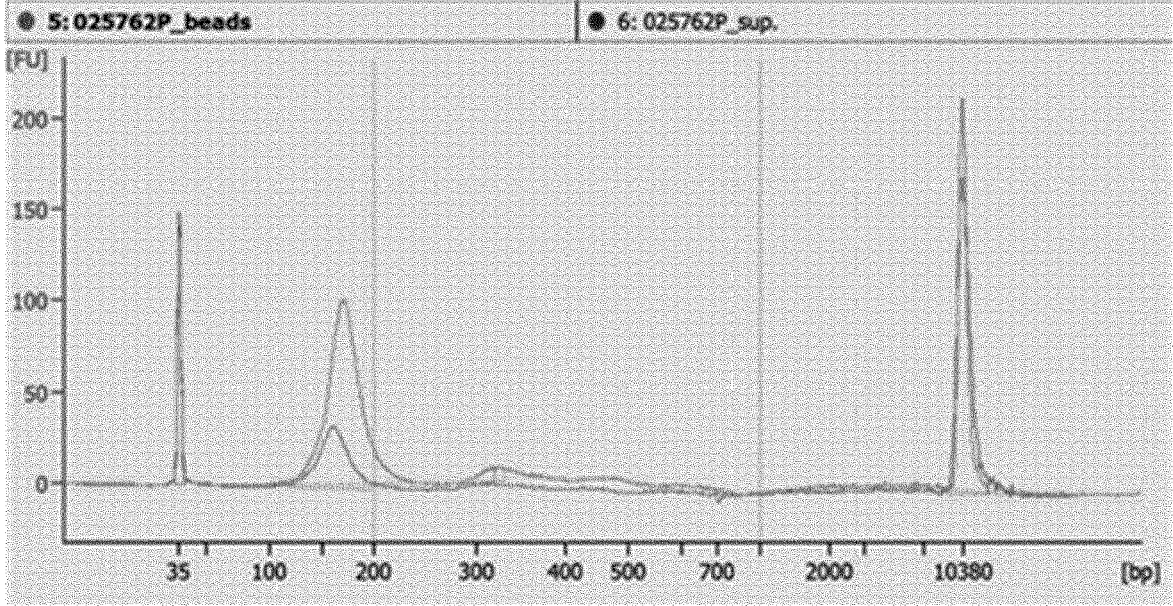
FIGURE 13 (contd.)

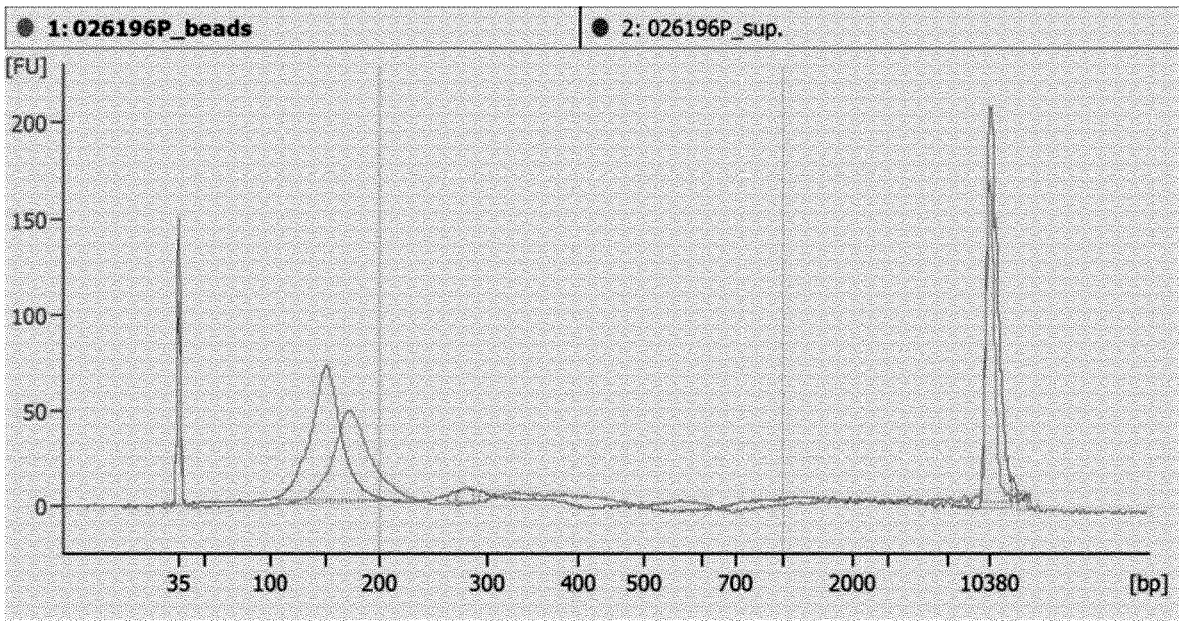
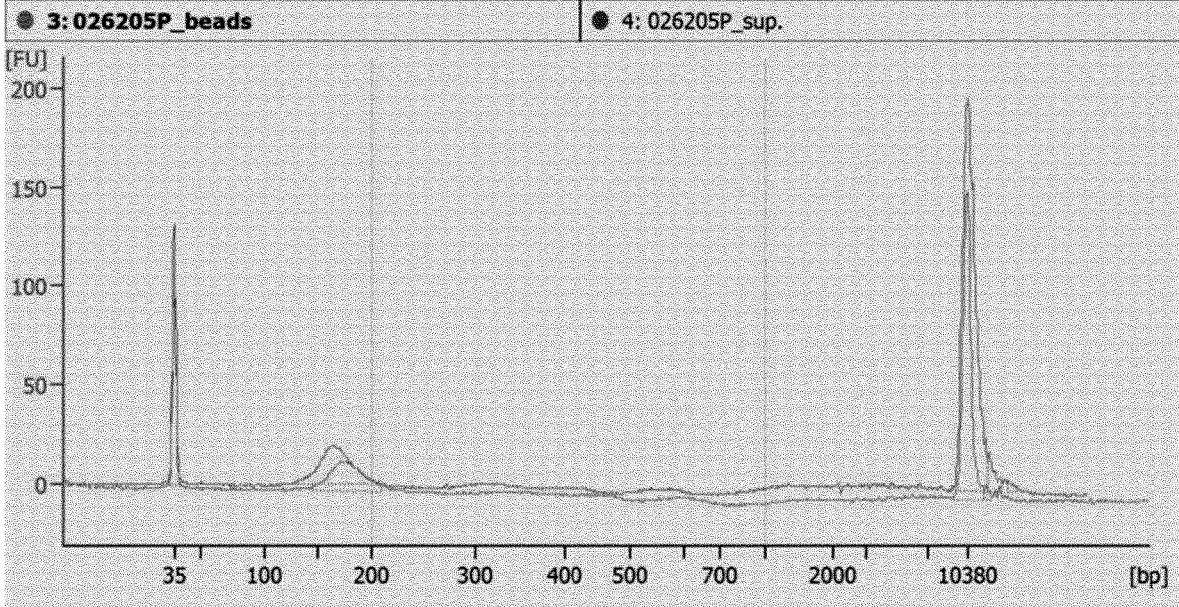
FIGURE 13 (contd.)

METHOD OF ISOLATING CIRCULATING NUCLEOSOMES

CROSS-REFERENCE TO RELATED APPLICATIONS

This application is a U.S. National Stage Application under 35 U.S.C. § 371 which claims the benefit of priority to International Patent Application No. PCT/EP2020/074026, filed Aug. 27, 2020, which claims the benefit of priority to GB Patent Application No. 2006547.0, filed May 4, 2020, GB Patent Application No. 1916735.2, filed Nov. 18, 2019, and GB Patent Application No. 1912251.4, filed Aug. 27, 2019, each of which is hereby incorporated by reference in its entirety.

FIELD OF THE INVENTION

The invention relates to methods of enriching and isolating circulating, cell free nucleosomes, in particular nucleosomes of disease origin. Such methods allow for improved analysis of genetic and epigenetic markers associated with nucleosomes of disease origin.

BACKGROUND OF THE INVENTION

Cellular DNA exists as a protein-nucleic acid complex called chromatin. The nucleosome is the basic unit of chromatin structure and consists of DNA wound around a protein complex. The DNA is wound around consecutive nucleosomes in a structure often said to resemble "beads on a string" and this forms the basic structure of open or euchromatin. In compacted or heterochromatin this string is coiled and super coiled in a closed and complex structure.

Each nucleosome in chromatin consists of a protein complex of eight highly conserved core histones (comprising of a pair of each of the histones H2A, H2B, H3, and H4). Around this complex are wrapped approximately 145 base pairs (bp) of DNA. Another histone, H1, which may be located on the nucleosome outside of the core histones, binds a further 20 bp of DNA to produce nucleosomes (or chromatosomes) containing approximately 165 bp of DNA. Histone H1 is said to act as a linker histone and the additional DNA is often referred to as "linker DNA", i.e. the DNA connecting one nucleosome to another in chromosomes. The linker DNA separating two nucleosomes in a chromosome is sometimes longer than 20 bp and may be up to 80 bp in length.

Normal cell turnover in adult humans involves the continuous creation of cells (by cell division) and death of cells in huge numbers daily. During the process of apoptosis chromatin is broken down into mononucleosomes and oligonucleosomes some of which may be found in the circulation. Under normal conditions the level of circulating nucleosomes found in healthy subjects is reported to be low. Elevated levels are found in subjects with a variety of conditions including many cancers, auto-immune diseases, inflammatory conditions, stroke and myocardial infarction (Holdenrieder & Stieber, 2009). Nucleosomes from dead cells may also be shed into other body fluids such as urine, feces, or sputum. Circulating cell free nucleosomes are reported to comprise predominantly mononucleosomes together with associated DNA produced as chromatin fragments by digestion of chromatin on cell death.

DNA abnormalities are characteristic of all cancer diseases. The DNA of cancer cells differs from that of healthy cells in many ways including, but not limited to, point mutations, translocations, gene copy number, micro-satellite abnormalities, DNA strand integrity and nucleotide modifications (for example methylation of cytosine at position 5). These tumour-associated-alterations in DNA structure or sequence are investigated routinely in cancer cells or tissue removed at biopsy or surgery for clinical diagnostic, prognostic and treatment selection purposes. Tumour genetic and epigenetic characteristics vary between different tumour types and between different patients with the same tumour disease. Moreover, these characteristics vary over time within the same cancer of the same patient with the progression of the disease and in the development of acquired resistance to drug or other therapies. Thus, serial investigation of tumour DNA in cells removed at surgery or biopsy may help the clinician to assess minimal residual disease, predict patient prognosis, select appropriate treatments for the patient, monitor disease progression and detect any relapse or acquired treatment resistance at an early stage (possibly many months earlier than radiological detection) and allow potentially successful changes in treatment courses.

However, tissue DNA tests have limitations as invasive biopsy procedures cannot be performed repeatedly on patients. For some patients, biopsy may not be used at all. Biopsy is expensive to perform, uncomfortable for the patient, poses patient risk, and may lead to surgical complications. Moreover, a tumour in a patient may consist of multiple tumoural clones located within different areas of the same tumour or within different metastases (in metastatic cancer) not all of which may be sampled by biopsy. A tissue biopsy DNA investigation therefore provides a snap-shot of the tumour, both in time and in space, amongst different tumour clones located within different areas of a tumour at one particular moment in time.

The blood of cancer patients contains circulating tumour DNA (ctDNA) which is thought to originate from the release of chromatin fragments or nucleosomes into the circulation from dying or dead cancer cells. Tumour derived ctDNA circulates as small DNA fragments consistent with the size expected for mononucleosomes. Investigation of matched blood and tissue samples from cancer patients shows that cancer associated mutations, present in a patient's tumour (but not in his/her healthy cells) are also present in ctDNA in blood samples taken from the same patient (Newman et al, 2014). Similarly, DNA sequences that are differentially methylated (epigenetically altered by methylation of cytosine residues) in cancer cells can also be detected as methylated sequences in ctDNA in the circulation. In addition, the proportion of cell-free circulating DNA (cfDNA) that is comprised of ctDNA is related to tumour burden so disease progression may be monitored both quantitatively by the proportion of ctDNA present and qualitatively by its genetic and/or epigenetic composition. Analysis of ctDNA can produce highly useful and clinically accurate data pertaining to DNA originating from all or many different clones within the tumour and which integrates the tumour clones spatially. Moreover, repeated sampling over time is a much more practical and economic option. Analysis of ctDNA has the potential to revolutionize the detection and monitoring of tumours, as well as the detection of relapse and acquired drug resistance at an early stage for selection of treatments for tumours through the investigation of tumour DNA without invasive tissue biopsy procedures. Such ctDNA tests may be used to investigate all types of cancer associated DNA abnormalities (e.g. point mutations, nucleotide modification status, translocations, gene copy number, micro-satellite abnormalities and DNA strand integrity) and would have applicability for routine cancer screening, regular and more frequent monitoring and regular checking of optimal treatment regimens (Zhou et al, 2012).

Blood, plasma or serum may be used as a substrate for ctDNA assays and any DNA analysis method may be employed including, without limitation, genetic DNA sequencing, epigenetic DNA sequencing analysis (e.g. for sequences containing 5-methylcytosine), PCR, BEAMing, NGS (targeted or whole genome), digital PCR, isothermal DNA amplification, cold PCR (co-amplification at lower denaturation temperature-PCR), MAP (MIDI-Activated Pyrophosphorolysis), PARE (personalized analysis of rearranged ends) and Mass Spectrometry.

As DNA abnormalities are characteristic of all cancer diseases and ctDNA has been observed for all cancer diseases in which it has been investigated, ctDNA tests have potential applicability in all cancer diseases. Cancers investigated include, without limitation, cancer of the bladder, breast, colorectal, melanoma, ovary, prostate, lung liver, endometrial, ovarian, lymphoma, oral, leukaemias, head and neck, and osteosarcoma (Crowley et al, 2013; Zhou et al, 2012; Jung et al, 2010). The nature of ctDNA tests will now be illustrated by outlining some (non-limiting) example approaches.

The first example involves the detection of a cancer associated gene sequence mutation in ctDNA. Blood tests involving the detection of a single gene mutation in ctDNA generally have low clinical sensitivity. There are two reasons for this. Firstly, although all cancers have mutations, the frequency of any particular mutation in a particular cancer disease is usually low. For example, although K-ras and p53 mutations are regarded as two of the more frequent cancer mutations and have been studied in a wide range of cancers including bladder, breast, colon, lung, liver, pancreas, endometrial and ovarian cancers, they were detected in 23%-64% and 17%-54% of cancer tissue samples respectively. Secondly, even if the cancer tissue of a patient does contain the mutation, the level or concentration of mutated ctDNA present in the blood of the patient may be low and difficult to detect. For example, K-ras and p53 mutations could be detected in the ctDNA of 0%-75% of K-ras and p53 tissue positive patients. The sum of these two effects meant that K-ras or p53 mutations were detected in the blood of less than 40% of cancer patients (Jung et al, 2010).

A second example involves the detection of multiple cancer associated gene sequence mutations in ctDNA. Although mutations of any particular gene such as K-ras or p53 may be present in only a minority of cancers, all cancers contain mutations therefore a sufficiently large panel of mutations should in principle facilitate the detection of most or even all tumours. One way to increase the clinical sensitivity of such tests is therefore to test for a wide range of mutations in many genes. Newman et al. have taken this approach for non-small cell lung cancer (NSCLC) and investigated 521 exons and 13 intron sequences from 139 recurrently mutated genes. The mutations studied encompassed multiple classes of cancer associated genetic alterations, including single nucleotide variation (SNV) and fusion genes. In this way the authors reported the detection of more than 95% of stage II-IV tumours and 50% of stage I tumours with 96% specificity in ctDNA blood tests (Newman et al, 2014).

A third example involves the detection of cancer associated epigenetic alterations to particular gene sequences in ctDNA. This approach can be applied to any DNA or nucleotide modification. A prime example of this approach is the detection of genes which are differentially methylated at cytosine residues in certain cancers. A large number of genes have been investigated for this purpose in a variety of cancers. A few of these are SEPTIN-9, APC, DAPK, GSTP1, MGMT, p16, RASSF1A, T1G1, BRCA1, ERα, PRB, TMS1, MLH1, HLTF, CDKN2A, SOCS1, SOCS2, PAX5, PGR, PTGS2 and RARβ2 investigated in bladder, breast, colorectal, melanoma, ovarian and prostate cancers. Typically, bisulfite conversion sequencing methods are used in which DNA is extracted from plasma and then treated with bisulfite which converts unmodified cytosine residues to uracil. Sequencing, PCR or other methods can then be applied to determine whether a particular methylated gene sequence is present. An illustrative example of this approach is the detection of methylated SEPTIN-9 in ctDNA for the detection of Colorectal Cancer (CRC) which was reported to detect 48% of CRC cases with a clinical specificity of 91% (Church et al, 2014).

A fourth example is the "fragmentomics" approach involving sequence analysis of circulating DNA fragments and comparison with the results of nuclease-accessible site analysis (also known as DNase hypersensitivity analysis) of tissues and cell lines. In this approach, the genome wide DNA protein occupancy pattern of any cell type may be established by nuclease digestion of the open (not protein bound) DNA in a cell. Protein bound DNA is protected from nuclease digestion and, following extraction, may be sequenced to identify the unique DNA protein occupancy pattern (or unoccupied open DNA pattern) of a cell type. Circulating cfDNA fragments are similarly protected by protein binding which may be histone in nature, as in nucleosomes, or may be by other proteins such as transcription factors. The boundaries of cfDNA fragments relate to their binding to nucleosomes, transcription factors or other proteins and the fragmentation patterns obtained by sequencing an individual's cfDNA can be built into a map of nucleosome and other protein occupancy. Such cfDNA occupancy maps can be compared to the occupancy maps for known tissues or cancer cell lines derived as nuclease-accessible site maps. This method is reported to indicate that nucleosome spacing in regulatory elements and gene bodies, as revealed by cfDNA sequencing in healthy individuals, correlates strongly with the occupancy patterns of lymphoid and myeloid cell lines. Sequencing of cfDNA from late-stage cancer patients showed additional occupancy patterns that correlated most strongly with occupancy maps of cancer cell lines, often matching the anatomical origin of the patient's cancer (Snyder et al, 2016). This indicates that nucleosome and other protein occupancy analysis of cfDNA patterns may be used both to detect cancer and potentially to identify the organ site of the cancer.

A fifth example involves analysis of global genome DNA methylation patterns in cancer cells and healthy cells in subjects. The DNA of a healthy cell displays a globally dispersed pattern of methylation across the entire genome which reflects the epigenetic state of the particular cell and tissue. The transition of cells from a healthy state to a malignant cancer cell involves a global net loss of DNA methylation (5-methylcytosine) together with localised increases in the levels of 5-methylcytosine residues within regulatory (e.g. gene promoter) regions of the genome with abundant CpG sites clustered together within a short regions of DNA. Thus, cancer cells have global hypomethylation of DNA but the methylated DNA (5-methylcytosine) that does occur tends to be densely clustered in small areas. This means that ctDNA fragments from cancer cells tend to be either very hypomethylated or very hypermethylated with relatively little in between (i.e. at both extremes of methylation level) whereas DNA from normal cells has a different methylation pattern between the two extremes and tends to be more modestly methylated. These properties of cancer DNA have been used as the basis of a physicochemical test for cancer (Sina et al, 2018).

A major problem associated with all these ctDNA analysis methods is that the mutant allele fraction (MAF—the proportion of alleles at a specific genomic location which are mutant) of cfDNA in cancer patients is low. The ctDNA analytic target of the methods is diluted in a larger quantity of circulating cfDNA of hematopoietic origin. This means that the proportion of cfDNA constituted by tumour derived ctDNA is low which places limitations on all ctDNA analysis methods. For this reason, increasing the MAF of patient samples has become a goal of workers in the ctDNA field. The MAF of cfDNA fragments is size dependent and cfDNA fragments of sizes 90-150 bp in length have a higher MAF, and hence higher ctDNA fractions, than larger cfDNA fragments.

Mouliere et al, 2018 showed that enrichment of samples for smaller cfDNA fragments leads to higher MAF, higher ctDNA fractions and improvement in ctDNA detection/analysis results as well as improvement in clinical results for the detection of cancer. Size selection of ctDNA was performed by in silico methods on 254 patients. However, observed ctDNA enrichment was better and clinical results for cancer detection were improved, for in vitro size selection methods performed on 35 patients to physically enrich for ctDNA using a physical gel based method. However, this method is not suitable for routine clinical use.

Cancer patients are reported to have higher cfDNA levels than healthy subjects. Workers in the field have reported ranges of up to 100 ng/ml (mean 30 ng/ml) cfDNA for healthy subjects and up to 1000 ng/ml (mean 180 ng/ml) cfDNA for subjects with cancer (Schwarzenbach et al, 2011). Circulating cfDNA consists of DNA molecules of various sizes up to 20,000 bp in length (Zhou et al, 2012). In agreement with the hypothesis that ctDNA circulates predominantly as mononucleosomes, measured levels of cell free nucleosomes in the circulation are, like DNA levels, higher in cancer patients than in healthy subjects (Holden-rieder et al, 2001). However, raised levels of circulating nucleosomes per se are not used clinically as biomarkers of cancer as nucleosomes are a non-specific product of cell death and raised levels are observed for many conditions involving elevated cell death including acute trauma (Hold-enrieder and Stieber, 2009). As a product of cell death, circulating nucleosome levels can also rise markedly on treatment with cytotoxic drugs or radiotherapy. However, nucleosomes are also cleared from the circulation so levels may spike with treatment and then fall (Holdenrieder et al, 2001).

Although the level of circulating cell free nucleosomes per se has not been used in clinical practice as a blood-based biomarker in cancer, the epigenetic composition of circulating cell free nucleosomes in terms of their histone modification, histone variant, DNA modification and adduct content have been investigated as blood-based biomarkers in cancer (see WO 2005/019826; WO 2013/030577; WO 2013/030579; WO 2013/084002).

There are a variety of methods available for extracting cfDNA from blood, serum or plasma and these have been compared for yield of extracted DNA and for their efficiency of extraction of DNA fragments of different lengths. Phenol-chloroform and sodium iodide extraction methods provide the highest yield and extract small DNA fragments of less than 200 bp in length. Other methods tested (including commercially available methods) are reported to have lower DNA extraction yields and may fail to extract small DNA fragments of less than 200 bp in length (Fong et al, 2009).

Extraction of cfDNA from blood, serum or plasma for analysis of ctDNA is usually performed using commercially available DNA extraction products. Such extraction methods claim high recoveries of circulating DNA (>50%) and some products (for example, the QIAamp Circulating Nucleic Acid Kit produced by Qiagen) are claimed to extract DNA fragments of small size. Typical sample volumes used are in the range 1-5 mL of plasma.

There are currently no ctDNA based tests in widespread routine use for the detection or diagnosis of common cancers due to a number of limitations. A major methodological limitation is a requirement for high quality DNA. Current ctDNA sampling methods produce poor quality ctDNA samples due to the nature of the sample. The main difficulty lies in the presence of large amounts of non-tumour cfDNA in the circulation which complicates any analysis of ctDNA. Estimates from different workers vary but the fraction of ctDNA present in the circulation can be too low to detect. For most cancer patients the ctDNA fraction constitutes only a small part of cfDNA. For example, recent studies report that the ctDNA fraction increases with tumour size in pre-treatment lung cancer patients. The highest level found was 3.2% in a patient with a large tumour burden but most patients were found to have ctDNA fractions below 0.1% (Newman et al, 2014). This means that for many patient samples, a very low level of ctDNA must be analysed in the presence of a much higher level of non-tumour derived cfDNA. Moreover, this non-tumour derived cfDNA is from the same subject and hence of similar sequence and will interfere in any method for the quantification or analysis of ctDNA.

Although the level of cfDNA in cancer patients is often raised, the ctDNA fraction is low and the total ctDNA levels may be lower than the observed increase in cfDNA. This may indicate that at least some of the increase in cfDNA may be tumour associated, perhaps related to the tumour environment or stroma, rather than directly derived from malignant cancer cells containing cancer associated DNA mutations.

A similar problem of low MAF or low tumour-associated or tumour derived fraction occurs for the measurement of circulating cell free nucleosomes and/or the epigenetic composition of circulating nucleosomes as biomarkers for cancer. Nucleosomes per se are an indicator of cell death and are released as part of the normal cell turnover process of the body as well as in conditions associated with elevated levels of cell death such as autoimmune diseases, stroke, sepsis, post trauma, burns, myocardial infarction, cerebral stroke, during graft rejection after organ transplantation and after severe exercise. This means that nucleosomes of tumour origin circulate together with other non-tumour nucleosomes of various cellular and tissue origins and may constitute a low fraction of all circulating nucleosomes. Non-tumour nucleosomes will interfere in any method for the quantification or epigenetic analysis of tumour associated nucleosomes or of nucleosomes of tumour origin. A similar effect may occur in other body fluids. Feces, for example, may contain nucleosomes and associated DNA of colorectal cancer cell origin together with nucleosomes originating in healthy colon or rectal cells. Sputum may contain nucleosomes and associated DNA of lung cancer cell origin together with nucleosomes originating in healthy lung cells. Similar effects will occur in other body fluids.

There is therefore a great need for better methods for the enrichment of tumour derived or tumour associated DNA and nucleosomes from body fluid samples. There is also a need for analytical methods to distinguish tumour and non-tumour circulating cell free nucleosomes for improved detection of cancer disease states.

SUMMARY OF THE INVENTION

According to a first aspect of the invention, there is provided a method for separating circulating cell free nucleosomes comprising linker DNA from a biological fluid sample, wherein said method comprises the steps of:

(i) contacting the sample with a binding agent which binds to:
   (a) nucleosome associated linker DNA;
   (b) a chromatin binding protein which binds to linker DNA; or
   (c) a core nucleosome feature associated with linker DNA; and
(ii) isolating nucleosomes from the sample which are bound to the binding agent in step (i).

According to a further aspect of the invention, there is provided a method for separating circulating cell free nucleosomes which do not comprise linker DNA from a biological fluid sample, wherein said method comprises the steps of:

(i) contacting the sample with a binding agent which binds to:
   (a) nucleosome associated linker DNA;
   (b) a chromatin binding protein which binds to linker DNA; or
   (c) a core nucleosome feature associated with linker DNA; and
(ii) isolating nucleosomes from the sample which are not bound to the binding agent in step (i).

According to a further aspect of the invention, there is provided a method for separating circulating cell free nucleosomes which do not comprise linker DNA from a biological fluid sample, wherein said method comprises the steps of:

(i) contacting the sample with a binding agent which binds to a clipped histone molecule from which all or part of the histone tail is absent:
(ii) isolating nucleosomes from the sample which are bound to the binding agent in step (i).

According to a further aspect of the invention, there is provided a method for isolating purified circulating tumour DNA (ctDNA) from a biological fluid sample, wherein said method comprises the steps of:

(i) performing the method as defined herein; and
(ii) extracting the DNA from the isolated nucleosomes.

According to a further aspect of the invention, there is provided a method of diagnosing cancer comprising:

(i) performing the method as defined herein to isolate circulating tumour nucleosomes from a biological sample obtained from a patient; and
(ii) analysing the isolated circulating tumour nucleosomes and/or associated DNA.

According to a further aspect of the invention, there is provided a method for obtaining an antibody or other binding agent that preferentially binds to cell free nucleosomes of disease origin, wherein said method comprises the steps of:

(i) using a nucleosome containing approximately 150 base pairs or less of DNA as an antigen against which to produce an antibody or other binding agent;

(ii) presenting the antibody or other binding agent obtained in step (i) to a nucleosome containing approximately 165 base pairs or more of DNA; and
(iii) selecting the antibody or other binding agent that binds to the nucleosome of step (i), but not to the nucleosome of step (ii).

According to a further aspect of the invention, there is provided a method for obtaining an antibody or other binding agent that preferentially binds to cell free nucleosomes of non-disease origin, wherein said method comprises the steps of:

(i) using a nucleosome containing approximately 165 base pairs or more of DNA as an antigen against which to produce an antibody or other binding agent;
(ii) presenting the antibody or other binding agent obtained in step (i) to a nucleosome containing approximately 150 base pairs or less of DNA; and
(iii) selecting the antibody or other binding agent that binds to the nucleosome of step (i), but not to the nucleosome of step (ii).

DETAILED DESCRIPTION OF THE INVENTION

We have previously reported methods for the epigenetic analysis of cell free nucleosomes in blood and other body fluids for the diagnosis of disease (see WO2013/030577, WO2013/030578, WO2013/030579, WO2013/084002). As discussed herein, cell free nucleosomes of disease origin are released into the circulation, but these are diluted with cell free nucleosomes already present in the circulation due to normal (healthy) cell turnover. Any such nucleosomes of non-disease origin will interfere in the genetic or epigenetic analysis of nucleosomes released from diseased cells. Sepa- ration and removal of cell free nucleosomes of non-disease (i.e. healthy) origin from a body fluid sample will lead to higher purity of cell free nucleosomes of disease origin providing improved results for the analysis of disease derived nucleosomes or chromatin fragments in the sample.

Each nucleosome in a chromosome in a living cell con- sists of a protein complex of eight highly conserved core histones (comprising of a pair of each of the histones H2A, H2B, H3, and H4). Around this complex are wrapped approximately 145-147 base pairs (bp) of DNA. Another histone, H1, may be located on the nucleosome outside of the core histones and binds a further 20 bp of DNA to produce nucleosomes (or chromatosomes) containing approximately 165 bp of DNA. This further DNA is referred to in the art as "linker DNA", i.e. the DNA connecting one nucleosome to another. The DNA separating two nucle- osomes in a chromosome may be longer than 20 bp, for example if adjacent nucleosomes both contain H1, and may be up to 80 bp in length.

We have previously reported that cell free nucleosomes originating from a tumour less frequently contain histone H1 than nucleosomes originating in healthy cells (see WO 2017/068371). This difference may be exploited for immunoaffinity enrichment of disease associated or derived nucleosomes using antibody binders for H1 to separate nucleosomes that do, or do not, contain histone H1.

Figure 1:
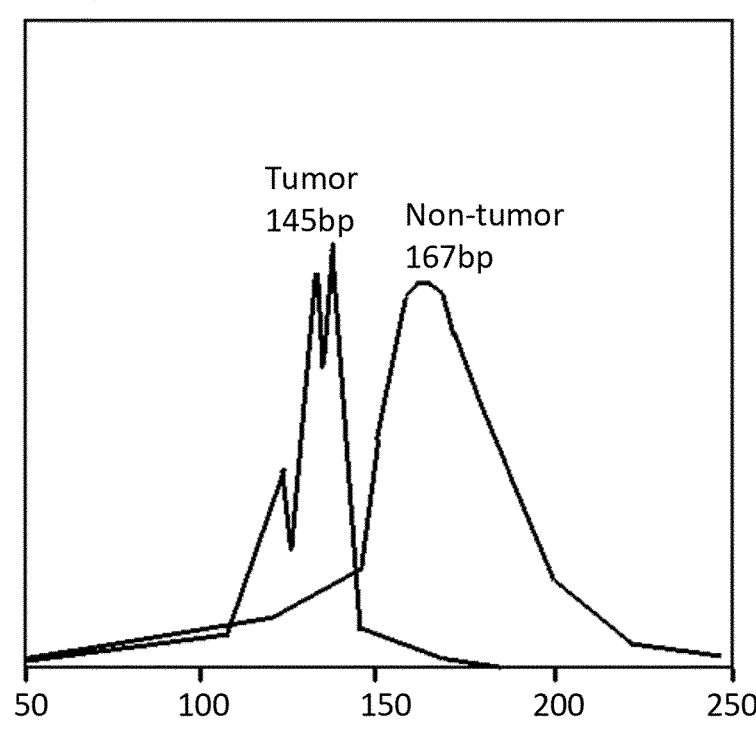
FIG. 1. Illustration of the size distribution of circulating DNA fragments (bp) associated with circulating nucleosomes or chromatin fragments of tumour origin and non-tumour origin. The majority of tumour derived DNA fragments are less than 150 bp in length and the majority of non-tumour derived DNA fragments are more than 150 bp in length.

We now report that nucleosomes can be separated by other means. These means utilise separation of nucleosomes based on nucleosome features associated with the presence or absence of linker DNA. Underhill et al have studied the size range of ctDNA fragments produced by human cancer xenografts in rats compared to the size range of healthy rat cfDNA. As illustrated in FIG. 1, circulating DNA fragments occur in a range of sizes up to approximately 230 bp in length. In healthy subjects, circulating cfDNA is predominantly of haematopoietic origin and has a range of fragment sizes varying from approximately 150-230 bp in length together with smaller amounts of larger DNA fragments corresponding to circulating oligonucleosomes. The most common size of healthy haematopoietic cfDNA is approximately 167 bp in length with only a very small proportion of fragments smaller than 150 bp. Haematopoietic cfDNA is also present in subjects with conditions such as cancer and pregnancy but additional shorter circulating DNA fragments of approximately 120-150 bp are also present. The ctDNA fragment size shows a 10 bp periodicity which is related to the nucleosomal DNA helical periodicity and the most common sizes are 134 bp and 144 bp in length. Therefore, the majority of healthy cfDNA is more than 160 bp in length and the majority of ctDNA is less than 150 bp in length. Without being bound by theory, the inventors reasoned that most circulating cell free nucleosomes of non-tumour (and non-fetal) origin can be deemed to contain linker DNA whereas circulating cell free nucleosomes of tumour origin can be deemed to contain no linker DNA.

Similarly, short approximately 150 bp DNA (in particular about 145 bp DNA) nucleosomes comprise a greater proportion of total circulating cell free nucleosomes in pregnant women than in non-pregnant healthy subjects and are thought to be of fetal or placental origin.

Furthermore, it was previously shown that nucleosomes containing histone H1 could be isolated from blood samples using an anti-histone H1 antibody immobilised on a solid support as an immunosorbent (WO 2017/068371).

Surprisingly, the inventors have now shown that the protein histone H1 (itself) immobilised on a solid support as an immunosorbent can be used to bind and remove nucleosomes containing linker DNA from plasma samples. In addition, other binding proteins that bind to nucleosomes containing linker DNA, can also be used in a similar manner to bind and remove nucleosomes containing linker DNA from serum or plasma or other body fluid samples. Antibodies, or other binders, directed to bind to molecules that bind to nucleosomes containing linker DNA, can also be used in a similar manner to bind and remove nucleosomes containing linker DNA from serum or plasma or other body fluid samples.

Nucleosomes Comprising Linker DNA

The present inventors have found that separation can occur through (i) use of histone feature (e.g. H1) to bind to linker DNA, (ii) use of a (non-histone) chromatin binding protein to bind to linker DNA, (iii) use of an antibody or other binder to bind a chromatin binding protein which binds to linker DNA, or (iv) use of an antibody or other binder which binds to a nucleosome feature associated with linker DNA.

Therefore, according to a first aspect of the invention there is provided a method for separating circulating cell free nucleosomes comprising linker DNA from a biological fluid sample, wherein said method comprises the steps of:

(i) contacting the sample with a binding agent which binds to:
    (a) nucleosome associated linker DNA;
    (b) a chromatin binding protein which binds to linker DNA; or
    (c) a core nucleosome feature associated with linker DNA; and
(ii) isolating nucleosomes from the sample which are bound to the binding agent in step (i).

It will be understood that the method of the first aspect can be used in a negative selection method for removing nucleosomes comprising linker DNA and isolating nucleosomes without linker DNA. Therefore, according to a second aspect of the invention there is provided a method for separating circulating cell free nucleosomes which do not comprise linker DNA from a biological fluid sample, wherein said method comprises the steps of:

(i) contacting the sample with a binding agent which binds to:
    (a) nucleosome associated linker DNA;
    (b) a chromatin binding protein which binds to linker DNA; or
    (c) a core nucleosome feature associated with linker DNA; and
(ii) isolating nucleosomes from the sample which are not bound to the binding agent in step (i).

In one embodiment, the binding agent which binds to nucleosome associated linker DNA is a histone protein selected from histone H1, macroH2A or a fragment or an engineered analogue thereof.

In one embodiment, the binding agent which binds to nucleosome associated linker DNA is histone H1, or a fragment or an engineered analogue thereof. Therefore, according to a further aspect of the invention, there is provided a method for separating cell free nucleosomes with linker DNA from cell free nucleosomes without linker DNA from a biological fluid sample (e.g. by affinity purification), wherein said method comprises the steps of:

contacting the sample with histone H1; and
(ii) isolating nucleosomes from the sample which are bound to histone H1 in step (i).

It will be understood that methods of the invention may be performed using histone H1, or a fragment or an engineered analogue thereof. Histone H1 has several isoforms that are known in the art. In one embodiment, the histone H1 is histone H1.0.

Methods of separation described herein may be used to isolate nucleosomes of disease (or fetal) origin due to the absence of linker DNA. Therefore, in one embodiment, there is provided a method for isolating circulating cell free nucleosomes of disease or fetal origin from a biological fluid sample (e.g. by affinity purification), wherein said method comprises the steps of:

(i) contacting the sample with histone H1; and
(ii) isolating nucleosomes from the sample which are not bound to histone H1 in step (i).

Some epigenetic nucleosome features interact with or affect the stability of nucleosome associated linker DNA and/or histone H1. For example, the basic linker of the histone isoform macroH2A (also referred to as "mH2A") stabilizes linker DNA at the entry/exit site of the nucleosome (Bowerman and Wereszczynski, 2016). The presence of macroH2A also displaces the natural binding of histone H1 to chromatosomes in vivo. For this reason, macroH2A may be regarded as an internal nucleosome binder of linker DNA that includes elements or domains that bind linker DNA. Therefore, in one embodiment macroH2A, or a linker DNA binding sequence, a domain of macroH2A or an engineered analogue thereof, may be useful as a high affinity binder which binds to nucleosome associated linker DNA.

In one embodiment, the binding agent which binds to nucleosome associated linker DNA is macroH2A, or a fragment or an engineered analogue thereof. Therefore, according to a further aspect of the invention, there is provided a method for separating cell free nucleosomes with linker DNA from cell free nucleosomes without linker DNA from a biological fluid sample (e.g. by affinity purification), wherein said method comprises the steps of:

(i) contacting the sample with macroH2A, or a fragment or an engineered analogue thereof; and (ii) isolating nucleosomes from the sample which are bound to macroH2A in step (i).

As well as histone proteins, many (non-histone) chromatin binding proteins may be used to bind to linker DNA. Such proteins include, without limitation, Chromodomain Helicase DNA Binding Protein (CHD), DNA (cytosine-5)-methyltransferase (DNMT), High mobility group or high mobility group box proteins (HMG or HMGB), Poly [ADP-ribose] polymerase (PARP), proteins containing Methyl-CpG-binding domains (MBD), e.g. MECP2 and certain transcription factors that bind to nucleosomal linker DNA in a non-sequence dependent fashion, such as the transcription factor p53.

In one embodiment, the binding agent binds to a chromatin binding protein which binds to nucleosomes containing linker DNA. Reference to a "chromatin binding protein" which binds nucleosomes in the presence of linker DNA refers to a protein which binds (i.e. an adduct) to the linker DNA portion of the cell free nucleosome. The chromatin binding protein which binds only in the presence of linker DNA either preferentially or selectively therefore may be used as a marker to determine if linker DNA is present in the cell free nucleosome. Without limitation, such proteins include the MBD, CHD, DNMT and PARP families of proteins. It will be understood that these protein families include multiple members. For example, there are at least 9 CHD family members CHD1-CHD9. It will be understood that the term "chromatin" refers to the complex formed of DNA and histone proteins when the DNA is packaged within a cell. Therefore, histones are a component of chromatin and the term "chromatin binding protein" does not include the histone proteins themselves. Thus histone proteins, e.g. H1, H2A, H2B, H3 and H4 are not chromatin binding proteins, i.e. a chromatin binding protein is not a histone protein.

Chromatin binding proteins include a DNA binding domain which binds to nucleosomes in the context of linker DNA in order to carry out their functions in vivo. For example, CHD1 binds to linker DNA through a C-terminal DNA binding domain and remodels chromatin using energy derived from ATP hydrolysis. The observed ATP hydrolysis activity is high when CHD1 is added to nucleosomes containing a 201 bp fragment of DNA, but low or absent when added to free DNA or to nucleosomes containing a 147 bp fragment of DNA. Truncated CHD1 proteins, in which the DNA binding domain is absent, do not bind nucleosomes or DNA and have little or no ATP hydrolysis activity (Ryan et al, 2011).

HMG proteins have similar nucleosome linker DNA binding properties to histone H1. Furthermore, they compete with histone H1 for binding to linker DNA and to the nucleosome entry/exit dyad and also protect the linker DNA from nuclease digestion (Nalabothula et al, 2014).

DNMT1 also binds to nucleosomes that contain at least 20 bp of linker DNA and preferentially methylates linker DNA, but does not bind to nucleosomes that do not contain linker DNA (Schrader et al, 2015).

Similarly, the MBD protein MECP2 binds to nucleosomes that contain linker DNA and protects the linker DNA from nuclease digestion in a similar manner to histone H1 binding, but protects only about 11 bp (as opposed to about 20 bp for histone H1) of linker DNA (Dhasarathy and Wade, 2008).

PARP-1 binds to nucleosomes containing linker DNA with an exposed double-strand break. In living cells, PARP-1 binding induces a conformational change in the protein which results in its DNA-dependent activation and poly(ADP)-ribosylation of the target proteins including core histones (Sultanov et al, 2017).

As these proteins bind to mononucleosomes containing linker DNA, we reasoned that such molecules, may be used directly to separate, purify or enrich mononucleosomes with linker DNA.

Therefore, in one embodiment, the binding agent which binds to nucleosome associated linker DNA is a chromatin binding protein or a fragment or an engineered analogue thereof. According to a further aspect of the invention, there is provided a method for separating circulating cell free nucleosomes with linker DNA from cell free nucleosomes without linker DNA from biological fluid sample (e.g. by affinity purification), wherein said method comprises the steps of:

(i) contacting the sample with a chromatin binding protein (or a fragment or an engineered analogue thereof) which binds to nucleosomes comprising linker DNA; and (ii) isolating nucleosomes from the sample which are bound to the chromatin binding protein in step (i).

In one embodiment, there is provided a method for isolating circulating cell free nucleosomes of disease or fetal origin from a biological fluid sample (e.g. by affinity purification), wherein said method comprises the steps of:

(i) contacting the sample with a chromatin binding protein which binds to nucleosomes comprising linker DNA; and (ii) isolating nucleosomes from the sample which are not bound to the chromatin binding protein in step (i).

In one embodiment, the chromatin binding protein which binds to linker DNA is selected from:

(a) a Chromodomain Helicase DNA Binding Protein;

(b) a DNA (cytosine-5)-methyltransferase;

(c) a High mobility group box protein;

(d) a Poly [ADP-ribose] polymerase;

(e) a Methyl-CpG-binding domain protein; or (f) a transcription factor

In one embodiment, the chromatin binding protein which binds to linker DNA is selected from:

(a) a Chromodomain Helicase DNA Binding Protein;

(b) a DNA (cytosine-5)-methyltransferase;

(c) a High mobility group box protein;

(d) a Poly [ADP-ribose] polymerase; or (e) a Methyl-CpG-binding domain protein.

In one embodiment, the chromatin binding protein which binds to linker DNA is selected from:

(a) Chromodomain Helicase DNA Binding Protein 1 (CHD1);

(b) DNA (cytosine-5)-methyltransferase 1 (DNMT1);

(c) High mobility group box 1 protein (HMGB1);

(d) Poly [ADP-ribose] polymerase 1 (PARP1);

15

(e) Methyl-CpG-binding domain protein selected from: MBD1, MBD2, MBD3, MBD4 and Methyl CpG binding protein 2 (MECP2); or (f) p53.

In one embodiment, the chromatin binding protein which binds to linker DNA is selected from:

(a) Chromodomain Helicase DNA Binding Protein 1 (CHD1);

(b) DNA (cytosine-5)-methyltransferase 1 (DNMT1);

(c) High mobility group box 1 protein (HMGB1);

(d) Poly [ADP-ribose] polymerase 1 (PARP1); or (e) Methyl-CpG-binding domain protein selected from: MBD1, MBD2, MBD3, MBD4 and Methyl CpG binding protein 2 (MECP2).

The chromatin moieties CHD1, DNMT1, HMGB1, PARP1, MBD and p53 are binders of linker DNA.

The chromatin binding proteins explicitly listed herein are known in the art. The native sequences for these proteins may be found in publicly available databases, for example, The Universal Protein Resource "UniProt" (CHD1 UniProt ID: O14646; DNMT1 UniProt ID: P26358; HMGB1 UniProt ID: P09429; PARP1 UniProt ID: P09874; MBD1 UniProt ID: Q9UIS9; MBD2 UniProt ID: Q9UBB5; MBD3 UniProt ID: O95983; MBD4 UniProt ID: O95243; MECP2 UniProt ID: P51608).

Histone H1 protein, or any chromatin binding protein or protein domain that binds nucleosomes containing linker DNA, may be reengineered to produce a protein or peptide of higher binding affinity or improved specificity (for example to minimise the binding of nucleosomes without linker DNA) or both. Therefore, in one embodiment of the invention the chromatin binding protein is a genetically reengineered protein with an altered amino acid sequence that binds more strongly to nucleosomes containing linker DNA and/or less strongly to nucleosomes without linker DNA. Methods for reengineering proteins are well known in the art, for example the method of (Wiesler and Weinzierl, 2010). In a preferred embodiment the genetically engineered protein is an engineered analogue of H1, i.e. a reengineered H1 moiety.

In one embodiment the chromatin binding protein which binds to nucleosomes comprising linker DNA is selected from the CHD, DNMT, HMGB, MBD and PARP families of proteins. It will be clear to those skilled in the art that the protein domain of interest in the context of the current invention is primarily the DNA binding domain and any other domains (e.g. any enzyme domains or chromatin remodelling domains) may not be essential. Therefore, fragments of the binding proteins disclosed herein may be used. Thus, in another embodiment the binding protein comprises the DNA binding domain of a chromatin binding protein that binds to linker DNA in the context of a nucleosome.

In a preferred embodiment the histone H1 protein or the chromatin binding protein is coated on a solid support, such as sepharose, sephadex, plastic or magnetic beads. In one embodiment, said solid support comprises a porous material. In another embodiment the histone H1 protein or chromatin binding protein is derivatised to include a tag or linker which can be used to attach the histone H1 or chromatin binding protein to a suitable support which has been derivatised to bind to the tag. Many such tags and supports are known in the art (e.g. Sortag, Click Chemistry, biotin/streptavidin, his-tag/nickel or cobalt, GST-tag/GSH, antibody/epitope tags and many more). For ease of use, the histone H1 protein or chromatin binding protein coated support may be included within a device, for example a microfluidic device.

In one embodiment, the binding between the linker DNA associated with the nucleosome and the derivatised histone H1 or chromatin binding protein may occur in the liquid phase (i.e. prior to binding the derivatised histone H1 or chromatin binding protein to the solid support). Binding of the derivatised histone H1 or chromatin binding protein to a solid support may then be achieved simultaneously or subsequently using a linker reaction.

According to a further aspect of the invention, there is provided a method for separating circulating cell free nucleosomes with linker DNA from cell free nucleosomes without linker DNA from a biological fluid sample by affinity purification, wherein said method comprises the steps of:

(i) contacting the sample with a binding agent that binds to a chromatin binding protein which binds to nucleosomes comprising linker DNA; and (ii) isolating nucleosomes from the sample which are bound to the binding agent in step (i).

In this aspect of the invention, the binding of nucleosomes through their linker DNA occurs indirectly by binding of a protein that binds (directly) to nucleosomes through their linker DNA.

In one embodiment, there is provided a method for isolating circulating cell free nucleosomes of disease or fetal origin from a blood, serum or plasma sample by affinity purification, wherein said method comprises the steps of:

(i) contacting the sample with a binding agent that binds to a chromatin binding protein which binds to nucleosomes comprising linker DNA; and (ii) isolating nucleosomes from the sample which are not bound to the binding agent in step (i).

In one embodiment the binding agent that binds to a chromatin binding protein is selected from an antibody (or binding fragment thereof), an affimer or an aptamer. In a further embodiment, the binding agent is an antibody.

It will be understood that the embodiments described hereinbefore for the chromatin binding proteins (when used as direct nucleosome binders), also apply to this aspect of the invention where a binding agent directed to said chromatin binding proteins (i.e. as an indirect method of nucleosome binding) is used.

In one embodiment, the binding agent is directed to bind to a Chromodomain Helicase DNA Binding Protein, a DNA (cytosine-5)-methyltransferase, a Poly [ADP-ribose] polymerase protein and/or p53. In one embodiment, the binding agent is not directed to bind to a High mobility group box protein. In a further embodiment, the binding agent is not directed to bind to a Methyl-CpG-binding domain protein.

According to a further aspect of the invention, there is provided a binding agent which binds to a core nucleosome feature associated with linker DNA. References to a "core nucleosome feature" associated with linker DNA, refer to a feature of the core nucleosome particle (e.g. one of the core histone proteins, such as H2A, H2B, H3 or H4, including post-translational modifications and isoforms thereof) which occurs only or predominantly in nucleosomes that contain linker DNA. In some cases, the nucleosome feature may bind to, stabilise or protect linker DNA from nuclease digestion.

Nucleosomes containing the histone isoforms macroH2A are thought to stabilize linker DNA (Bowerman and Wereszczynski, 2016). The present inventors have found that this type of histone isoform is more preferentially associated with cell free nucleosomes containing linker DNA and therefore may be used as a marker to separate nucleosomes of healthy origin from a biological sample.

Thus, in one embodiment, the core nucleosome feature associated with linker DNA is histone isoform macroH2A.

Therefore, according to a further aspect of the invention, there is provided a method for separating cell free nucleosomes with linker DNA from cell free nucleosomes without linker DNA from a biological fluid sample by affinity purification, wherein said method comprises the steps of:

(i) contacting the sample with a binding agent that binds to a macroH2A or a fragment thereof; and (ii) isolating nucleosomes from the sample which are bound to the binding agent in step (i).

In one embodiment, there is provided a method for isolating circulating cell free nucleosomes of disease or fetal origin from a blood, serum or plasma sample by affinity purification, wherein said method comprises the steps of:

(i) contacting the sample with a binding agent that binds to a macroH2A or a fragment thereof; and (ii) isolating nucleosomes from the sample which are not bound to the binding agent in step (i).

As discussed herein, nucleosomes with or without linker DNA may be defined by the length of DNA wrapped around the nucleosome. Therefore, according to a further aspect of the invention, there is provided a method for separating cell free nucleosomes with linker DNA from cell free nucleosomes without linker DNA from a biological fluid sample (e.g. by affinity purification), wherein said method comprises the steps of:

(i) contacting the sample with a binding agent engineered to selectively bind to nucleosomes comprising more than 150 base pairs of DNA in length, wherein the binding agent binds to a nucleosome feature associated with nucleosomes with linker DNA; and (ii) isolating nucleosomes from the sample which are not bound to the binding agent in step (i).

In one embodiment, there is provided a method for isolating circulating cell free nucleosomes of disease or fetal origin from a blood, serum or plasma sample by affinity purification, wherein said method comprises the steps of:

(i) contacting the sample with a binding agent engineered to selectively bind to nucleosomes comprising more than 150 base pairs of DNA in length, wherein the binding agent binds to a nucleosome feature associated with nucleosomes with linker DNA; and (ii) isolating nucleosomes from the sample which are bound to the binding agent in step (i).

The subsets of nucleosomes produced by separation based on these various features may be different and can be useful for a variety of applications for research purposes and for clinical applications. For example, the structure of nucleosomes may vary in cancer cells compared to healthy cells. The use of antibodies or other binders directed to bind to one or more of these features that are more common in nucleosomes derived from cancer cells than healthy cells (or vice versa) allows for the separation of cell free nucleosomes of tumour origin, either by positive or negative selection, in a biological sample which contains cell free nucleosomes with a mixture of cellular origins. Applications of the invention include separation of tumour derived nucleosomes, separation of maternal and fetal nucleosomes in samples taken from pregnant women, disease derived nucleosomes from normal circulating nucleosomes, nucleosomes containing methylated or unmethylated DNA, as well as a variety of subsets of nucleosomes useful for research or other purposes.

In one embodiment, nucleosomes comprising approximately 150 or more base pairs of DNA in length refer to nucleosomes which have retained linker DNA. The nucleosome core particle (i.e. the histone octamer comprising of a pair of each of the histones H2A, H2B, H3, and H4) consists of approximately 150 bp of DNA, such as between 145 and 150 bp of DNA, in particular 147 bp of DNA. Therefore, nucleosomes comprising more than 150 bp of DNA (such as more than 155 bp, 160 bp or 165 bp of DNA) contain linker DNA. In one embodiment, the binding agent binds to nucleosomes consisting of at least 165 base pairs of DNA. In one embodiment, the binding agent does not bind to nucleosomes comprising approximately 150 bp or less of DNA, i.e. the binding agent selectively binds to nucleosomes containing linker DNA.

In one embodiment, the binding agent binds to a region within linker DNA. In this embodiment, the binding agent binds (directly) to the region of DNA not in contact with the histone (core) octamer, i.e. the linker DNA.

The methods described herein may be used for isolating, enriching and/or purifying circulating cell free nucleosomes of disease origin, in particular from circulating cell free nucleosomes of healthy origin. References herein to "disease origin" refer to nucleosomes and chromatin fragments originating from diseased (e.g. abnormal or unhealthy) cells. References herein to "healthy origin" refer to nucleosomes and chromatin fragments originating from healthy (e.g. normal or non-diseased) cells.

It will be understood by a person skilled in the art that when the binding agent is directed to bind features associated with linker DNA, then this may be used to bind (and remove) nucleosomes of healthy origin from the sample, i.e. the nucleosomes of disease origin are obtained in the unbound portion of the sample. This may therefore be referred to as a negative selection method. Depending on whether a positive or negative selection method is used will determine which nucleosome fraction is isolated (i.e. the bound fraction for a positive selection method or the free/eluted fraction for a negative selection method).

In one embodiment, the circulating cell free nucleosomes are of tumour origin. Therefore, the present method finds particular use as a method of enriching a sample for circulating cell free nucleosomes of tumour origin. The enriched sample may then be used for subsequent analysis and, for example, for use in diagnostic methods.

Features associated with nucleosomes comprising linker DNA (i.e. nucleosomes comprising "approximately 165 bp or longer DNA nucleosomes" or "long nucleosomes") that may be used for separation of nucleosomes include histone H1, macroH2A and chromatin binding proteins which bind to linker DNA. In one embodiment, binders of linker DNA (e.g. histone H1, CHD, DNMT, HMGB, PARP and macroH2A or a DNA binding domain of such proteins) may be used directly to bind and isolate nucleosomes comprising linker DNA.

In another aspect of the invention, nucleosomes comprising linker DNA may be isolated using antibodies or other binders to these features including binders to macroH2A, CHD, DNMT, HMGB and PARP. In this embodiment, nucleosomes comprising linker DNA additionally comprising a binder of linker DNA are isolated. Any nucleosomes comprising linker DNA and not including such a feature or binder, for example with "free" linker DNA, are not isolated. In one embodiment, the sample may be exposed to a mixture of binders to different features (for example, immobilised on a solid phase substrate) to isolate nucleosomes comprising linker DNA incorporating any number of different nucleosome features associated with linker DNA. In another embodiment the sample may be exposed serially to multiple binders to different nucleosome features associated with linker DNA.

It will be understood that embodiments of the invention may be used in combination to bind nucleosomes comprising linker DNA that both do, and do not, additionally comprise a feature such as H1, CHD, DNMT, HMGB, PARP or macroH2A. The combination may involve exposing the sample serially or simultaneously to multiple antibodies and/or linker DNA binding proteins.

Methods of contacting and isolating the nucleosomes from a sample as required herein are well known in the art and any suitable separation method may be used. For example, separation methods may include affinity chromatography or magnetic antibody beads. If using an affinity column chromatography set up, for example, it will be understood that the sample may be passed through an affinity column comprising the required binding agent(s). Either the nucleosomes bound to the solid phase or the flow through (i.e. the unbound nucleosomes) may be collected for further analysis, depending on whether a positive or negative selection method described herein is employed.

It will be understood that binding agents of the invention may be used regardless of whether target nucleosomes already comprise a binder of linker DNA. In such cases (i.e. the linker DNA is already bound to another molecule) the isolation is based on substitution of that binder of linker DNA by binding to the binding agent used in the invention due to a high relative concentration and/or high relative binding affinity of the binder of the invention compared to the binder initially bound to the nucleosome, e.g. due to equilibrium and kinetic reasons.

It is clear that a protein of higher binding affinity may displace a protein of lower binding affinity from its position on a nucleosome, especially if the higher binding affinity protein is present in excess. The rate at which displacement occurs will depend on the relative affinities, concentrations and the off-rate of the (currently) bound moiety. In one embodiment, H1 is used as the binding agent. H1 is useful as a binding agent because it has a high binding affinity for nucleosomes containing linker DNA.

In one embodiment, tumour nucleosome and circulating tumour DNA (ctDNA) isolation is performed by an immunological affinity purification method employing a binding agent, for example a binding agent directed to CHD, DNMT, HMGB, PARP, MBD or macroH2A. It will be clear to persons skilled in the art that any binding agent capable of specific binding to the required target may be used for affinity purification methods of the invention. Such binding agents may include, without limitation, antibodies, aptamers, affimers or binding proteins (e.g. nucleosome binding proteins).

Antibodies may be raised by a variety of methods known in the art including immunization and library methods such as phage display. The immune response may be induced against, or the library may be selected for binding to, the moiety or antigen of interest. Antibodies directed to bind, for example, to CHD1, DNMT1, HMGB1, PARP1, MBD or macroH2A may be raised against a variety of such moieties including the whole protein amino acid sequence and may optionally contain further histone post-translational modifications (PTMs). The protein may be purified from living cells or produced synthetically. Alternatively, a peptide sequence representing a part of the amino acid sequence may be used and this may also optionally contain histone post-translational modifications. It will be clear to those skilled in the art that binding agents directed to bind to any part of, or all of the required target may be employed in methods of the invention.

Nucleosomes without Linker DNA

Features preferentially, or selectively, associated with short 150 bp (or less) DNA nucleosomes may similarly be used for separation of nucleosome types. It will be understood that nucleosomes comprising less than about 150 base pairs of DNA in length refer to nucleosomes which have lost their linker DNA. The nucleosome core particle (i.e. the histone octamer comprising of a pair of each of the histones H2A, H2B, H3, and H4) consists of approximately 150 bp of DNA, such as between 145 and 150 bp of DNA, in particular 147 bp of DNA. Therefore, nucleosomes comprising less than about 150 bp of DNA (such as less than 149 bp, less than 148 bp, less than 147 bp, less than 146 bp or less than 145 bp of DNA) do not contain linker DNA. In one embodiment, the binding agent selectively binds to nucleosomes comprising less than 150 bp of DNA, such as less than 149 bp, 148 bp, 147 bp, 146 bp or 145 bp of DNA. In one embodiment, the binding agent binds to nucleosomes consisting of less than 147 bp of DNA. In one embodiment, the binding agent does not bind to nucleosomes comprising more than 150 bp of DNA, i.e. the binding agent selectively binds to nucleosomes without linker DNA.

This method uses positive selection to separate (i.e. purify) nucleosomes of disease origin by binding to nucleosomes which do not comprise linker DNA. Such features include, for example without limitation, the clipping and tertiary folding patterns of core histone tails and/or inclusion of the histone isoform H2AZ. Histone H2AZ is associated with reduced protection of nucleosome associated DNA from nuclease activity (Bonisch et al, 2012) and elevated levels of histone H2AZ are associated with a number of malignant cancers (Yang et al, 2018). Therefore, in one embodiment, the nucleosome feature associated with nucleosomes without linker DNA is histone isoform H2AZ. Similarly, the chromatin proteins H2Abdb (an isoform of histone H2A) and CENP-A (an isoform of histone H3) are associated with reduced protection of nucleosome associated DNA from nuclease activity. H2Abdb was shown to bind DNA ends less tightly (Bao et al, (2004)) while nucleosomes containing CENP-A have been shown to disassemble more easily than nucleosomes containing canonical H3 (Conde e Silva et al, (2007)). Therefore, in further embodiments, the nucleosome feature associated with nucleosomes without linker DNA is histone isoform H2Abdb or CENP-A.

The previous aspects of the invention described above, involve binding agents for nucleosomes containing linker DNA. We now describe binding agents for nucleosomes that do not contain linker DNA (i.e. nucleosomes containing approximately 150 bp of DNA or less). Therefore, according to a further aspect of the invention there is provided a binding agent that binds solely or preferentially to features of nucleosomes containing short DNA fragments without linker DNA. There are at least 3 types of such binding agents including (i) binders of "clipped histones", (ii) binders of the core histone isoform H2AZ, and (iii) binders specifically engineered to preferentially bind to nucleosomes containing short DNA fragments without linker DNA.

Therefore, according to a further aspect of the invention, there is provided a method for separating circulating cell free nucleosomes which do not comprise linker DNA from a biological fluid sample, wherein said method comprises the steps of:

(i) contacting the sample with a binding agent which binds to a clipped histone molecule (i.e. from which all or part of the histone tail is absent); and (ii) isolating nucleosomes from the sample which are bound to the binding agent in step (i).

In addition to globular domains, the core histones H2A, H2B, H3 and H4 contain histone tails which protrude outside the nucleosome. The histone tails may undergo a variety of post-translational modifications (PTMs) including methylation, acetylation, propionylation, butylation, crotonylation, 2-hydroxyisobutylation, malonylation, succinylation, formylation, ubiquitination, citrullination, phosphorylation, O-GlcNAcylation, and ADP ribosylation. Diverse histone modifications within the chromatin act in a coordinated fashion to regulate gene transcription. Chemical PTM of a histone typically occurs by selective enzymatic addition or elimination of histone modifications by histone-modifying enzymes. However, multiple pre-existing PTMs may also simultaneously be physically and irreversibly removed by the regulated proteolysis, or clipping, of the histone tail. On histone H3, clipping is reported to occur around amino acid position 21 (Yi and Kim, 2018).

The term "clipped histone" as used herein refers to a histone molecule in which all, or a portion of, a histone tail has been removed. Nucleosomes retain their globular structure when histone tails are removed, but histone clipping within a nucleosome makes the associated DNA increasingly susceptible to degradation by nuclease enzymes (Dhaenens et al, 2014). Binders of clipped nucleosomes can therefore be used as a means to bind to nucleosomes that do not contain linker DNA.

Therefore, according to a further aspect of the invention, there is provided a method for isolating cell free nucleosomes from a biological fluid sample (e.g. by affinity purification), wherein said method comprises the steps of:

(i) contacting the sample with a binding agent which binds to nucleosomes comprising a histone molecule from which all, or a portion of, a histone tail has been removed; and (ii) isolating nucleosomes from the sample which are not bound to the binding agent in step (i).

This aspect of the invention may be used to separate nucleosomes with linker DNA (i.e. unbound nucleosomes) from nucleosomes without linker DNA (i.e. clipped histones bound by the binding agent).

In one embodiment, there is provided a method for isolating circulating cell free nucleosomes of disease or fetal origin from a biological fluid sample by affinity purification, wherein said method comprises the steps of:

(i) contacting the sample with a binding agent which binds to nucleosomes comprising a histone molecule from which all, or a portion of, a histone tail has been removed; and (ii) isolating nucleosomes from the sample which are bound to the binding agent in step (i).

In one embodiment, the nucleosome containing a clipped histone molecule comprises less than 155 base pairs of DNA. In a further embodiment, the nucleosome containing a clipped histone molecule comprises less than 150 base pairs, such as less than 148 base pairs of DNA or less than 147 base pairs of DNA.

In one embodiment, the binding agent binds to a clipped histone H3 protein. In a further embodiment, the binding agent binds to histone H3 at an epitope after amino acid residue 30, i.e. an epitope at amino acid residues 30-33.

Alternatively, a binding agent that binds to the histone tail may be used in a negative selection method for detecting/ isolating clipped histones. Therefore, according to a further aspect of the invention, there is provided a method for isolating cell free nucleosomes from a biological fluid sample (e.g. by affinity purification), wherein said method comprises the steps of:

(i) contacting the sample with a binding agent which binds to a histone tail of a nucleosome; and (ii) isolating nucleosomes from the sample which are not bound to the binding agent in step (i).

This aspect of the invention may be used to separate nucleosomes without linker DNA (i.e. unbound nucleosomes) from nucleosomes with linker DNA (nucleosomes comprising a histone tail which are bound by the binding agent).

In one embodiment, the binding agent binds to a histone tail of histone H3. In a further embodiment, the binding agent binds to histone H3 at an epitope before amino acid residue 30, e.g. an epitope at amino acid residues 4-8.

The histone isoform H2AZ is associated with nucleosome instability and reduced protection of nucleosome associated DNA from nuclease activity. Nucleosomes incorporating the histone isoform H2AZ2.2 are particularly vulnerable to DNA digestion (Bonisch et al, 2012), Binders of histone H2AZ can therefore be used as a means to bind to nucleosomes that contain short DNA fragments of less than approximately 150 bp in length and no linker DNA. Thus, in one embodiment, the binding agent binds to histone H2AZ. In a preferred embodiment the H2AZ molecule is H2AZ2.2.

Therefore, according to a further aspect of the invention, there is provided a method for separating cell free nucleosomes with linker DNA from cell free nucleosomes without linker DNA from a biological fluid sample by affinity purification, wherein said method comprises the steps of:

(i) contacting the sample with a binding agent which binds to nucleosomes comprising a histone H2AZ molecule; and (ii) isolating nucleosomes from the sample which are not bound to the binding agent in step (i).

In one embodiment, there is provided a method for isolating circulating cell free nucleosomes of disease or fetal origin from a biological fluid sample by affinity purification, wherein said method comprises the steps of:

(i) contacting the sample with a binding agent which binds to nucleosomes comprising a histone H2AZ molecule; and (ii) isolating nucleosomes from the sample which are bound to the binding agent in step (i).

Binders may be specifically engineered to bind to nucleosomes containing short DNA fragments without linker DNA whilst not binding, or binding weakly, to nucleosomes (or chromatosomes) including linker DNA. Such binding agents can be used for enriching a biological sample for tumour associated nucleosomes or fetal nucleosomes by isolation of bound nucleosomes without linker DNA. Similarly, binders may be specifically engineered to bind to nucleosomes containing linker DNA whilst not binding, or binding weakly, to nucleosomes containing short DNA fragments without linker DNA. Such binding agents can be also used for enriching a biological sample for tumour associated nucleosomes or fetal nucleosomes by isolation of unbound nucleosomes without linker DNA. In a preferred embodiment, an antibody binder is engineered by a library selection method involving positive and negative selection, for example by phage display library antibody development. Positive selection is performed by exposing the phage antibody library to nucleosomes with no linker DNA (for example synthetic nucleosomes assembled from core histone proteins and 145 bp fragments of DNA). Any antibodies that bind strongly to nucleosomes with no linker DNA are selected as candidates in this first step. Phages expressing positive antibodies are then subjected to a second negative selection step in which they are exposed to nucleosomes containing linker DNA (for example synthetic nucleosomes assembled from core histone proteins and approximately 167 bp or 187 bp fragments of DNA). Any antibodies that bind to nucleosomes containing linker DNA are rejected in this second step. Remaining antibodies that bind to nucleosomes without linker DNA but not to nucleosomes containing linker DNA are selected as suitable antibody binders for use in the invention. Such antibodies may be directed to bind to nucleosome epitopes that exist only in nucleosomes without linker DNA due to conformational structures specific to these nucleosomes and/or nucleosome epitopes unavailable for binding in the presence of linker DNA (e.g. for steric reasons) but unmasked in nucleosomes where the linker DNA is absent.

According to a further aspect of the invention, there is provided a method for separating cell free nucleosomes with linker DNA from cell free nucleosomes without linker DNA from a biological fluid sample by affinity purification, wherein said method comprises the steps of:
(i) contacting the sample with a binding agent engineered to selectively bind to nucleosomes comprising less than about 150 base pairs of DNA in length, wherein the binding agent binds to a nucleosome feature associated with nucleosomes without linker DNA; and
(ii) isolating nucleosomes from the sample which are not bound to the binding agent in step (i).

In one embodiment, there is provided a method for isolating circulating cell free nucleosomes of disease or fetal origin from a blood, serum or plasma sample by affinity purification, wherein said method comprises the steps of:
(i) contacting the sample with a binding agent engineered to selectively bind to nucleosomes comprising less than about 150 base pairs of DNA in length, wherein the binding agent binds to a nucleosome feature associated with nucleosomes without linker DNA; and
(ii) isolating nucleosomes from the sample which are bound to the binding agent in step (i).

In one embodiment, the nucleosomes comprise about 147 base pairs of DNA in length, such as about 145 base pairs of DNA in length.

Binding Agents

It will be clear to persons skilled in the art that any binding agent capable of specific binding to the required target may be used for the methods of the invention. Such binding agents may include, without limitation, antibodies, affimers, aptamers or binding proteins (e.g. nucleosome binding proteins). In one embodiment, the binding agent is selected from an antibody (or fragment thereof), an affimer or an aptamer, in particular an antibody.

In some embodiments, histone H1, macroH2A or chromatin binding proteins (which preferentially binds to linker DNA) themselves are used as a binding agent in a method of the invention. The inventors have surprisingly found that such proteins may be used directly as binding agents. Without being bound by theory, these alternative binding proteins are especially surprising in light of the fact that previously it was understood that histone H1 would bind to linker DNA (i.e. the same region as the chromatin binding proteins described herein) and therefore it was unexpected that alternative binding agents may be used. Furthermore, the methods of the invention may be used to isolate different nucleosome types from the sample by binding to nucleosomes with different epigenetic markers.

It will be understood that combinations of binding agents may be used in the methods of the invention, i.e. to prepare a panel of binding agents to enrich for nucleosomes of different types. Therefore, in one embodiment, the sample is contacted with more than one type of binding agent which binds to nucleosomes comprising linker DNA.

Nucleosome and DNA Analysis

The nucleosomes and/or associated DNA isolated by methods of the invention may be analysed by immunoassay, mass spectroscopy, DNA sequencing (i.e. analysing the associated DNA for a particular genetic sequence or methylated genetic sequence), epigenetic signal structures or other characteristics.

Once the nucleosome fraction (in particular the nucleosome fraction enriched for disease (e.g. tumour) origin) has been isolated, the nucleosome associated DNA may be analysed, e.g. for genetic or DNA sequence markers. Therefore, in one embodiment, the method comprises:
(i) isolating (i.e. enriching) nucleosomes of disease origin using a method as defined herein; and
(ii) analysing the DNA associated with the nucleosomes isolated in step (i).

In a preferred embodiment, a blood plasma sample is collected from a subject with suspected or diagnosed cancer. Nucleosomes without linker DNA in the plasma sample are isolated or enriched by a method as described herein. The DNA associated with the nucleosomes enriched for tumour origin is extracted to produce a size-selected DNA fragment library of approximately less than 150 bp in length. The DNA is analysed for cancer associated mutation abnormalities and/or mutant allele fraction and/or gene methylation abnormalities.

Any DNA analysis method may be employed including, without limitation, DNA sequencing including Next Generation Sequencing (targeted or whole genome) and methylated DNA sequencing analysis, BEAMing, PCR including digital PCR and cold PCR (co-amplification at lower denaturation temperature-PCR), isothermal amplification, hybridization, MIDI-Activated Pyrophosphorolysis (MAP) or Personalized Analysis of Re-arranged Ends (PARE).

DNA analysis may include analysis for any genetic DNA markers including nucleotide substitutions, nucleotide insertions, nucleotide deletions, methylated DNA sequences or other DNA sequence mutations. Typical cancer associated DNA abnormalities that may be investigated in such an analysis include, without limitation, point mutations, translocations, gene copy number mutations, microsatellite abnormalities, DNA strand integrity and gene methylation status.

A large number of genes have been found to be mutated in cancer patients generally but any particular mutation is likely to occur in only a small proportion of cancer patients. However, all cancers patients do have some mutations, so the probability of detecting at least one mutation in any particular patient increases with the number of potential mutations tested. For this reason, it is usual to test for a panel of genetic mutations. Such a panel might, without limitation, include one or more mutations in the ABL1, ACVR1, ACVR1B, ACVR2A, AJUBA, AKT1, AKT2, AKT3, ALB, ALK, AMER1, APC, APEX1, APLNR, APOB, AR, ARAF, ARHGAP35, ARID1A, ARID2, ARIDSB, ATF7IP, ATM, ATP11B, ATR, ATRX, ATXN3, AURKA, AXIN1, AXIN2, B2M, BAP1, BCL2, BCL2L1, BCL2L11, BCL9, BOOR, BIRC2, BIRC3, BRAF, BRCA1, BRCA2, BRD7, BTG2, BTK, CARD11, CASP8, CBL, CCND1, CCND2, CCND3, CCNE1, CD44, CD70, CD79B, CDH1, CHD3, CHD8, CDK12, CDK2, CDK4, CDK6, CDKN2A, CDKN2B, CEBPA, CHD4, CHEK2, COL5A1, CREBBP, CSF1R, CSNK2A1, CTNNB1, CTNND1, CUL1, CUL3, CYP2C19, CYP2D6, DACH1, DCUN1D1, DDR2, DICER1, DNMT3A, DPYD, EEF2, EGFR, ELF3, EP300, EPHA2, EPHA3, EPHA5, ERBB2, ERBB3, ERBB4, ERCC2, ESR1, EZH2, FANCA, FANCC, FANCD2, FANCE, FANCF, FANCI, FANCL, FAS, FAT1, FBXW7, FGF3, FGFR1, FGFR2, FGFR3, FGFR4, FLCN, FLT1, FLT3, FLT4, FOXA1, FOXA2, FOXQ1, GAS6-AS1, GATA1, GATA2, GATA3, GATA6, GNA11, GNAQ, GNAS, H3F3A, H3F3C, HGF, HIST1H3B, HNF1A, HRAS, IDH1, IDH2, IGF1R, IL6, IL6ST, IL7R, INSR, JAK1, JAK2, JAK3, KDM6A, KDR, KEAP1, KIT, KNSTRN, KRAS, KMT2A, KMT2B, KMT2C, KMT2D, LYN, MAGOH, MAP2K1, MAP2K2, MAP2K4, MAP3K1, MAP3K4, MAPK1, MDM2, MDM4, MECOM, MED12, MEN1, MET, MGA, MLH1, MPL, MRE11A, MSH2, MSH3, MSH6, MTOR, MUC6, MYC, MYCL, MYCN, MYD88, MYO18A, NCOR1, NF1, NF2, NFE2L2, NKX2-1, NKX2-8, NOTCH1, NOTCH2, NOTCH3, NPM1, NRAS, NSD1, NTRK1, NTRK2, NTRK3, NUP133, NUP93, PALB2, PAX5, PBRM1, PD-1, PDGFRA, PDGFRB, PD-L1, PD-L2, PIK3CA, PIK3CB, PIK3CG, PIK3R1, PIK3R2, PIM1, POLD1, POLE, PPP2R1A, PPP6C, PRKAR1A, PRKCI, PRKDC, PSIP1, PMS2, PTCH1, PTEN, PTMA, PTPDC1, PTPN11, PTPRC, PTPRD, RAC1, RAD21, RAD50, RAD51, RAD51B, RAD51C, RAD51D, RAF1, RARA, RASA1, RB1, RBM10, RET, RFC1, RHEB, RHOA, RHOB, RICTOR, RNF43, ROS1, RPS6KA3, RPS6KB1, RPTOR, RQCD1, RRAS2, RUNX1, RUNX1T1, RXRA, SCAF4, SETBP1, SETD2, SF1, SF3B1, SIN3A, SLX4, SMAD2, SMAD4, SMARCA1, SMARCA4, SMARCB1, SMC1A, SMC3, SMO, SOS1, SOX17, SOX2, SOX9, SPOP, SPTA1, SPTAN1, SRC, SRSF2, STAG2, STAT3, STK11, TAF1, TBL1XR1, TBX3, TCEB1, TCF12, TCF7L2, TET2, TGFBR2, TGIF1, THRAP3, TLR4, TMSB4X, TNFAIP3, TOP1, TOP2A, TP53, TPMT, TRAF3, TSC1, TSC2, TSHR, TXNIP, U2AF1, UGT1A1, UNCX, USP9X, VHL, WHSC1, WT1 XPO1 and ZFHX3 genes.

Similarly, many genes have been investigated as markers for differential cytosine methylation status in cancer. A few of these are SEPTIN-9, APC, DAPK, GSTP1, MGMT, p16, RASSF1A, TIG1, BRCA1, ERα, PRB, TMS1, MLH1, HLTF, CDKN2A, SOCS1, SOCS2, PAX5, PGR, PTGS2 and RARβ2.

Furthermore, according to another aspect of the invention, there is provided a method for isolating purified circulating tumour DNA (ctDNA) from a biological fluid sample, wherein said method comprises the steps of:
    (i) performing the method as defined herein; and
    (ii) analysing the DNA from the isolated nucleosomes.

This aspect of the invention finds particular use in analysing nucleosomes without linker DNA (i.e. isolated in the second aspect of the invention) because such nucleosomes are predicted to be of disease origin. Optionally, the DNA associated with the isolated nucleosomes is extracted prior to analysis. Many methods of analysis of extracted DNA are known in the art. Alternatively, the DNA is directly analysed, i.e. without requiring extraction.

If the cell free nucleosomes isolated are of tumour origin, the level of isolated tumour nucleosomes detected as a proportion of nucleosomes present in the original (untreated) sample may be used as an indicator of the proportion of DNA that comprises circulating tumour DNA (ctDNA) in a sample. Furthermore, the converse level is the proportion of DNA of healthy origin in the sample. Therefore, the methods described herein may be used to detect the level/proportion of ctDNA in a sample or changes to such levels over time. Such a measure is similar to mutant allele fraction measures of cancer associated mutations in ctDNA and may be used as a measure of tumour burden and response to therapy.

Nucleosomes which have been enriched for disease (e.g. tumour) origin may also be analysed for epigenetic markers ("epigenetic epitopes") or subjected to further enrichment methods. Therefore, in one embodiment, the method comprises:
    (i) isolating (i.e. enriching) cell free nucleosomes of disease origin by a method as defined herein;
    (ii) analysing the cell free nucleosomes isolated in step (ii)

In one embodiment, the analysing step comprises analysing the isolated cell free nucleosome for epigenetic nucleosome features that are selected from: histone type (for example, H1, H2A, H2B, H3, H4 histones), histone post-translational modifications, histone isoforms, particular nucleotides, modified nucleotides (for example methylated, hydroxyl-methylated or other nucleotide modifications), or combinations thereof or for the presence of other proteins adducted to the nucleosome.

The presence or level of enriched cell free nucleosomes of disease origin containing a modified nucleotide, histone post-translational modification, histone isoform or nucleosome-protein adduct detected may be used as an indicator of disease status, disease prognosis, disease monitoring, treatment monitoring, minimal residual disease or disease susceptibility to particular treatments or for other clinical applications.

The analysis of the isolated nucleosomes of disease origin may involve any suitable method of analysis of which many are known in the art. These methods include without limitation analysis by immunoassay using an antibody or other binder to a common nucleosome epitope such as DNA or to an epigenetic structure of interest including a histone modification, histone variant, DNA modification or another molecule adducted to a nucleosome. These methods include all the methods described in WO 2005/019826, WO 2013/030577, WO 2013/030579 and WO 2013/084002, which are incorporated herein by reference. Without limitation, any of these methods may be employed in combination with the present invention. These methods also include multiplex methods for the analysis of multiple epitopes present in circulating nucleosomes of disease origin.

The analysis of nucleosomes of disease origin isolated by a method of the invention may also involve any proteomics method known in the art including, without limitation, electrophoresis methods, chromatographic methods and any method involving mass spectrometry including methods involving chromatography and mass spectrometry and/or stable isotope labelled mass spectrometry and/or methods involving protein digestion to produce peptides for identification and/or quantification by mass spectrometry or any combinatorial mass spectrometry method with any other method.

In one embodiment, the epitope is selected from a histone modification (e.g. a histone post-translational modification [PTM]), a modified nucleotide, a histone variant or isoform, or a nucleosome adduct or variant thereof. In a further embodiment, the modified nucleotide comprises 5-methyl-cytosine.

A variety of epigenetically modified nucleotides have been described in the literature and epigenetic modification patterns in DNA and/or DNA nucleotide residues are known to be altered in cancer. The best described of these includes methylation of cytosine at position 5, i.e. "5-methylcyto-sine". DNA containing 5-methylcytosine is often referred to as "methylated DNA". The methylation of DNA in cancer cells is estimated to be reduced by approximately 50% compared to the DNA of healthy cells (Guerrero-Preston et al, 2007; Soares et al, 1999). However, the cancer associated increase in the level of circulating nucleosomes can be several-fold (Holdenrieder et al, 2001 and Schwarzenbach et al, 2011).

Assays for further epigenetic epitopes may be performed in isolation or as part of an assay panel.

In one embodiment, the isolated nucleosome sample obtained from the methods described herein are subject to further enrichment steps. Therefore, in one embodiment, a method of the invention additionally comprises contacting the isolated nucleosomes with a histone H3.1 and/or H3.2 and/or H3t binding agent. It has previously been shown that the histone 3 isoforms, H3.1, H3.2 and H3t, may be used for ctDNA enrichment.

Methods of Obtaining Binding Agents

The difference in nucleosome associated DNA fragment size as described herein may be utilised to design and obtain binding agents for use in the invention. One method for obtaining binders or antibodies that preferentially bind to short, e.g. less than 150 bp DNA, nucleosomes is to use a recombinant or synthetic nucleosome containing approximately 147 bp of DNA as an antigen against which to raise an antibody. In a preferred aspect of this method, antibodies or binders that bind short DNA nucleosomes are also tested for binding to longer approximately 167 bp DNA nucleosomes for negative selection purposes. By this method, antibodies that bind to short DNA nucleosomes but not to long DNA nucleosomes can be selected and produced as a reagent for enrichment or purification of short DNA nucleosomes.

According to a further aspect of the invention, there is provided a method for obtaining an antibody or other binding agent that preferentially binds to cell free nucleosomes of disease origin, wherein said method comprises the steps of:

(i) using a nucleosome containing approximately 150 base pairs or less of DNA as an antigen against which to produce an antibody or other binding agent;

(ii) presenting the antibody or other binding agent obtained in step (i) to a nucleosome containing approximately 165 base pairs or more of DNA; and (iii) selecting the antibody or other binding agent that binds to the nucleosome of step (i), but not (or only binds weakly) to the nucleosome of step (ii).

According to a further aspect of the invention, there is provided a method for obtaining an antibody or other binding agent that preferentially binds to cell free nucleosomes of non-disease origin, wherein said method comprises the steps of:

(i) using a nucleosome containing approximately 165 base pairs or more of DNA as an antigen against which to produce an antibody or other binding agent;

(ii) presenting the antibody or other binding agent obtained in step (i) to a nucleosome containing approximately 150 base pairs or less of DNA; and (iii) selecting the antibody or other binding agent that binds to the nucleosome of step (i), but not (or only binds weakly) to the nucleosome of step (ii).

In one embodiment, the nucleosome used as an antigen is a recombinant or synthetic nucleosome. Nucleosomes for use in generating or testing binders of short nucleosomes may contain approximately 150 base pairs or less, such as 147 base pairs or less, or 145 base pairs or less. Nucleosomes (or oligonucleosomes or other chromatin fragments) for use in generating or testing binders of nucleosomes containing linker DNA may contain approximately 155 base pairs or more, such as 160 base pairs or more, or 165 base pairs or more, or 167 base pairs or more.

In a preferred embodiment of the method, phage display library antibody selection is used to identify antibodies. For example, a phage display library may be used for positive selection of phage lines that bind short DNA nucleosomes together with negative selection for phage lines that bind long DNA nucleosomes. Therefore, in one embodiment, the method comprises phage display library antibody selection.

According to a further aspect of the invention, there is provided a method for the production of a binder that selectively binds to nucleosomes containing linker DNA whilst not binding, or binding weakly, to nucleosomes containing short DNA fragments (i.e. nucleosomes without linker DNA), wherein said method comprises the steps of:

(i) contacting a binder library with a nucleosome, (ii) isolating binders that bind to nucleosomes comprising more than approximately 165 base pairs of DNA in step (i), (iii) contacting binders isolated in step (ii) with a nucleosome comprising less than approximately 150 base pairs of DNA in length; and (iv) isolating binders that do not bind, or bind weakly, to nucleosomes comprising less than approximately 150 base pairs of DNA in length in step (iii), Therefore, according to a further aspect of the invention, there is provided a method for the production of a binder that selectively binds to nucleosomes containing short DNA fragments (i.e. nucleosomes without linker DNA) whilst not binding, or binding weakly, to nucleosomes comprising linker DNA, wherein said method comprises the steps of:

(i) contacting a binder library with a nucleosome, (ii) isolating binders that bind to nucleosomes comprising less than 150 base pairs of DNA in step (i), (iii) contacting binders isolated in step (ii) with a nucleosome comprising more than 165 base pairs of DNA in length; and (iv) isolating binders that do not bind, or bind weakly, to nucleosomes comprising more than 165 base pairs of DNA in length in step (iii), Methods Using Antibody Binders In further embodiments, the methods described herein may additionally comprise contacting the sample bound in step (i) with a second binding agent which binds to nucleosomes or a component thereof. The method may therefore be used with two binding agents to determine the content of the nucleosomes isolated by the methods described herein.

Antibodies that are selective for binding to nucleosomes containing linker DNA or selective for nucleosomes without linker DNA may be used in immunoassay methods of the invention as a direct measure of such nucleosomes. According to a further aspect of the invention there is provided an immunoassay for the detection or measurement of nucleosomes without linker DNA, wherein said method comprises the steps of:

(i) contacting the sample with an antibody binding agent that binds selectively to nucleosomes without linker DNA;

(ii) contacting the sample bound in step (i) with a second binding agent which binds to nucleosomes or a component thereof; and (iii) detecting or measuring the binding of said second binding agent to the nucleosomes in the sample; and (iv) using the presence or degree of such binding as a measure of cell free nucleosomes without linker DNA in the sample.

According to a further aspect of the invention there is provided an immunoassay for the detection or measurement of nucleosomes containing linker DNA, wherein said method comprises the steps of:

(i) contacting the sample with an antibody binding agent that binds selectively to nucleosomes containing linker DNA;

(ii) contacting the sample bound in step (i) with a second binding agent which binds to nucleosomes or a component thereof; and (iii) detecting or measuring the binding of said second binding agent to the nucleosomes in the sample; and (iv) using the presence or degree of such binding as a measure of cell free nucleosomes containing linker DNA in the sample.

Antibodies that are selective for binding to nucleosomes containing linker DNA or selective for nucleosomes without linker DNA may be also be used in enrichment methods of the invention.

Immunoassay Methods Using Non-Antibody Binders

The inventors have surprisingly found that proteins which bind to nucleosomes can be used directly in isolation and detection methods for cell free nucleosomes. Such methods avoid the need to raise antibodies and can instead utilise natural proteins. Therefore, according to a further aspect, there is provided the use of a binding protein for isolation of cell free nucleosomes from a body fluid sample.

According to a further aspect of the invention, there is provided an immunoassay method of detecting cell free nucleosomes in a biological fluid sample, wherein said method comprises the steps of:

(i) contacting the sample with a first binding agent selected from histone H1, macroH2A, a chromatin binding protein or fragments, analogues or engineered derivatives thereof;

(ii) contacting the sample bound in step (i) with a second binding agent which binds to nucleosomes or a component thereof; and (iii) detecting or measuring the binding of said second binding agent to the nucleosomes in the sample; and (iv) using the presence or degree of such binding as a measure of cell free nucleosomes in the sample.

In an alternative aspect, there is provided an immunoassay method of detecting cell free nucleosomes in a biological fluid sample, wherein said method comprises the steps of:

(i) contacting the sample with a first binding agent which binds to nucleosomes or a component thereof;

(ii) contacting the sample bound in step (i) with a second binding agent selected from histone H1, macroH2A, a chromatin binding protein or fragments, analogues or engineered derivatives thereof; and (iii) detecting or measuring the binding of said second binding agent to the nucleosomes in the sample; and (iv) using the presence or degree of such binding as a measure of cell free nucleosomes in the sample.

In one embodiment, the chromatin binding protein is associated with linker DNA. In a further embodiment, the chromatin binding protein is selected from: MBD, HMGB, CHD, DNMT and PARP.

According to a further aspect, there is provided an immunoassay method of detecting cell free nucleosomes in a biological fluid sample, wherein said method comprises the steps of:

(i) contacting the sample with a first binding agent which binds to nucleosomes or a component thereof;

(ii) contacting the sample bound in step (i) with a second binding agent which binds to a chromatin binding protein selected from: CHD, DNMT, PARP and MBD; and (iii) detecting or measuring the binding of said second binding agent to the chromatin binding agent in the sample; and (iv) using the presence or degree of such binding as a measure of cell free nucleosomes in the sample.

According to a further aspect, there is provided a method of detecting cell free nucleosomes in a biological fluid sample, wherein said method comprises the steps of:

(i) contacting the sample with a first binding agent which binds to a chromatin binding protein selected from: CHD, DNMT, PARP and MBD;

(ii) contacting the sample bound in step (i) with a second binding agent which binds to nucleosomes or a component thereof; and (iii) detecting or measuring the binding of said second binding agent to the nucleosomes in the sample; and (iv) using the presence or degree of such binding as a measure of cell free nucleosomes in the sample.

Circulating Extracellular Vesicles

Blood contains a number of extracellular vesicles (ECV) which contain or are bound to DNA, nucleosomes, and/or other protein-nucleic acid complexes. Exosomes are one example of an ECV that may comprise nucleosomes and/or DNA and/or other chromatin fragments. Nucleosomes associated with exosomes or other ECVs, including nucleosomes containing linker DNA, may be protected from, or less susceptible to, binding to chromatin proteins or other binders and may thus remain unbound when these moieties are used in methods of the invention. Any such ECV associated nucleosomes containing linker DNA that are not bound by proteins using methods as described herein may remain in the supernatant. This effect may be prevented by removal of exosomes and/or other ECVs from the sample.

Therefore, according to a further aspect of the invention, there is provided a method for separating cell free nucleosomes with linker DNA from cell free nucleosomes without linker DNA from a biological fluid sample by affinity purification, wherein said method comprises the steps of:

(i) removing exosomes or other ECVs from the sample;

(ii) contacting the sample with a binding agent that binds to nucleosome associated linker DNA; and (iii) isolating nucleosomes from the sample which are not bound to the binding agent in step (ii).

It will be appreciated by those skilled in the art that steps (i) and (ii) above may be performed in any order or concurrently.

Many binders to ECVs are known in the art and may be used for the purposes of binding and removing ECVs from a sample. Commercial products for the isolation of exosomes and other ECVs from samples are also available. Lectins are proteins that are known to bind to most or all exosomes. Therefore, in one embodiment, exosomes or other ECVs are removed from the sample using lectin. In a preferred embodiment of the invention, lectin proteins are attached to a solid phase support and used to bind to exosomes and other ECVs present in a sample. Following exposure to the lectin protein, the sample supernatant is depleted of exosomes/ECVs and hence of any exosome or ECV associated nucleosomes containing linker DNA.

Therefore, in one embodiment of the invention, there is provided a method for separating cell free nucleosomes with linker DNA from cell free nucleosomes without linker DNA from a biological fluid sample by affinity purification, wherein said method comprises the steps of:

(i) contacting the sample with a lectin moiety;

(ii) contacting the sample with a binding agent that binds to nucleosome associated linker DNA; and (iii) isolating nucleosomes from the sample which are not bound to the binding agent in step (ii).

It will be appreciated by those skilled in the art that steps (i) and (ii) above may be performed in any order or concurrently. In a preferred embodiment the sample is a blood plasma sample.

Methods of Detection and Treatment of Cancer

According to a further aspect of the invention there is provided an assay method for detecting or diagnosing the presence of a disease by measuring or detecting the presence and/or the level of nucleosomes containing little or no linker DNA in a body fluid, and using the detected level as a biomarker (either alone as a member of a panel of tests) of the disease status of a subject including, without limitation, a clinical diagnosis of a disease, a differential diagnosis of disease type or subtype, or a disease prognosis, or a disease relapse, or a diagnosis of subject susceptibility to treatment regimens. It will be appreciated by those skilled in the art that body fluids used for diagnostic testing include without limitation blood, serum, plasma, urine, cerebrospinal fluid and other fluids. In a preferred embodiment the body fluid selected as the sample is blood, serum or plasma. Isolated nucleosomes containing little or no linker DNA in a body fluid may be measured by a variety of methods including mass spectrometry and immunoassay. Alternatively, the nucleosome associated DNA may be measured by physical or chemical methods including, without limitation, chromatography, electrophoresis, PCR and DNA sequencing methods.

The assay response, level, concentration or quantity of nucleosomes containing little or no linker DNA in a body fluid may be expressed in absolute terms or relative terms, for example without limitation as a proportion of the total nucleosome level present or as a ratio to the level of another nucleotide or histone variant or histone PTM or to the level of total DNA. In one embodiment the ratio of nucleosomes in a sample that do, or do not contain linker DNA is used as a marker of cancer. Thus, a high ratio of [nucleosomes without linker DNA]/[nucleosomes with linker DNA] is indicative of cancer. Similarly, a ratio of the amount or concentration of [DNA fragments of length less than 150 bp]/[DNA fragments of length greater than 150 bp] may be determined or the mutant allele fraction may be determined. The cut-off of 150 bp for DNA fragment size is used here as an example. Other cut-offs may be used.

The methods described herein may be used in conjunction with methods of diagnosis. For example, a sample may be enriched to isolate DNA or cell free nucleosomes of tumour origin using the methods described herein and the enriched sample may then be used in a method of diagnosis by detecting further epigenetic markers which are associated with disease.

Therefore, according to a further aspect of the invention, there is provided a method of diagnosing cancer comprising:

(i) performing the method as defined herein to isolate circulating tumour nucleosomes from a biological sample obtained from a patient; and (ii) analysing the isolated circulating tumour nucleosomes and/or associated DNA.

In one embodiment, step (ii) comprises analysing the isolated circulating tumour nucleosomes for epigenetic nucleosome features that are selected from: histone type (for example, H2A, H2B, H3, H4 histone), histone post-translational modifications, histone isoforms, particular nucleotides or modified nucleotides (for example methylated, hydroxyl-methylated or other nucleotide modifications), proteins adducted to the nucleosome or combinations thereof.

In one embodiment, the associated DNA is analysed using DNA sequencing, for example a sequencing method selected from Next Generation Sequencing (targeted or whole genome) and methylated DNA sequencing analysis, BEAMing, PCR including digital PCR and cold PCR (co-amplification at lower denaturation temperature-PCR), isothermal amplification, hybridization, MIDI-Activated Pyrophosphorolysis (MAP) or Personalized Analysis of Re-arranged Ends (PARE).

According to a further aspect of the invention, there is provided a method of diagnosing or detecting cancer in an animal or a human subject which comprises the steps of:

(i) performing a method as defined herein;

(ii) contacting the isolated nucleosomes of tumour origin obtained in step (i) with a further binding agent which binds to an epigenetic epitope of tumour derived nucleosomes (the "biomarker");

(iii) detecting and/or quantifying the binding of said further binding agent to said epitope; and (iv) using the measured level of said epitope as indicative of the presence of cancer in the subject.

Detecting and/or quantifying may be performed directly on the purified or enriched nucleosome sample, or indirectly on an extract therefrom, or on a dilution thereof. Quantifying the amount of the biomarker present in a sample may include determining the concentration of the biomarker present in the sample. Uses and methods of detecting, monitoring and of diagnosis according to the invention described herein are useful to confirm the existence of a disease, to monitor development of the disease by assessing onset and progression, or to assess amelioration or regression of the disease. Uses and methods of detecting, monitoring and of diagnosis are also useful in methods for assessment of clinical screening, prognosis, choice of therapy, evaluation of therapeutic benefit, i.e. for drug screening and drug development.

The methods of diagnosis described herein may further comprise comparing the level of the second binding agent present in the biological sample with one or more control(s). In one embodiment, the biological sample from the one or more control(s) is taken from healthy (or "normal") patient (s) and/or patient(s) with an associated benign disease. In a further embodiment, the biological sample from the one or more control(s) is taken from healthy patient(s).

According to a further aspect of the invention, there is provided a method of diagnosing cancer, which comprises the steps of:

(a) measuring the level of nucleosomes without linker DNA in a body fluid sample obtained from a subject by a method of the invention; and (b) using the level of the nucleosomes measured in step (a) to determine if the patient has cancer.

According to a further aspect of the invention, there is provided a method of diagnosing cancer, which comprises the steps of:

(a) measuring the ratio of nucleosomes without linker DNA and nucleosomes with linker DNA in a body fluid sample obtained from a subject by a method of the invention; and (b) using the ratio measured in step (a) to determine if the patient has cancer.

In one aspect of the invention, the methods described herein may be used to monitor a patient for progression of relapse of cancer. In another aspect, the methods described herein may be used to select a suitable therapy for the patient. For example, analysing the DNA associated with the isolated nucleosomes can determine the genotype of the cancer of the patient which may make them more or less responsive to a particular therapy. In one aspect of the invention, the methods described herein may be used to monitor minimal residual disease (MRD), i.e. identify the presence of residual malignant cells in a patient who has been treated. The detection of MRD indicates that treatment is incomplete.

According to a further aspect of the invention, there is provided a method of treating cancer, which comprises the steps of:

(a) obtaining a sample from a patient;

(b) measuring the level of nucleosomes containing short DNA fragments of approximately less than 150 bp in length in the sample by a method of the invention;

(c) using the level of the nucleosomes measured in step (b) to determine if the patient has cancer; and (d) administering a treatment if the patient is determined to have cancer in step (c).

According to a further aspect of the invention, there is provided a method of treating cancer, which comprises the steps of:

(a) obtaining a sample from a patient;

(b) measuring the ratio of nucleosomes containing short and long DNA fragments of approximately less than 150 bp and more than 150 bp in length in the sample by a method of the invention;

(c) using the ratio of the nucleosomes measured in step (b) to determine if the patient has cancer; and (d) administering a treatment if the patient is determined to have cancer in step (c).

In one embodiment, the method of the invention is used to measure the level of nucleosomes containing short or long DNA fragments (i.e. of approximately less than 150 bp and more than 150 bp in length, respectively) in a sample is an immunoassay method of the invention as described herein.

According to a further aspect of the invention, there is provided a method of treating cancer, which comprises the steps of:

(a) obtaining a sample from a patient;

(b) isolating DNA fragments of approximately 150 bp or less in the sample by a method of the invention;

(c) using the level of DNA fragments isolated in step (b) to determine if the patient has cancer; and (d) administering a treatment if the patient is determined to have cancer in step (c).

An important aspect of the method of the invention is the facilitation of improved detection and treatment of cancer diseases through improved methods for ctDNA detection and analysis. Four of the five approaches to ctDNA analysis, outlined earlier in the background of the invention, require sequencing of the DNA fragments and/or sequencing of methylated DNA fragments. However, these methods struggle due to the low levels of ctDNA in the analysed samples.

In one embodiment, step (c) comprises determining the mutant allele fraction of the DNA fragments. In a further or alternative embodiment, step (c) comprises sequencing the DNA fragments. The nucleotide sequence may then be used to determine if a patient has cancer, e.g. analysing for any genetic DNA markers including nucleotide substitutions, nucleotide insertions, nucleotide deletions, methylated DNA sequences or other DNA sequence mutations, as described hereinbefore.

In one embodiment, the treatment administered is selected from: surgery, radiotherapy, chemotherapy, immunotherapy, hormone therapy and biological therapy.

Kits

According to a further aspect of the invention, there is provided a kit for detecting or isolating or measuring nucleosomes which comprises: (i) histone H1, macroH2A or a chromatin binding protein and (ii) a binding agent which specifically binds to nucleosomes or a component thereof, optionally together with instructions for use of the kit in accordance with the method as defined herein.

According to a further aspect of the invention, there is provided a kit for detecting or isolating or measuring nucleosomes which comprises: (i) an antibody or other binder directed to bind to a chromatin binding protein and (ii) a binding agent which specifically binds to nucleosomes or a component thereof, optionally together with instructions for use of the kit in accordance with the method as defined herein.

Kits of the invention may alternatively, or additionally, include reagents for the isolation and/or analysis of nucleosome associated DNA fragments. According to a further aspect of the invention, there is provided a kit which comprises: (i) histone H1, macroH2A or a chromatin binding protein; and (ii) reagents for the isolation and/or analysis of nucleosome associated DNA fragments, optionally together with instructions for use of the kit in accordance with the method as defined herein.

According to a further aspect, there is provided the use of a kit as defined herein for the diagnosis of cancer.

General Features of the Invention

The following embodiments may be applied to the aspects of the invention described herein.

In one embodiment, the nucleosome is a cell free mononucleosome or oligonucleosome. It will be clear that the term "nucleosome" as used herein is intended to include mononucleosomes and oligonucleosomes and any such chromatin fragments that can be analysed in fluid media. In a further embodiment, the cell-free nucleosome is a mononucleosome, oligonucleosome or other chromosome fragment.

In one embodiment, the biological fluid (i.e. body fluid) sample is selected from a blood, serum or plasma sample.

In one embodiment, a biological fluid sample is obtained from a subject and cell free nucleosomes in the sample are enriched for disease associated or disease derived nucleosomes as described herein. The fluid sample may be any biological fluid (or body fluid) sample taken from a subject including, without limitation, cerebrospinal fluid (CSF), whole blood, blood serum, plasma, menstrual blood, endometrial fluid, urine, saliva, or other bodily fluid (stool, tear fluid, synovial fluid, sputum), breath, e.g. as condensed breath, or an extract or purification therefrom, or dilution thereof. Biological samples also include specimens from a live subject, or taken post-mortem. The samples can be prepared, for example where appropriate diluted or concentrated, and stored in the usual manner. In a particular embodiment, the body fluid is selected from blood, serum and plasma.

Methods of collection of biological samples are well known in the art and it will be understood that any such methods of collection are suitable for use with the methods described herein.

In one embodiment, the subject is a human or an animal, such as a human, a horse, a dog or a mouse. References to "subject" or "patient" are used interchangeably herein.

Immunoassay methods described herein refer to anti-nucleosome antibodies or binders or to antibodies or other binders that bind to an epitope present in a nucleosome. It will be clear to those skilled in the art that such binders may be directed to bind to any epitope present in a nucleosome or chromatin fragment. Such epitopes include, without limitation, histone proteins (in particular core histone proteins), histone isoforms, modified histones (e.g. histone post-translational modifications), DNA associated with nucleosomes (e.g. nucleotides, modified nucleotides), conformational epitopes or histone adducts (i.e. proteins adducted to a nucleosome).

In a preferred embodiment the binding agent is coated on a solid support, such as sepharose, sephadex, plastic or magnetic beads. In one embodiment, said solid support comprises a porous material. In another embodiment the binding agent is derivatised to include a tag or linker which can be used to attach the binding agent to a suitable support which has been derivatised to bind to the tag. Many such tags and supports are known in the art (e.g. Sortag, Click Chemistry, biotin/streptavidin, his-tag/nickel or cobalt, GST-tag/GSH, antibody/epitope tags and many more). For ease of use, the coated support may be included within a device, for example a microfluidic device.

In one embodiment, the disease (from which the isolated, circulating, cell free nucleosomes originate) is selected from cancer, an autoimmune disease or inflammatory disease. In a further embodiment, the disease is cancer. In a further embodiment, the autoimmune disease is selected from: Systemic Lupus Erythematosus (SLE) and rheumatoid arthritis. In a further embodiment, the inflammatory disease is selected from: Crohn's disease, colitis, endometriosis and Chronic Obstructive Pulmonary Disorder (COPD).

If the disease is cancer, then the isolated nucleosomes may be referred to as "tumour derived" or "tumour associated" nucleosomes. As ctDNA and circulating nucleosomes are a feature of all cancer disease types investigated, the methods of the invention are suitable for use in all cancer diseases. In one embodiment, the tumour derived or tumour associated cell free nucleosomes originate from a cancer selected from: breast cancer, bladder cancer, colorectal cancer, skin cancer (such as melanoma), ovarian cancer, prostate cancer, lung cancer, pancreatic cancer, bowel cancer, liver cancer, endometrial cancer, lymphoma, oral cancer, head and neck cancer, leukaemia and osteosarcoma.

The disclosure provides ligands or binders, such as naturally occurring or chemically synthesised compounds, capable of specific binding to nucleosomes. A ligand or binder may comprise a peptide, an antibody or a fragment thereof, or a synthetic ligand such as a plastic antibody, or an aptamer, or an affimer or oligonucleotide, capable of specific binding to the nucleosome. The antibody can be a monoclonal antibody or a fragment thereof capable of specific binding to the nucleosome. A ligand or binder (for example a chromatin binding agent as described herein, or a binding agent directed towards the nucleosome or a component thereof) may be labelled with a detectable marker, such as a luminescent, fluorescent, enzyme or radioactive marker. Alternatively, or additionally, a ligand may be labelled with an affinity tag, e.g. a biotin, avidin, streptavidin or His (e.g. hexa-His) tag. Alternatively, ligand binding may be determined using a label-free technology for example that of ForteBio Inc.

The methods described herein isolate nucleosomes using particular targets. Said isolated nucleosomes may then be further analysed for particular biomarkers. The term "biomarker" means a distinctive biological or biologically derived indicator of a process, event, or condition. Biomarkers can be used in methods of diagnosis, e.g. clinical screening, and prognosis assessment and in monitoring the results of therapy, identifying subjects most likely to respond to a particular therapeutic treatment, drug screening and development. Such biomarkers include, for example, the level of cell free nucleosomes per se (i.e. the level of nucleosomes isolated by a method of the invention) or the level of epigenetic features of the isolated cell free nucleosomes. Diagnostic or monitoring kits are provided for performing methods of the invention. Such kits will suitably comprise a ligand for detection and/or quantification of the target or biomarker, and/or a biosensor, and/or an array as described herein, optionally together with instructions for use of the kit. A further aspect of the invention is a kit for detecting the presence of a disease state, comprising a biosensor capable of detecting and/or quantifying one or more of the biomarkers as defined herein.

The terms "detecting" and "diagnosing" as used herein encompass identification, confirmation, and/or characterisation of a disease state. Methods of detecting, monitoring and of diagnosis according to the invention are useful to confirm the existence of a disease, to monitor development of the disease by assessing onset and progression, or to assess amelioration or regression of the disease. Methods of detecting, monitoring and of diagnosis are also useful in methods for assessment of clinical screening, prognosis, choice of therapy, evaluation of therapeutic benefit, i.e. for drug screening and drug development.

Efficient diagnosis and monitoring methods provide very powerful "patient solutions" with the potential for improved prognosis, by establishing the correct diagnosis, allowing rapid identification of the most appropriate treatment (thus lessening unnecessary exposure to harmful drug side effects), and reducing relapse rates.

It is known that increased cell turnover, cell death and apoptosis lead to increased circulatory levels of cell free nucleosomes (Holdenrieder et al, 2001). Circulating cell free nucleosomes level is a non-specific indicator and occurs in a variety of conditions including inflammatory diseases, a large variety of benign and malignant conditions, autoimmune diseases, as well as following trauma or ischaemia (Holdenrieder et al 2001). It will be clear to those skilled in the art that the invention will have application in a variety of disease areas where circulating nucleosomes have been found in subjects. These include, without limitation, trauma (for example; severe injury or surgery), extreme exercise (for example running a marathon), stroke and heart attack, sepsis or other serious infection and endometriosis.

The immunoassays of the invention include immunometric assays employing enzyme detection methods (for example ELISA), fluorescence labelled immunometric assays, time-resolved fluorescence labelled immunometric assays, chemiluminescent immunometric assays, immunoturbidimetric assays, particulate labelled immunometric assays and immunoradiometric assays and competitive immunoassay methods including labelled antigen and labelled antibody competitive immunoassay methods with a variety of label types including radioactive, enzyme, fluorescent, time-resolved fluorescent and particulate labels. All of said immunoassay methods are well known in the art, see for example Salgame et al, 1997 and van Nieuwenhuijze et al, 2003.

Any DNA physical or chemical analysis method may be employed for methods of the invention including methods to measure DNA fragment length (e.g. chromatography or electrophoresis). Any physical or chemical method may also be employed for further DNA analysis such as that described by Sina et al, 2018. Similarly, any DNA sequencing method may be employed including Next Generation Sequencing (targeted or whole genome) and methylated DNA sequencing analysis, BEAMing, PCR including digital PCR and cold PCR (co-amplification at lower denaturation temperature-PCR), isothermal amplification, hybridization, MIDI-Activated Pyrophosphorolysis (MAP) or Personalized Analysis of Re-arranged Ends (PARE).

DNA analysis may include analysis for any genetic DNA markers including nucleotide substitutions, nucleotide insertions, nucleotide deletions, methylated DNA sequences or other DNA sequence mutations. Typical cancer associated DNA abnormalities that may be investigated in such an analysis include, without limitation, point mutations, translocations, gene copy number mutations, microsatellite abnormalities, DNA strand integrity and gene methylation status.

In one embodiment, the method of the invention is repeated on multiple occasions. This embodiment provides the advantage of allowing the detection results to be monitored over a time period. Such an arrangement will provide the benefit of monitoring or assessing the efficacy of treatment of a disease state. Such monitoring methods of the invention can be used to monitor onset, progression, stabilisation, amelioration, relapse and/or remission.

Thus, the invention also provides a method of monitoring efficacy of a therapy for a disease state in a subject, suspected of having such a disease, comprising detecting and/or quantifying the biomarker present in a biological sample from said subject. In monitoring methods, test samples may be taken on two or more occasions. The method may further comprise comparing the level of the biomarker(s) present in the test sample with one or more control(s) and/or with one or more previous test sample(s) taken earlier from the same test subject, e.g. prior to commencement of therapy, and/or from the same test subject at an earlier stage of therapy. The method may comprise detecting a change in the nature or amount of the biomarker(s) in test samples taken on different occasions.

A change in the level of the biomarker in the test sample relative to the level in a previous test sample taken earlier from the same test subject may be indicative of a beneficial effect, e.g. stabilisation or improvement, of said therapy on the disorder or suspected disorder. Furthermore, once treatment has been completed, the method of the invention may be periodically repeated in order to monitor for the recurrence of a disease.

Methods for monitoring efficacy of a therapy can be used to monitor the therapeutic effectiveness of existing therapies and new therapies in human subjects and in non-human animals (e.g. in animal models). These monitoring methods can be incorporated into screens for new drug substances and combinations of substances.

In a further embodiment the monitoring of more rapid changes due to fast acting therapies may be conducted at shorter intervals of hours or days.

Identifying and/or quantifying can be performed by any method suitable to identify the presence and/or amount of a specific protein in a biological sample from a patient or a purification or extract of a biological sample or a dilution thereof. Biological samples that may be tested in a method of the invention include those as defined hereinbefore. The samples can be prepared, for example where appropriate diluted or concentrated, and stored in the usual manner.

Methods of the invention may be performed by detection of a fragment of the targets described herein, e.g. a fragment with C-terminal truncation, or with N-terminal truncation. Fragments are suitably greater than 4 amino acids in length, for example 5, 6, 7, 8, 9, 10, 11, 12, 13, 14, 15, 16, 17, 18, 19, or 20 amino acids in length. Such fragments may be binding fragments, i.e. they retain the ability of the whole protein to bind to the target. It is noted in particular that peptides of the same or related sequence to that of histone tails are particularly useful fragments of histone proteins. The biomarker may be directly detected, e.g. by SELDI or MALDI-TOF. Alternatively, the biomarker may be detected directly or indirectly via interaction with a ligand or ligands such as an antibody or a biomarker-binding fragment thereof, or other peptide, or ligand, e.g. aptamer, affimer, or oligonucleotide, capable of specifically binding the biomarker. The ligand or binder may possess a detectable label, such as a luminescent, fluorescent or radioactive label, and/or an affinity tag.

For example, detecting and/or quantifying can be performed by one or more method(s) selected from the group consisting of: SELDI (-TOF), MALDI (-TOF), a 1-D gel-based analysis, a 2-D gel-based analysis, Mass spec (MS), reverse phase (RP) LC, size permeation (gel filtration), ion exchange, affinity, HPLC, UPLC and other LC or LC MS-based techniques. Appropriate LC MS techniques include ICAT® (Applied Biosystems, CA, USA), or iTRAQ® (Applied Biosystems, CA, USA). Liquid chromatography (e.g. high pressure liquid chromatography (HPLC) or low pressure liquid chromatography (LPLC)), thin-layer chromatography, NMR (nuclear magnetic resonance) spectroscopy could also be used.

Methods of diagnosing or monitoring according to the invention may comprise analysing a sample to detect the presence or level of the biomarker. These methods are also suitable for clinical screening, prognosis, monitoring the results of therapy, identifying patients most likely to respond to a particular therapeutic treatment, for drug screening and development, and identification of new targets for drug treatment.

Identifying and/or quantifying may be performed using an immunological method, involving an antibody, or a fragment thereof capable of specific binding to the biomarker. Suitable immunological methods include sandwich immunoassays, such as sandwich ELISA, in which the detection of the analyte biomarkers is performed using two antibodies which recognize different epitopes on a analyte biomarker; radioimmunoassays (RIA), direct, indirect or competitive enzyme linked immunosorbent assays (ELISA), enzyme immunoassays (EIA), Fluorescence immunoassays (FIA), western blotting, immunoprecipitation and any particle-based immunoassay (e.g. using gold, silver, or latex particles, magnetic particles, or Q-dots). Immunological methods may be performed, for example, in microtitre plate or strip format.

Methods involving identification and/or quantification can be performed on bench-top instruments, or can be incorporated onto disposable, diagnostic or monitoring platforms that can be used in a non-laboratory environment, e.g.

in the physician's office or at the patient's bedside. Suitable biosensors for performing methods of the invention include "credit" cards with optical or acoustic readers. Biosensors can be configured to allow the data collected to be electronically transmitted to the physician for interpretation and thus can form the basis for e-medicine. As used herein, the term "biosensor" means anything capable of detecting the presence of the target.

Diagnostic kits for the diagnosis and monitoring of the presence of a disease state are described herein. In one embodiment, the kits additionally contain a biosensor capable of identifying and/or quantifying a biomarker. Suitably a kit according to the invention may contain one or more components selected from the group: a ligand binder, or ligands, specific for the biomarker or a structural/shape mimic of the biomarker, one or more controls, one or more reagents and one or more consumables; optionally together with instructions for use of the kit in accordance with any of the methods defined herein.

The identification of biomarkers for a disease state permits integration of diagnostic procedures and therapeutic regimes. For example, detection of a biomarker can be used to screen subjects prior to their participation in clinical trials. The biomarkers provide the means to indicate therapeutic response, failure to respond, unfavourable side-effect profile, degree of medication compliance and achievement of adequate serum drug levels. The biomarkers may be used to provide warning of adverse drug response. Biomarkers are useful in development of personalized therapies, as assessment of response can be used to fine-tune dosage, minimise the number of prescribed medications, reduce the delay in attaining effective therapy and avoid adverse drug reactions. Thus by monitoring a biomarker, patient care can be tailored precisely to match the needs determined by the disorder and the pharmacogenomic profile of the patient, the biomarker can thus be used to titrate the optimal dose, predict a positive therapeutic response and identify those patients at high risk of severe side effects.

Biomarker-based tests provide a first line assessment of 'new' patients, and provide objective measures for accurate and rapid diagnosis, not achievable using the current measures.

Furthermore, diagnostic biomarker tests are useful to identify family members or patients with mild or asymptomatic disease or who may be at high risk of developing symptomatic disease. This permits initiation of appropriate therapy, or preventive measures, e.g. managing risk factors. These approaches are recognised to improve outcome and may prevent overt onset of the disorder.

Biomarker monitoring methods, biosensors and kits are also vital as patient monitoring tools, to enable the physician to determine whether relapse is due to worsening of the disorder. If pharmacological treatment is assessed to be inadequate, then therapy can be reinstated or increased; a change in therapy can be given if appropriate. As the biomarkers are sensitive to the state of the disorder, they provide an indication of the impact of drug therapy.

The invention will now be illustrated with reference to the following non-limiting examples.

EXAMPLES

Example 1

We purchased two H1 protein products. The first was a recombinant H1 protein purchased from Sigma-Aldrich (Product No: H1917-100UG). The second was a biological H1 preparation isolated from calf thymus purchased from Merck-Millipore (Product no: 382150). We coated these H1 proteins, as well as recombinant H2A, H2B, H3 and H4 histone proteins (purchased from BPS Bioscience, Product Nos: 52021, 52022, 52023 and 52024, respectively), onto plastic microtitre wells at 5 μg/ml in 100 μl phosphate buffer (PBS, Product No: 70011-038), by overnight incubation at 2-8° C. The wells were blocked (wellChampion, Kem-En-Tec, Product No: 4900A) and 10 μl of a solution containing either (i) human native polynucleosomes purified from HeLa cells (Epicypher, Product No: 16-0003), which consists of a mixture of mononucleosomes and polynucleosomes that contain linker DNA, or (ii) H3.3 mononucleosomes comprising 147 bp of DNA, and hence no linker DNA (Epicypher, Product No: 16-0012), was added. Following overnight incubation, the wells were washed and any bound nucleosomes were detected by addition of a labelled anti-nucleosome antibody. Bound labelled antibody was measured using a colour substrate reaction and the resulting optical density (OD) was used as a measure of bound nucleosomes.

Figure 2:
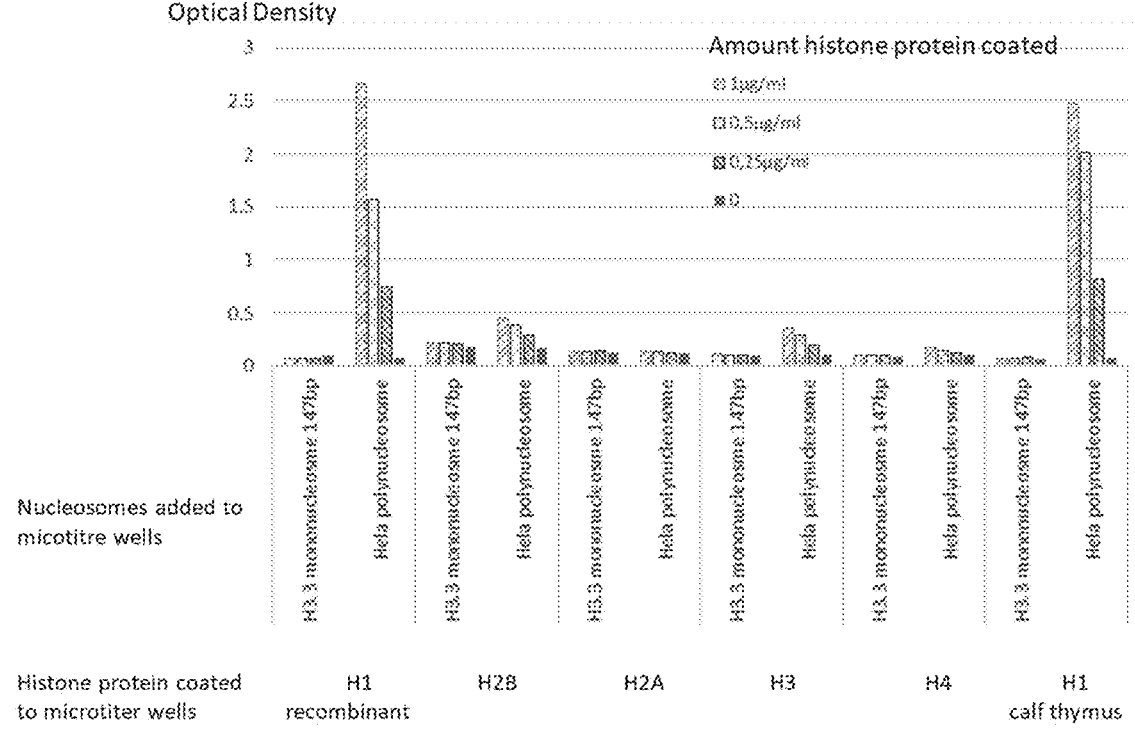
FIG. 2. Results using H1 protein to bind nucleosomes. H1 protein (both recombinant H1 and calf thymus derived H1 protein) binds to polynucleosomes which contain linker DNA, but not to mononucleosomes which do not contain linker DNA (recombinant mononucleosomes containing 147 bp DNA). Nucleosome binding was not observed for H2A, H2B, H3 or H4 histone proteins.

The results are shown in FIG. 2 and demonstrate that mononucleosomes and polynucleosomes containing linker DNA bind to H1 protein (both recombinant H1 and tissue derived H1 protein) but that mononucleosomes which do not contain linker DNA do not bind to H1 protein. Moreover, nucleosome binding was specific to histone H1 and was not observed for histone H2A, H2B, H3 or H4 proteins. These results demonstrate that H1 protein (but not other histone proteins) may be used to prepare immunosorbents that bind to nucleosomes containing linker DNA. The results also demonstrate that H1 protein or any protein that binds to nucleosomes can be used as a binder in an immunoassay for nucleosomes generally, or to certain types of nucleosomes that are bound selectively by the protein.

Example 2

We incubated streptavidin coated magnetic beads with recombinant mononucleosomes containing 167 bp of DNA that included the Widom 601 DNA sequence in the presence and absence of recombinant biotinylated histone H1. The beads were then isolated using a magnet, washed and treated with Proteinase-K to release any bound nucleosomal DNA. Released DNA was extracted, eluted and measured by a quantitative polymerase chain reaction (qPCR) method using Widom 601-sequence specific primers. The observed Ct value (cycle threshold for the number of cycles required for the signal to cross the threshold above background) in the presence of H1 was less than half of the Ct value observed in the absence of H1. This indicates that the binding of recombinant nucleosomes containing 167 bp DNA fragments bound to the streptavidin beads was more than 400-fold higher in the presence of H1 than in its absence and that hence that nucleosomes containing 167 bp DNA were bound by H1 on the magnetic beads.

The results of this experiment demonstrate that H1 protein coated beads can be used to bind and isolate nucleosomes containing 167 bp of DNA (i.e. that include linker DNA) and can be used to prepare immunosorbents for use in methods of the invention to bind to nucleosomes containing particular structures, properties or biological origins and/or to enrich or deplete a sample for such nucleosomes.

The results of this experiment showed that immobilised histone H1 protein binds recombinant nucleosomes containing 167 bp DNA fragments. The results of the experiment described in Example 1 showed that immobilised histone H1 protein does not bind recombinant nucleosomes containing 147 bp DNA fragments. Therefore, in combination, Examples 1 and 2 demonstrate that histone H1 protein can be used to selectively bind to nucleosomes containing linker DNA and hence can be used as a tool to enrich and/or separate nucleosomes containing, or not containing, linker DNA.

Example 3

In a similar experiment to that described in Example 2 using a plasma sample taken from a patient diagnosed with cancer, streptavidin coated magnetic beads are incubated with recombinant biotinylated histone H1 and the plasma sample. The beads are then isolated using a magnet, washed and treated with Proteinase-K to release any bound nucleosomal DNA. Released DNA is isolated and, after washing, eluted and analysed using a Bioanalyzer to measure the fragment size distribution of the isolated DNA. The observed size distribution of the isolated DNA consists of 2 bands. The main band is observed at approximately 150-230 bp in length with a peak at approximately 170 bp corresponding to the non-tumour peak as illustrated in FIG. 1. A further smaller band is observed at approximately 300-450 bp corresponding to the size range expected for di-nucleosomes and tri-nucleosomes.

The tumour band shown in FIG. 1 at approximately 120-150 bp DNA is entirely missing from the fragment size profile of the H1 bound nucleosomes in the plasma cancer sample. This demonstrates that nucleosomes containing DNA fragments of less than 150 bp in length are not bound to the histone H1 linked magnetic beads.

The results show that the methods of the invention can be used to bind and remove mononucleosomes and polynucleosomes containing linker DNA from plasma samples, whilst nucleosomes that do not contain linker DNA remain in solution. The liquid phase is thus separated, purified and enriched for tumour derived plasma nucleosomes.

Example 4

A histone H1 coated magnetic bead reagent is incubated with a plasma sample taken from a cancer patient. The magnetic bead reagent is isolated using a magnet and both the DNA bound to the magnetic beads and the unbound DNA present in the liquid phase are extracted using a method known in the art.

The presence of any cancer associated genetic mutations is investigated and the mutant allele fraction determined in the untreated sample and in both the magnetic bead bound and unbound DNA fractions. The MAF of the unbound fraction is higher than that of the untreated sample or the bound fraction.

Example 5

A histone H1 coated magnetic bead reagent is incubated with a plasma sample taken from a cancer patient. The magnetic reagent is isolated using a magnet and the DNA present in the liquid phase is extracted using a method known in the art. The extracted DNA is sequenced.

The presence of any cancer associated genetic mutations is investigated and the mutant allele fraction determined. In addition, the DNA sequence is investigated using the "fragmentomics" approach to identify the tissue of origin of DNA fragments in the plasma sample. The MAF and/or mutation profile and/or "fragmentomics" profile of the sample is used to indicate the presence of a cancer in the patient. This information may be used to select an appropriate treatment for the patient.

The extracted DNA is also analysed for methylated DNA using an appropriate method (e.g. bisulfite sequencing). The methylated DNA results of the sample are used to indicate the presence, progression or relapse of a cancer in the patient.

Example 6

A genetically engineered protein is developed to bind strongly to nucleosomes containing linker DNA using methods known in the art, for example the method of (Wiesler and Weinzierl, 2010). The protein may be based on any protein or any protein domain. In the present example, mutational analysis of the H1 protein is performed with systematic amino acid changes and derived H1 mutants are tested for binding to nucleosomes containing linker DNA. Those mutants with the strongest binding are selected as candidates for use in an immunosorbent to bind nucleosomes containing linker DNA. Candidate mutant proteins are then tested for binding to nucleosomes without linker DNA and candidates with no, or weak binding, are selected. The engineered proteins developed may bind more strongly to nucleosomes containing linker DNA and less strongly to those without linker DNA. Such engineered proteins or peptides can be produced in large quantities and may be used as binders in methods of the invention.

Example 7

Figure 3:
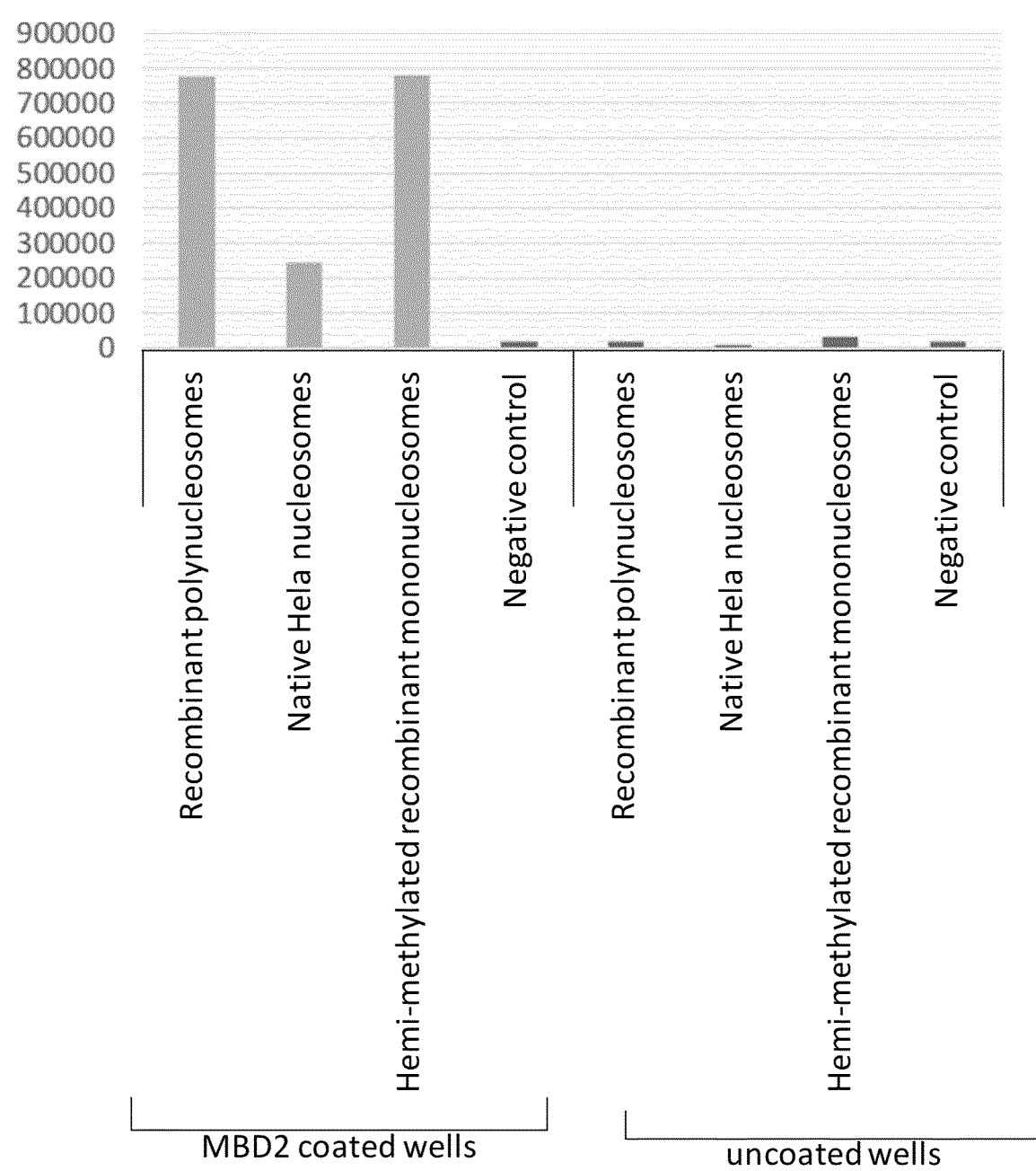
FIG. 3. Results using MBD2 protein to bind nucleosomes. MBD2 protein coated onto beads binds to polynucleosomes and nucleosomes containing high levels of methylated DNA.

We coated Methyl Binding Domain 2 (MBD2) protein on Dynabeads M280 magnetic beads according to the manufacturer's instructions (Thermo Fisher Scientific). The beads were exposed to 5 µg/ml recombinant polynucleosomes containing unmethylated linker DNA (Active Motif, Product No: 31466), human native nucleosomes purified from HeLa cells digested with micrococcal nuclease consisting mostly of mononucleosomes some of which contain methylated DNA (Diagenode, Product No: 001030102) and hemi-methylated recombinant mononucleosomes with 187 bp of DNA all of which contain methylated linker DNA (EpiCypher, Product No: SKU:16-2103). The beads were isolated magnetically, washed and bound nucleosomes measured using a chemiluminescent labelled anti-nucleosome antibody. The results are shown in FIG. 3 and demonstrate that the MBD protein binds to polynucleosomes containing linker DNA. Moreover, nucleosome binding was stronger for mononucleosomes containing high levels of methylated DNA.

Example 8

Figure 4:
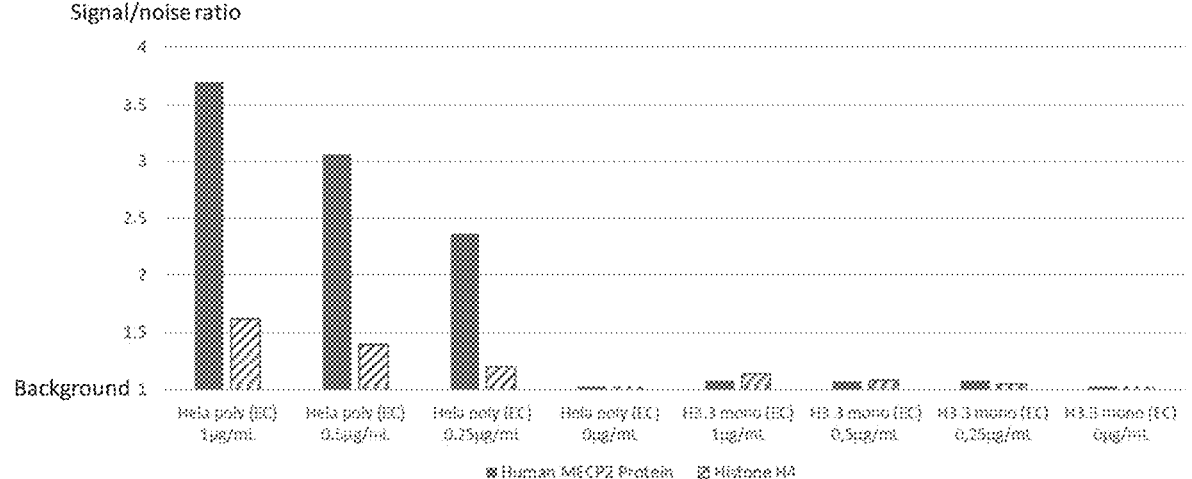
FIG. 4. Results using MECP2 protein to bind nucleosomes. MECP2 (an MBD protein) binds to nucleosomes containing linker DNA (HeLa poly), but not nucleosomes which do not contain linker DNA (mononucleosomes containing 147 bp DNA).

We developed an ELISA assay utilising an MBD protein coated on the surface of microtitre plate wells as a capture protein for cell free nucleosomes and used the assay to measure the level of nucleosomes containing linker DNA. In brief, MBD protein was coated onto plastic microtitre wells at 5 µg/ml in 100 µl phosphate buffer (PBS, Product No: 70011-038), by overnight incubation at 2-8° C. Histone H4 was also coated onto wells in a similar manner, for use as a control. The wells were blocked (wellChampion, Kem-En-Tec, product no: 4900A) and 10 µl of serial dilutions of either a solution containing 1 µg/ml of human native polynucleosomes purified from HeLa cells (Epicypher, Product No: 16-0003) or a solution containing 1 µg/ml of H3.3 mononucleosomes comprising 147 bp (Epicypher, Product No: 16-0012) was added. Following overnight incubation, the wells were washed and any bound nucleosomes were detected by addition of a labelled anti-nucleosome antibody. Results are shown in FIG. 4 and demonstrate that MBD binds to nucleosomes containing linker DNA (HeLa poly-nucleosomes), but does not bind to nucleosomes which do not contain linker DNA (H3.3 mononucleosomes).

Figure 5:
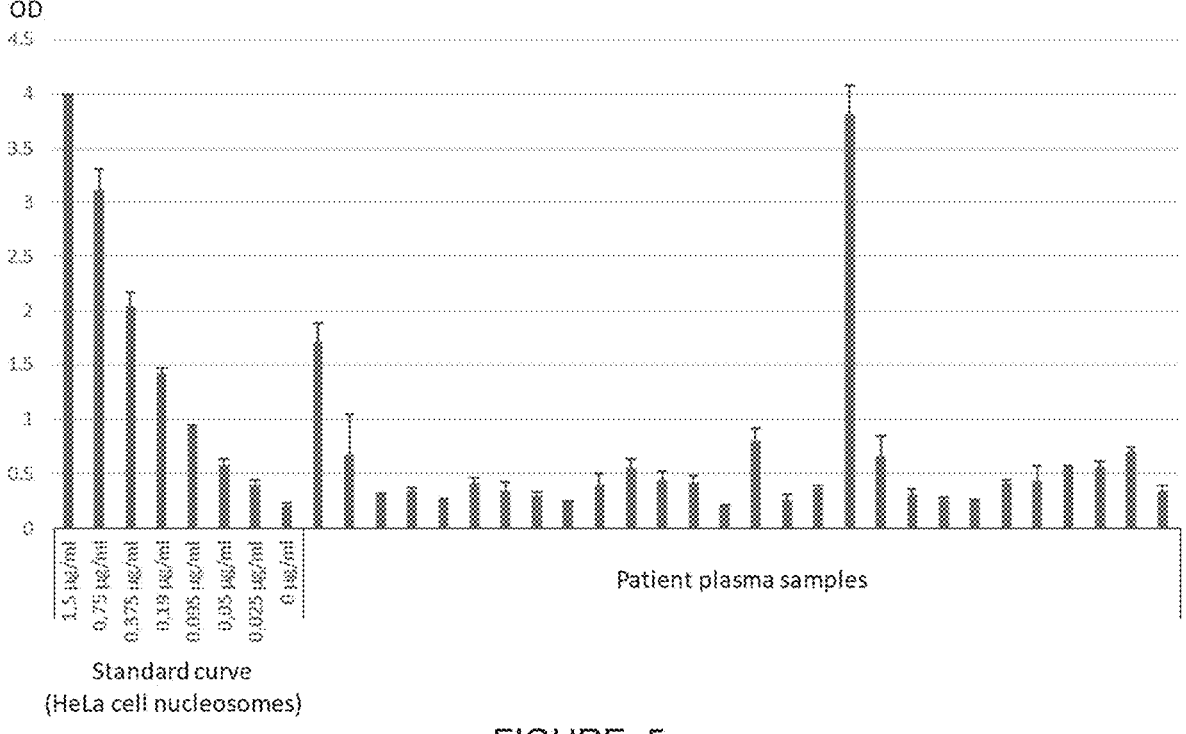
FIG. 5. Results for an ELISA assay using MBD protein to bind nucleosomes in clinical samples. MBD was tested as a binding agent in an ELISA assay in 28 human plasma samples. Results show protein may be used as a binder to detect nucleosomes in clinical samples.

We also used this assay to test 28 human plasma samples and the results are shown in FIG. 5 including a standard curve based on dilutions of human native nucleosomes purified from HeLa cells (BPS Biosciences, Product No: 52039). The results show that MBD may be used as a binding agent in ELISA type assays for clinical samples.

Example 9

Chromodomain Helicase DNA Binding Protein (CHD), DNA (cytosine-5)-methyltransferase protein (DNMT), High mobility group or high mobility group box protein (HMG or HMGB), Poly [ADP-ribose] polymerase protein (PARP) or p53 is coated to Dynabeads M280 magnetic beads according to the manufacturer's instructions. The beads are exposed to a variety of nucleosomes including recombinant mononucle-osomes containing 147 bp, 167 bp or 187 bp of DNA, recombinant polynucleosomes (Active Motif, catalogue no. 31466), human native nucleosomes purified from HeLa cells and hemi-methylated recombinant mononucleosomes (Epi-Cypher, catalogue no. SKU:16-2103). The beads are isolated magnetically, washed and bound nucleosomes measured using a chemiluminescent labelled anti-nucleosome anti-body. The results may be used to demonstrate that beads coated with different chromatin binding proteins can be used to bind and isolate nucleosomes and can be used to prepare immunosorbents for use in methods of the invention to bind to nucleosomes containing particular structures, properties or biological origins and/or to enrich or deplete a sample for such nucleosomes. The DNA associated with nucleosomes (in particular the nucleosomes not bound to the magnetic beads) may be extracted and analysed.

Example 10

Chromodomain Helicase DNA Binding Protein (CHD), DNA (cytosine-5)-methyltransferase protein (DNMT), High mobility group or high mobility group box proteins protein (HMG or HMGB), Poly [ADP-ribose] polymerase protein (PARP) or p53 is coated to microtitre wells as described in Example 9 above. Each well is blocked and a sample is added. Following incubation, the sample is discarded, the wells are washed and bound nucleosomes are measured using a labelled anti-nucleosome antibody. The results can be used to demonstrate that wells coated with CHD, DNMT, HMG, HMGB or PARP can be used for an immunoassay to measure the levels of nucleosomes in a sample that contain particular structures that relate to the particular protein immobilised on the surface of the well.

In another experiment, the labelled antibody used is not a general anti-nucleosome antibody but is directed to bind to a particular epigenetic feature of a nucleosome such as a histone isoform, a histone modification or a protein adducted to a nucleosome.

Example 11

An antibody is developed using a library Phage Display Technology using positive selection for binding to mono-nucleosomes containing 167 bp of DNA. Phage binder clones in the library identified as positive for binding to mononucleosomes containing 167 bp of DNA are immobi-lised at various coating levels onto a solid support and exposed to mononucleosomes containing 147 bp, 167 bp or 187 bp DNA fragments. The binding of nucleosomes to the binder clones is detected using a labelled anti-nucleosome antibody. Clones with a high affinity for binding to mono-nucleosomes containing 167 bp and/or 187 bp of DNA (i.e. nucleosomes with linker DNA) but low affinity for binding to mononucleosomes containing 147 bp of DNA are selected and used for the development of immunosorbents for posi-tive binding selection of nucleosomes containing linker DNA.

Example 12

An antibody is developed using a library Phage Display Technology using positive selection for binding to mono-nucleosomes containing 147 bp of DNA. Phage binder clones in the library identified as positive for binding to mononucleosomes containing 147 bp of DNA are immobi-lised at various coating levels onto a solid support and exposed to mononucleosomes containing 147 bp, 167 bp or 187 bp DNA fragments. The binding of nucleosomes to the binder clones is detected using a labelled anti-nucleosome antibody. Clones with a high affinity for binding to mono-nucleosomes containing 147 bp of DNA (i.e. nucleosomes without linker DNA) but low affinity for binding to mono-nucleosomes containing 167 bp or 187 bp of DNA are selected and used for the development of immunosorbents for positive binding selection of nucleosomes containing no linker DNA.

Example 13

We developed an antibody using the AxioMx Inc. library Phage Display Technology using positive selection of clones for binding to mononucleosomes containing 147 bp of DNA.

Three antibodies produced were biotinylated and tested by measuring their binding to recombinant nucleosomes containing either 147 bp, 167 bp or 187 bp DNA. Briefly, recombinant nucleosomes were immobilised on microtitre wells by coating with a nucleosome solution (1 µg/ml). The wells were blocked using a commercial blocking reagent. Biotinylated antibody solution (1 µg/ml) was added and incubated for 2 hours at room temperature with gentle shaking. The antibody solution was then decanted and the wells were washed 3 times with a wash buffer. A solution containing a streptavidin-horse radish peroxidase (HRP) conjugate was added and incubated for 15 minutes at room temperature. The wells were washed again and the bound HRP was measured using a 3,3',5,5'-Tetramethylbenzidine substrate and measuring the optical density (OD) produced at 450 nm. The results are shown in Table 1 below.

TABLE 1

| Binding of 3 antibodies to nucleosomes containing no linker DNA, approximately 20 bp of linker DNA or approximately 40 bp of linker DNA | | | |
|---|---|---|---|
| Length of DNA (bp) associated with coated nucleosome | OD Antibody 1 | OD Antibody 2 | OD Antibody 3 |
| 147 bp (no linker DNA) | 0.34 | 0.93 | 0.63 |
| 167 bp (~20 bp linker DNA) | 0.27 | 0.81 | 0.55 |

TABLE 1-continued

| Binding of 3 antibodies to nucleosomes containing no linker DNA, approximately 20 bp of linker DNA or approximately 40 bp of linker DNA | | | |
|---|---|---|---|
| Length of DNA (bp) associated with coated nucleosome | OD Antibody 1 | OD Antibody 2 | OD Antibody 3 |
| 187 bp (~40 bp linker DNA) | 0.20 | 0.52 | 0.40 |
| Control (no coated nucleosome) | 0.04 | 0.04 | 0.04 |

The results show stronger binding for nucleosomes containing no linker DNA for all 3 antibodies. The binding is weaker for nucleosomes containing increasing lengths of linker DNA and the antibodies may be used for positive selection and enrichment of nucleosomes containing no linker DNA.

Figure 6:
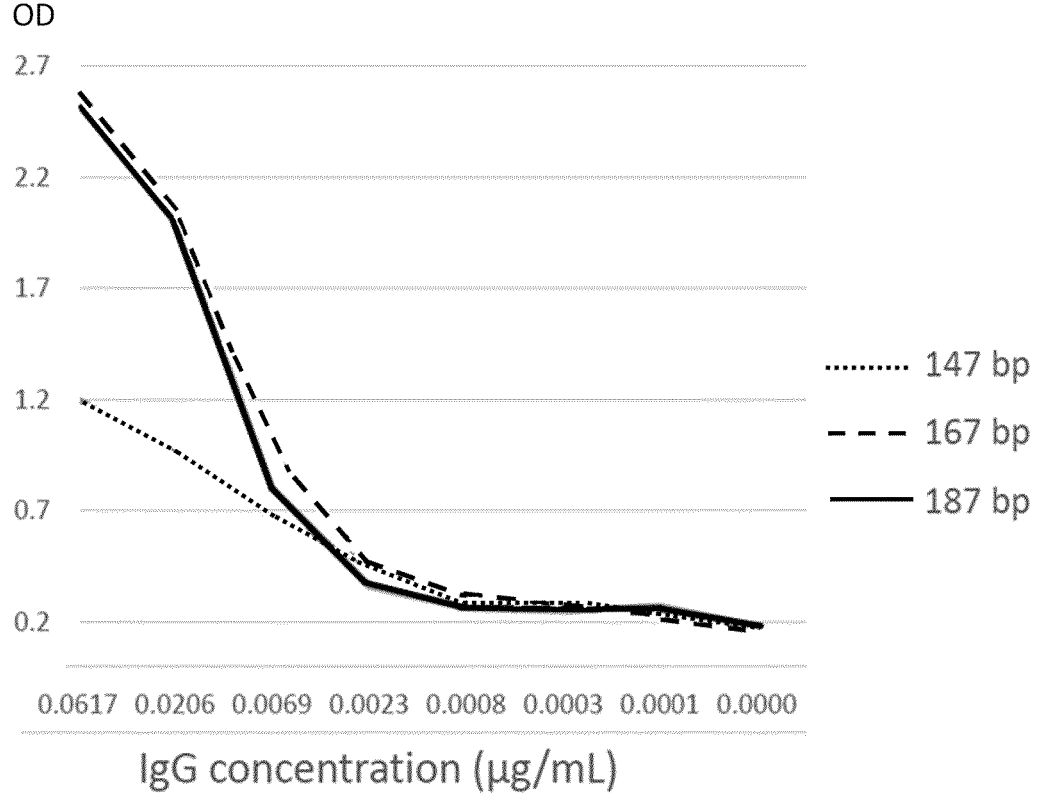
FIG. 6. Generation of an antibody to bind nucleosomes containing linker DNA. The antibody has a higher (and approximately equal) affinity for mononucleosomes containing 167 bp or 187 bp of DNA but a much lower affinity for nucleosomes containing 147 bp of DNA.

Phage binder clones identified as positive for binding to mononucleosomes were immobilised at various coating levels onto a solid support and exposed to mononucleosomes containing 147 bp, 167 bp or 187 bp DNA fragments. This experiment was similar to that described above where the nucleosomes were immobilised and exposed to liquid phase antibody, but was reversed in that the antibody was immobilised and exposed to liquid phase nucleosomes. The binding of nucleosomes to the binder clones was detected using a labelled anti-nucleosome antibody. The results for one clone are shown in FIG. 6 and demonstrate that the clone had a high (and approximately equal) affinity for mononucleosomes containing 167 bp or 187 bp of DNA but a much lower affinity for nucleosomes containing 147 bp of DNA (i.e. nucleosomes without linker DNA). It will be clear to those skilled in the art, that a binder with higher affinity for nucleosomes containing linker DNA than for nucleosomes without linker DNA, can be used to bind to nucleosomes containing linker DNA (almost exclusively) especially if those nucleosomes are also present in a sample at much higher concentration than the nucleosomes with no linker DNA.

The results demonstrate that antibodies can be developed to selectively bind to epitopes present on nucleosomes with or without linker DNA. Such engineered antibodies or antibody fragments are useful for the development of immunosorbents to be used in methods of the invention to bind to nucleosomes with different structures, properties or biological origins and/or to enrich or deplete a sample for nucleosomes of certain structures, properties or biological origins. For example, an antibody engineered to bind preferentially to nucleosomes containing no linker DNA may be used in a positive selection method to enrich a sample containing nucleosomes without linker DNA (by binding to those nucleosomes containing linker DNA). Similarly, an antibody engineered to bind preferentially to nucleosomes containing linker DNA may be used in a negative selection method to enrich a sample containing nucleosomes without linker DNA (by binding to and removing nucleosomes containing linker DNA).

The target epitopes for such antibodies may be of various types. For example, target epitopes may reside in structures only present in nucleosomes containing linker DNA or in structures only present in nucleosomes that do not contain linker DNA. For example, such structures may be additional structures (especially in nucleosomes containing linker DNA) or may be unmasked by the absence or removal of structures otherwise present (especially in nucleosomes not containing linker DNA). Target epitopes may also be conformational in nature, such that the presence or absence of linker DNA is associated with alternative nucleosome conformations that may be bound with higher or lower affinity by an antibody developed for this purpose. Other target epitopes are also possible.

Example 14

An experiment similar to that described in Example 3 is performed using a streptavidin coated magnetic bead reagent together with a biotinylated antibody directed to bind to the histone isoform macroH2A. The magnetic beads and biotinylated antibody are incubated with a plasma sample taken from a cancer patient. The magnetic bead reagent is isolated using a magnet and both the DNA bound to the magnetic beads and the unbound DNA present in the liquid phase are extracted using a method known in the art.

The presence of any cancer associated genetic mutations is investigated and the mutant allele fraction determined in both the magnetic bead bound and unbound DNA fractions. The MAF of the unbound fraction is higher than that of the bound fraction.

Example 15

An antibody directed to bind to a chromatin binding protein, such as Methyl Binding Domain (MBD), Chromodomain Helicase DNA Binding Protein (CHD), DNA (cytosine-5)-methyltransferase protein (DNMT), High mobility group or high mobility group box proteins protein (HMG or HMGB), Poly [ADP-ribose] polymerase protein (PARP) or to p53, is coated to Dynabeads M280 magnetic beads according to the manufacturer's instructions. The beads are exposed to a variety of nucleosomes including recombinant mononucleosomes containing 147 bp, 167 bp or 187 bp of DNA, recombinant polynucleosomes, human native nucleosomes purified from HeLa cells digested with micrococcal nuclease and hemi-methylated recombinant mononucleosomes. The beads are isolated magnetically, washed and bound nucleosomes measured using a chemiluminescent labelled anti-nucleosome antibody. The results can be used to demonstrate that beads coated with different antibodies directed to chromatin binding proteins can be used to bind and isolate nucleosomes and can be used to prepare immunosorbents for use in methods of the invention to bind to nucleosomes containing particular structures, properties or biological origins and/or to enrich or deplete a sample for such nucleosomes.

Example 16

An antibody directed to bind to a chromatin binding protein, such as Methyl Binding Domain (MBD), Chromodomain Helicase DNA Binding Protein (CHD), DNA (cytosine-5)-methyltransferase protein (DNMT), High mobility group or high mobility group box proteins protein (HMG or HMGB), Poly [ADP-ribose] polymerase protein (PARP) or p53, is coated to microtitre wells. Each well is blocked and a sample is added. Following incubation, the sample is discarded, the wells are washed and bound nucleosomes are measured using a chemiluminescent labelled anti-nucleosome antibody. The results demonstrate that wells coated with different antibodies can be used for immunoassay of nucleosomes containing chromatin binding proteins, such as MBD, CHD, DNMT, HMG, HMGB or PARP.

In another experiment, the second antibody used is not a general anti-nucleosome antibody but is directed to bind to a particular epigenetic feature of a nucleosome such as a histone isoform, a histone modification or a protein adducted to a nucleosome

Example 17

An antibody directed to bind to the histone isoform H2AZ is coated to Dynabeads M280 magnetic beads following the manufacturer's instructions. The beads are washed and a sample is added. Following incubation, the sample is discarded and the magnetic beads are washed again. The nucleosomes now bound to the solid phase are enriched for nucleosomes containing no linker DNA. The isolated bound nucleosomes may be analysed for example by mass spectrometry or by sequencing of nucleosome associated DNA.

Example 18

We noticed as a general observation, that an assay designed to measure total nucleosome levels using a first antibody directed to bind histone H3 at an epitope in the histone tail at amino acid positions 4-8 and a second anti-nucleosome antibody directed to bind elsewhere in the nucleosome sometimes gave lower results for patient samples than assays for nucleosomes containing the histone modifications H3K36Me3 or H3K27Me3 using the same second antibody. As the true concentration of a subset of modified nucleosomes cannot exceed the true concentration of total nucleosomes, this was an anomalous observation. We reasoned that this finding may be due to the presence of nucleosomes containing clipped histones. It was predicted that such clipped nucleosomes would not contain the epitope at amino acid positions 4-8 (as it would have been removed) but would contain lysines at positions 27 and 36.

We exposed recombinant polynucleosomes containing no clipped histones to the protease cathepsin which cleaves the histone tail of H3 at position amino 21. The success of this digestion was confirmed by Western Blot. We then analysed protease treated and untreated recombinant polynucleosomes using two different pairs of antibodies. The first antibody pair (pair 1) was that described above consisting of one antibody directed to bind histone H3 at an epitope in the histone tail at amino acid positions 4-8 and an anti-nucleosome antibody directed to bind elsewhere in the nucleosome. The second antibody pair (pair 2) consisted of one antibody directed to bind histone H3 at an epitope at amino acid positions 30-33 and the same anti-nucleosome antibody directed to bind elsewhere in the nucleosome.

As expected, both antibody pairs gave equivalent signals for untreated recombinant polynucleosomes containing no clipped histones. Antibody pair 2 gave equivalent signals for protease treated and untreated polynucleosomes. This was also expected because the clipping site is below the antibody binding site so all nucleosomes contained the binding sites for both antibodies in pair 2. However, antibody pair 1 gave a lower signal for protease treated than untreated polynucleosomes. We conclude that this is because the clipping site is above the antibody binding site at amino acid position 4-8 so the binding site of the antibody was removed from a large proportion of the nucleosomes.

We also measured the protease treated and untreated polynucleosomes using an immunoassay devised to measure nucleosomes containing clipped histones. This assay used an antibody targeted to bind only to clipped histone H3 in combination with the same anti-nucleosome antibody directed to bind elsewhere in the nucleosome. This assay gave a negative result for the untreated polynucleosomes and a positive result for protease treated polynucleosomes.

Figure 7:
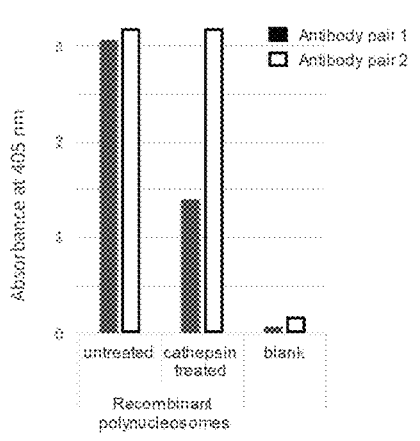
FIG. 7. Immunoassay results for nucleosomes containing clipped histones. (A) An assay targeted to an epitope near to the end of the tail of histone H3 (Antibody pair 1) has a strong signal for nucleosomes containing intact histone H3 but a reduced signal for nucleosomes in which some tails have been removed (clipped) by cathepsin digestion. No such effect occurs for an assay targeted to an epitope present in nucleosomes containing either intact or clipped histone H3 (Antibody pair 2). (B) An assay designed to detect only nucleosomes containing clipped histone H3 gives no signal for nucleosomes containing intact histone H3 but a strong signal for cathepsin treated nucleosomes.
Figure 7:
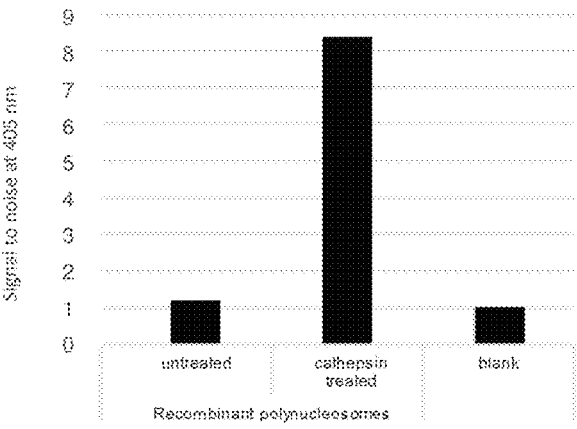

These results, shown in FIG. 7, demonstrate that we are able to selectively bind nucleosomes containing clipped histones, separate these on a solid phase support and analyse them by any method including immunoassay or mass spectrometry. It will be clear to those skilled in the art that immobilised nucleosomes containing clipped histones may also be analysed for any appropriate epigenetic features. Similarly, the DNA associated with isolated nucleosomes containing clipped histones may be analysed by any method including any DNA sequencing method.

Example 19

Figure 8:
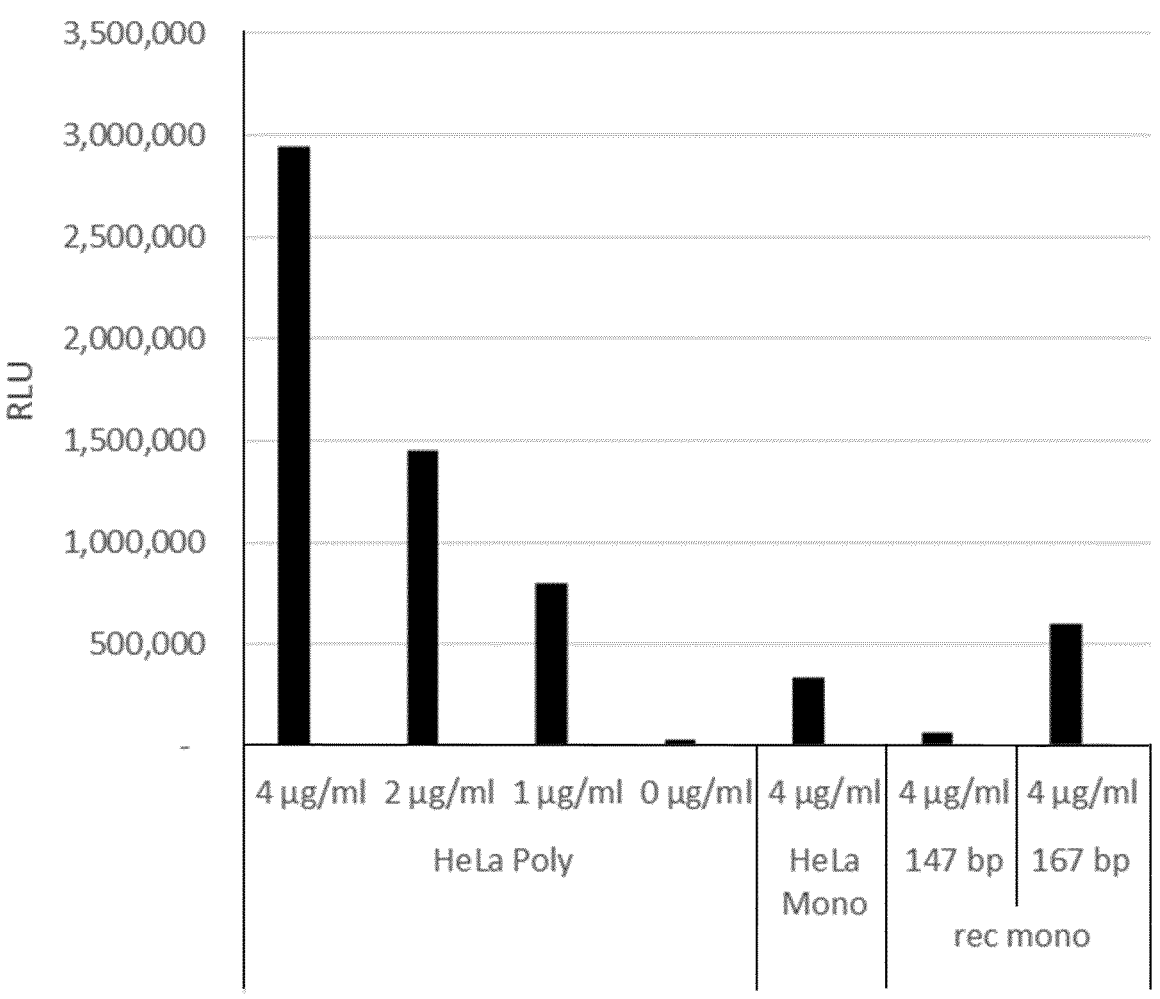
FIG. 8. Results using a Histone H1.0 protein analysed using a chemiluminescent labelled antibody. Light signals in Relative Light Units (RLU) produced by a chemilumines- cent labelled anti-Histone H3.1 antibody bound to various nucleosome moieties bound to Histone 1.0. The results show that H1.0 protein linked to magnetic beads binds to Hela polynucleosomes, and to Hela mononucleosomes and to recombinant mononucleosomes which contain 167 bp DNA, but does not bind to recombinant mononucleosomes which contain 147 bp DNA (i.e. do not contain linker DNA).

We produced a histone H1.0 protein by expression in the bacterium *Escherichia coli*. We used the H1.0 isoform of histone H1 as we found that this isoform performs well in methods of the invention. The histone H1.0 protein was used to coat commercially available magnetic beads and added to solutions containing commercially available preparations of Hela cell mononucleosomes produced by digestion of Hela cell chromatin, Hela cell polynucleosomes, recombinant mononucleosomes containing histone H3.1 and 147 bp DNA and recombinant mononucleosomes containing histone H3.1 and 167 bp DNA. The beads were isolated magnetically, washed and bound nucleosomes measured using a chemiluminescent labelled anti-Histone H3.1 antibody. The results are shown in FIG. 8 and demonstrate that the magnetic beads bound to polynucleosomes and mononucleosomes containing linker DNA (Hela mononucleosomes and recombinant mononucleosomes containing 167 bp DNA) but did not bind to mononucleosomes containing no linker DNA (recombinant mononucleosomes containing 147 bp DNA).

Example 20

Figure 9:
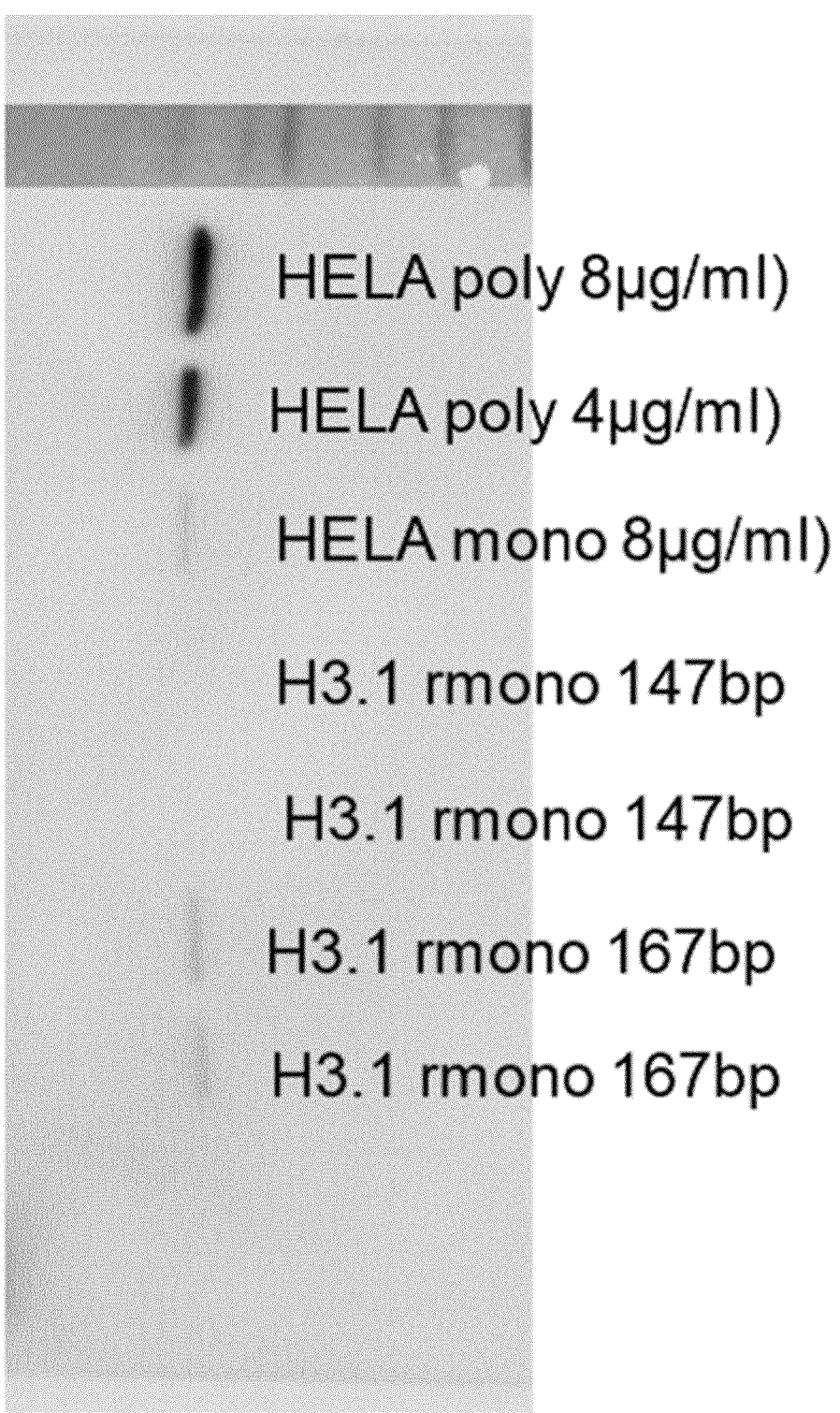
FIG. 9. Results using a Histone H1 protein analysed by Western blot. Protein bands developed using a labelled anti-Histone H3.1 antibody for proteins bound to Histone H1 protein linked to magnetic beads. The results show bands for magnetic Histone H1 exposed to Hela polynucleosomes, Hela mononucleosomes and to recombinant mononucle- osomes which contain 167 bp DNA, but no bands were observed for recombinant mononucleosomes which contain 147 bp DNA (i.e. do not contain linker DNA).

Tosylactivated M280 magnetic beads coated with calf thymus Histone H1 protein were exposed to solutions containing commercially available preparations of Hela cell mononucleosomes produced by digestion of Hela cell chromatin, Hela cell polynucleosomes, recombinant mononucleosomes containing histone H3.1 and 147 bp DNA and recombinant mononucleosomes containing histone H3.1 and 167 bp DNA as described in Example 19 above. The beads were isolated magnetically, washed and bound nucleosomes were eluted from the beads using a high molarity buffer. The eluate was analysed by a Western blot method developed using an enzyme labelled anti-Histone H3.1 antibody. The results are shown in FIG. 9. Strong Histone H3.1 bands were produced for magnetic bead eluates from beads exposed to Hela polynucleosomes and weaker Histone H3.1 bands were produced for mononucleosomes containing linker DNA (Hela mononucleosomes and recombinant mononucleosomes containing 167 bp DNA) but no band was observed for eluates from beads exposed to mononucleosomes containing histone H3.1 but no linker DNA (recombinant mononucleosomes containing 147 bp DNA).

Example 21

Figure 10:
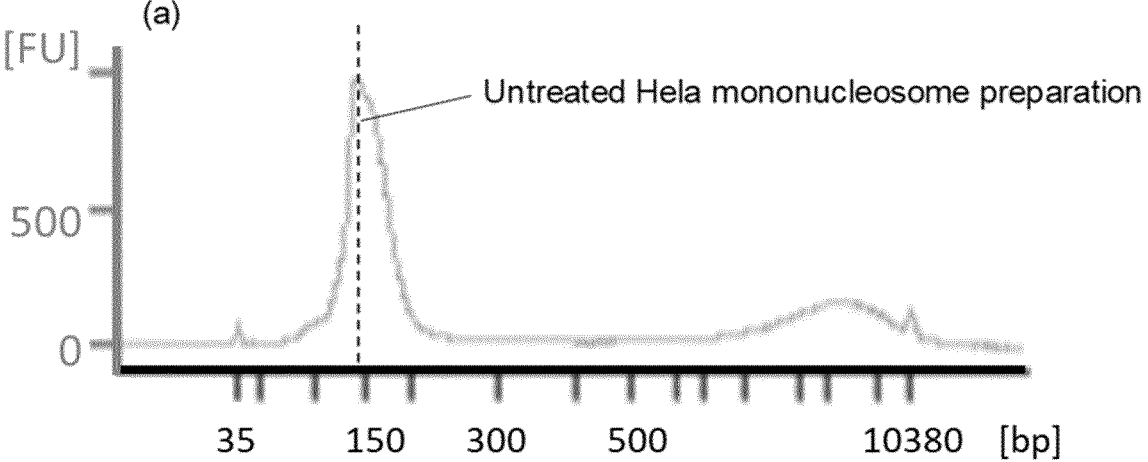
FIG. 10. Results for the separation of mononucleosomes with or without linker DNA in a commercial Hela cell mononucleosome preparation using a Histone H1.0 protein. (a) the DNA fragment size profile of a commercial Hela cell chromatin mononucleosome preparation. (b) the DNA frag- ment size profiles of the magnetic-H1.0 bound and unbound DNA fragment fractions of the same mononucleosomes preparation after exposure to Histone H1.0 linked to mag- netic beads.
Figure 10:
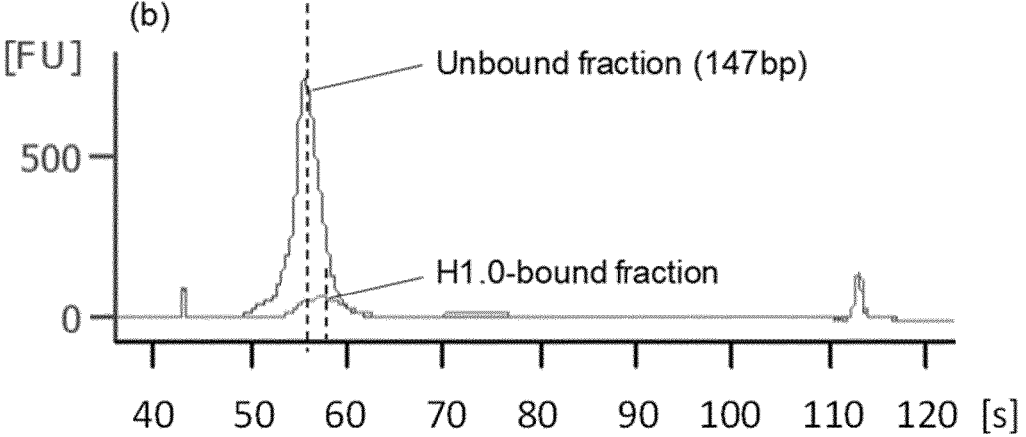

Commercial Hela cell mononucleosome preparations prepared by chromatin digestion may include a mixture of both mononucleosomes containing 147 bp DNA and 167 bp fragments of DNA. We purchased a commercially available preparation of Hela cell mononucleosomes and analysed the preparation for the size of associated DNA fragments using an Agilent Bioanalyzer. We observed that the preparation gave a peak with a maximum for DNA fragment size of approximately 147 bp as shown in FIG. 10(*a*). However, the peak was not symmetrical but included a shoulder corresponding to the presence of longer DNA fragments Magnetic beads coated with the histone H1.0 protein were exposed to the Hela cell mononucleosome preparation. The beads were isolated magnetically and washed. Then, both the Histone H1.0-bound nucleosome associated DNA fragment fraction isolated on the beads, as well as the unbound nucleosome associated DNA fragment fraction remaining in solution, were extracted using a Qiagen DNA extraction kit for isolation of free-circulating DNA fragments. The bound and unbound DNA fractions were analysed for base-pair length using an Agilent Bioanalyzer. The results are shown in FIG. 10(*b*) and show that the unbound fraction contained most of the nucleosomes and analysis gave a Bioanalyzer peak corresponding to a DNA size of approximately 147 bp. However, the shoulder corresponding to the longer DNA fragments present in the untreated preparation was not observed. Analysis of the histone H1.0-bead-bound fraction gave a smaller DNA peak with a maximum corresponding to a longer DNA fragment size.

Example 22

Commercially available Hela cell mononucleosomes prepared by chromatin digestion including mononucleosomes containing 147 bp DNA and 167 bp fragments of DNA were analysed for the size of associated DNA fragments using an Agilent Bioanalyzer with and without prior separation by a method of the invention.

Figure 11:
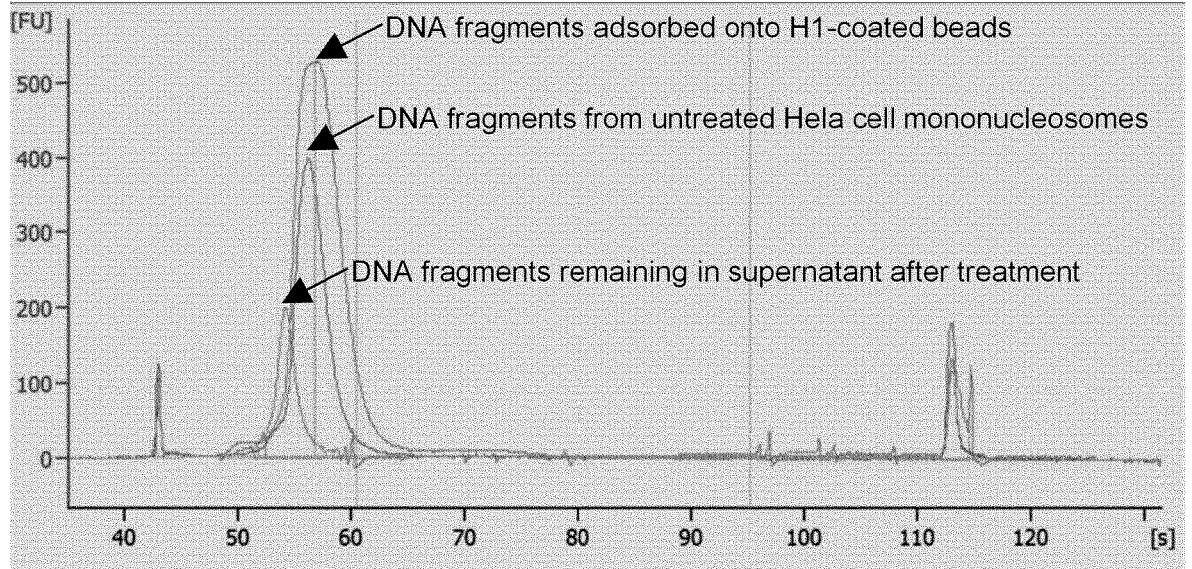
FIG. 11. Separation of mononucleosomes with or without linker DNA in a commercial Hela cell mononucleosome preparation. MyOne Tosylactivated magnetic beads coated with a Histone H1.0 protein were exposed to the Hela cell mononucleosome preparation using a Histone H1.0 fusion protein. The Bioanalyzer results show that the unbound DNA fraction remaining in the supernatant after treatment of the sample with H1 coated magnetic beads gave a Bioana- lyzer peak corresponding to a DNA size of approximately 147 bp which is clearly separated from the peak correspond- ing to the longer DNA associated with H1-bound nucle- osomes. DNA extracted from the untreated Hela nucleosome preparation had a peak at an intermediate size between the bound and unbound fractions. Results are expressed in Fluorescence Units (FU) against time in seconds (s).

A fresh preparation of MyOne Tosylactivated magnetic beads coated with a histone H1.0 protein were exposed to the Hela cell mononucleosome preparation using an optimised ratio of beads to mononucleosomes. The beads were isolated magnetically and washed. Then, DNA was extracted from the untreated Hela nucleosome preparation as well as from the Histone H1.0-bound nucleosome fraction isolated on the beads and from the unbound fraction remaining in solution in the supernatant after treatment, using a QIAamp® Circulating Nucleic Acid kit for the isolation of free-circulating DNA fragments. The untreated, bead-bound and unbound supernatant DNA fractions were analysed for base pair length using an Agilent Bioanalyzer. The Bioanalyzer results are shown in FIG. 11 and show that the unbound DNA fraction remaining in the supernatant after treatment of the sample with H1 coated magnetic beads gave a Bioanalyzer peak corresponding to a DNA size of approximately 147 bp which is clearly separated from the peak corresponding to the longer DNA fragments that included linker DNA associated with H1-bound nucleosomes (approximately 167 bp). DNA extracted from the untreated Hela nucleosome preparation had a peak at an intermediate size between the bound and unbound fractions.

Example 23

Plasma samples taken from 3 patients suffering from colorectal cancer and 2 healthy volunteers were analysed for the size of associated DNA fragments using an Agilent Bioanalyzer with and without prior separation by a method of the invention. Subsequently, plasma samples taken from a further 6 patients suffering from colorectal cancer were similarly analysed.

Figure 12:
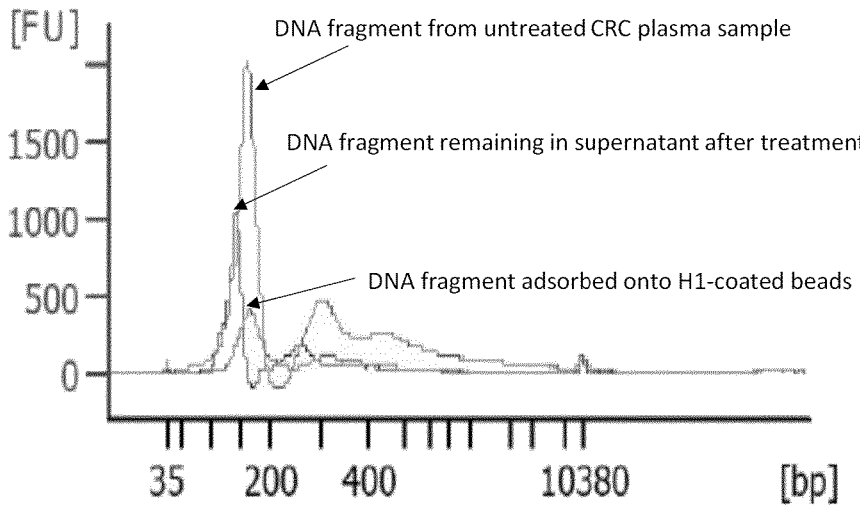
FIG. 12. Separation of mononucleosomes with or without linker DNA in plasma samples taken from three colorectal cancer patients using H1 coated magnetic beads. Bioana- lyzer results showing the base pair size profile of untreated DNA plasma samples as well as the profiles of the DNA fractions bound to H1 coated magnetic particles, or remain- ing in the supernatant, after treatment of 3 colorectal cancer plasma samples with H1 coated magnetic beads. The results show that the unbound nucleosomes in the supernatant gave a Bioanalyzer peak corresponding to a DNA size of approxi- mately 147 bp which is clearly separated from the peak corresponding to the longer DNA associated with the nucle- osomes bound to H1 coated magnetic beads at approxi- mately 167 bp.
Figure 12:
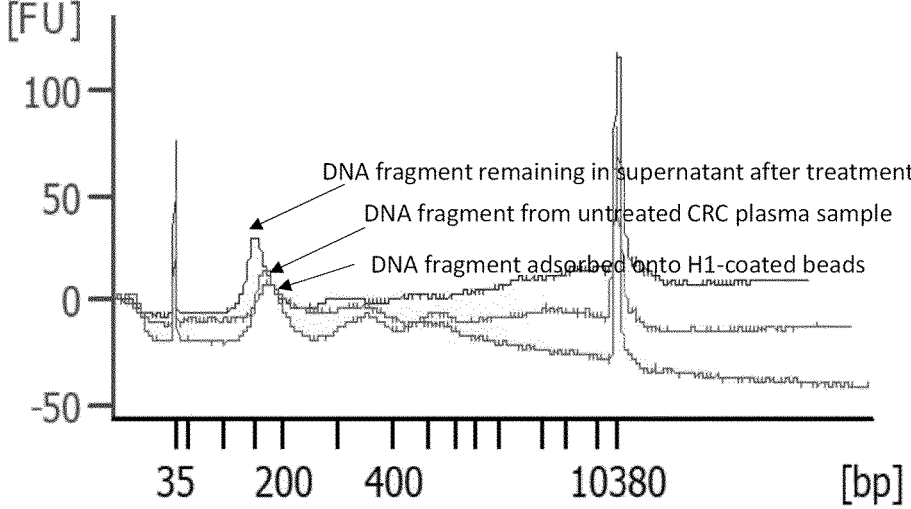
Figure 12:
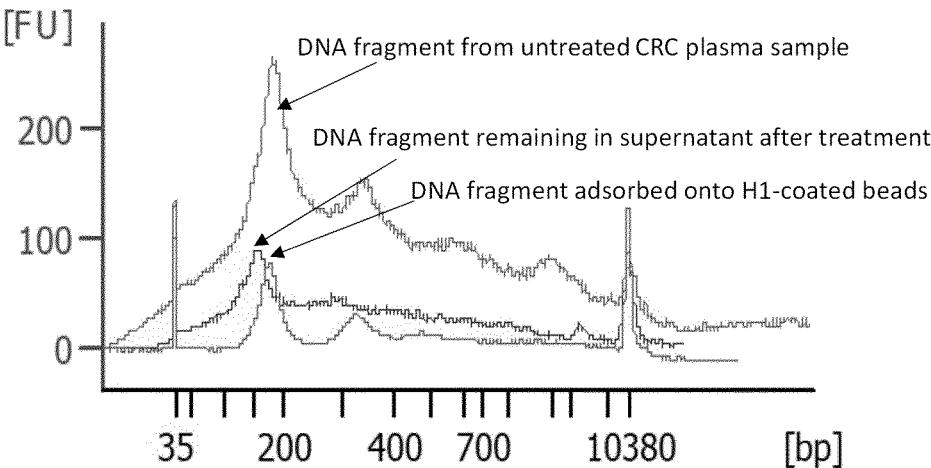
Figure 13:
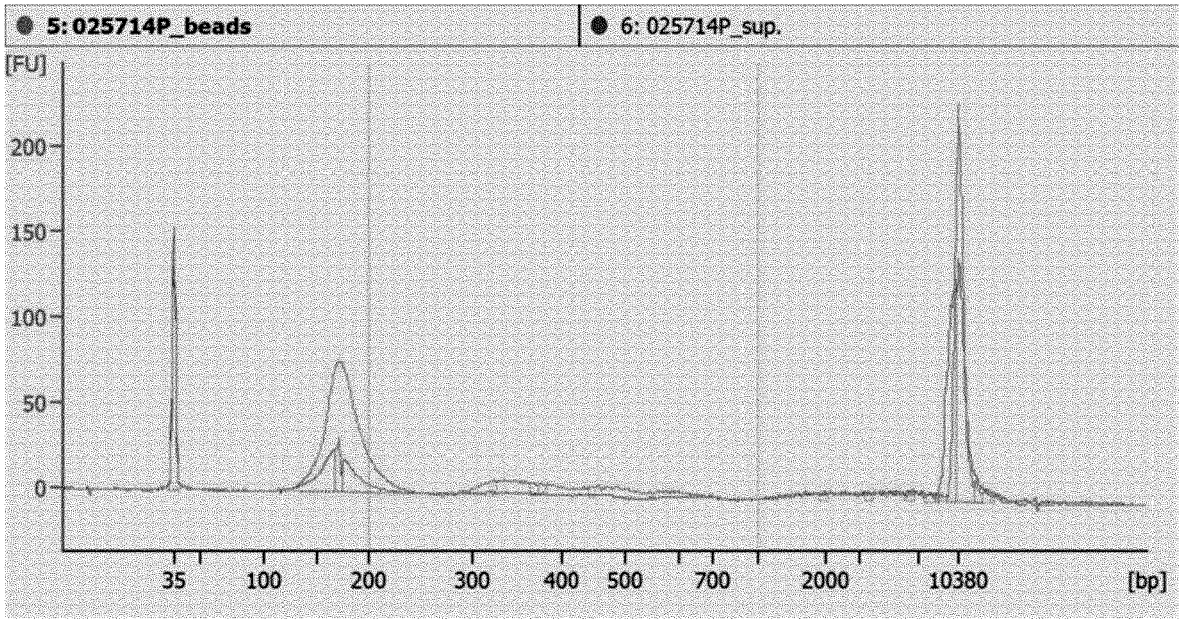
FIG. 13. Separation of mononucleosomes with or without linker DNA in plasma samples taken from three colorectal cancer patients using H1 coated magnetic beads. Bioana- lyzer results showing the base pair size profile of the DNA fractions bound to H1 coated magnetic particles, or remain- ing in the supernatant, after treatment of 3 colorectal cancer plasma samples with H1 coated magnetic beads. In all 6 cases, the results show that the unbound nucleosomes in the supernatant gave a Bioanalyzer peak corresponding to a shorter DNA size of approximately 147 bp which is clearly separated from the peak corresponding to the longer DNA associated with the nucleosomes bound to H1 coated mag- netic beads at approximately 167 bp.
Figure 13:
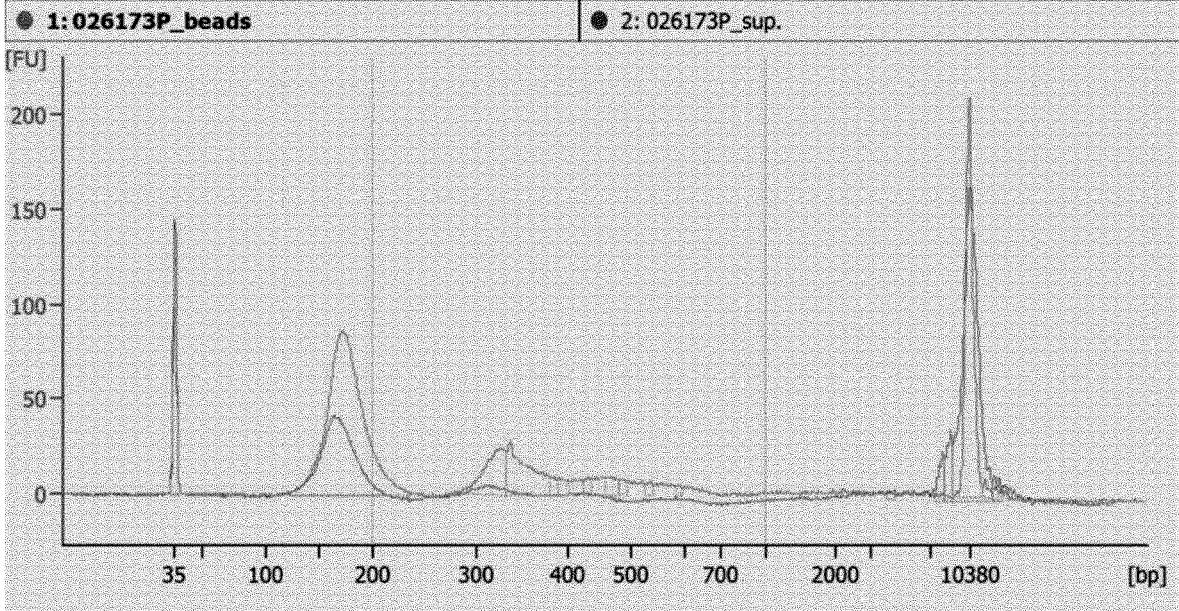
Figure 14:
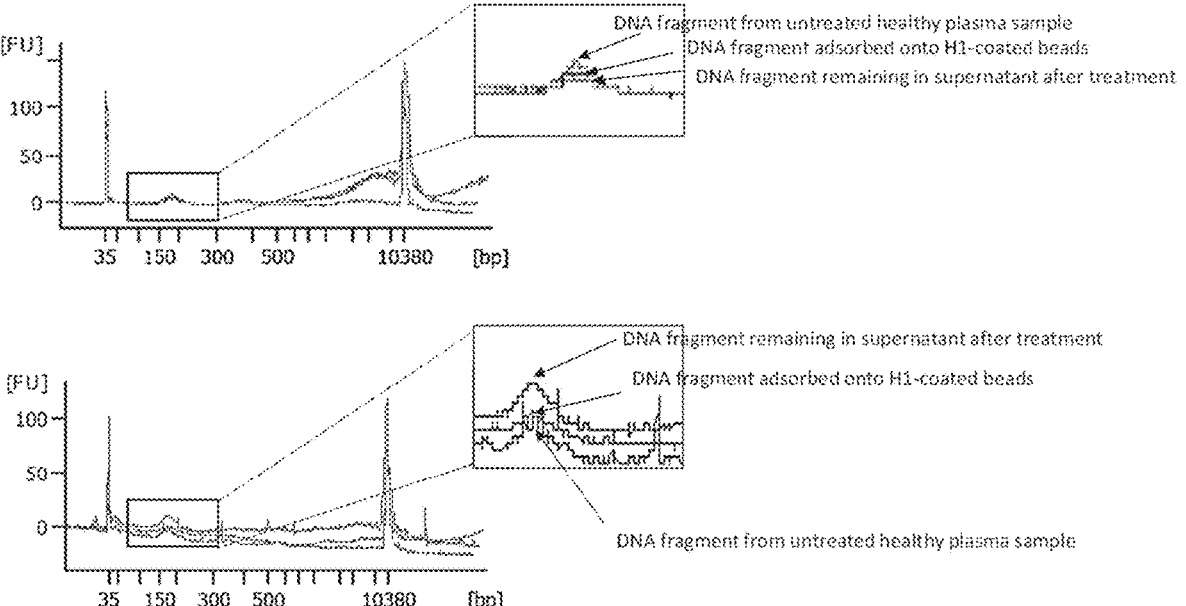
FIG. 14. Separation of mononucleosomes with or without linker DNA in plasma samples taken from two healthy volunteers using H1 coated magnetic beads. Bioanalyzer results showing the base pair size profile of the DNA fractions bound to H1 coated magnetic particles, or remain- ing in the supernatant, after treatment of 2 healthy plasma samples with H1 coated magnetic beads (magnified to illustrate the DNA fragment size distribution of interest). The results show that the untreated, bound and unbound nucleosome fractions in healthy subjects vary less with respect to the size of their associated DNA fragments than those of cancer patients.

MyOne Tosylactivated magnetic beads coated with a Histone H1.0 protein (purchased from Sigma) were exposed to the plasma samples. The beads were isolated magnetically and washed. Then, DNA was extracted from the untreated plasma samples as well as from the Histone H1.0-bound nucleosome plasma fraction isolated on the beads and from the unbound chromatin plasma fraction remaining in solution in the supernatant after treatment, using a QIAamp® Circulating Nucleic Acid kit for the isolation of free-circulating DNA fragments. The untreated, bead-bound and unbound supernatant DNA fractions were analysed for base pair length using an Agilent Bioanalyzer. The Bioanalyzer results for the first 3 cancer samples are shown in FIG. 12 and the results for the subsequent 6 cancer samples are shown in FIG. 13. The results for the healthy subjects are shown in FIG. 14. The results for 3 cancer patients are qualitatively similar to those observed for Hela nucleosomes in Example 22 and show that the unbound DNA fraction remaining in the supernatant after treatment of the sample with H1 coated magnetic beads gave a Bioanalyzer peak corresponding to a DNA size of approximately 147 bp and that this peak is well separated from the peak corresponding to the longer DNA fragments that included linker DNA associated with H1-bound nucleosomes (approximately 167 bp). The Bioanalyzer results are an analysis of fragment size profile and are not accurately quantitative. None-the-less, it is clear that the peak heights of the cancer samples differ from below 50FU to approximately 2000FU. Despite this, the separation of the peaks in the fragment size profile occurred in all cases regardless of cfDNA level present showing that the peak profile is characteristic of cancer nucleosomes regardless of their quantity. In contrast to the results for cancer patients, the results for the 2 healthy subjects show that the cfDNA levels of both subjects were low and show less difference between the 3 peaks. It is clear that the heights and relative positions of the H1-bound, unbound and untreated peaks in the cancer patients and the healthy subjects are qualitatively and quantitatively different and may individually or in combination be used as method for the detection or diagnosis of a disease. In particular the presence of a substantial amount of DNA fragments of approximately 147 bp length (associated with nucleosomes that do not contain linker DNA and hence do not bind to H1) in the supernatant after treatment with a binder of nucleosomes containing linker DNA, may be used as method for the detection or diagnosis of a disease.

Example 24

Figure 15:
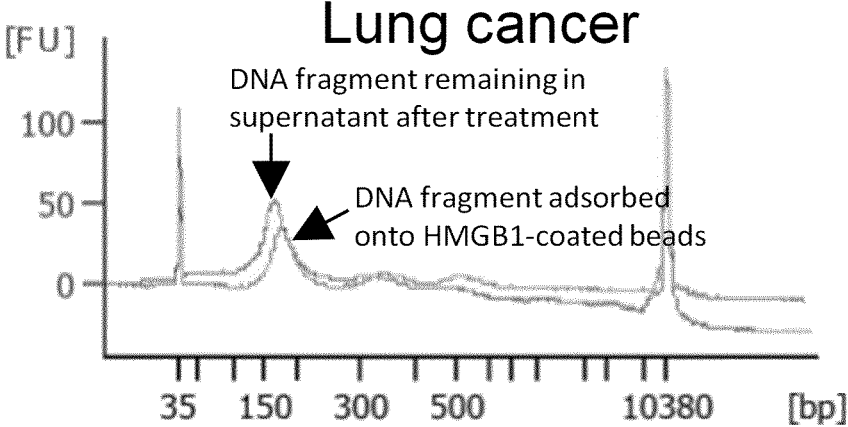
FIG. 15. Separation of mononucleosomes with or without linker DNA in plasma samples taken from three cancer patients using HMGB1 coated magnetic beads. Bioanalyzer results showing the base pair size profile of the DNA fractions bound to HMGB1 coated magnetic beads, or remaining in the supernatant, after treatment of 2 lung cancer plasma samples and 1 CRC plasma sample with HMGB1 coated magnetic beads. The results show that the unbound nucleosomes in the supernatant gave a Bioanalyzer peak corresponding to a DNA size of approximately 147 bp which is clearly separated from the peak corresponding to the longer DNA associated with the nucleosomes bound to HMGB1 coated magnetic beads at approximately 167 bp.
Figure 15:
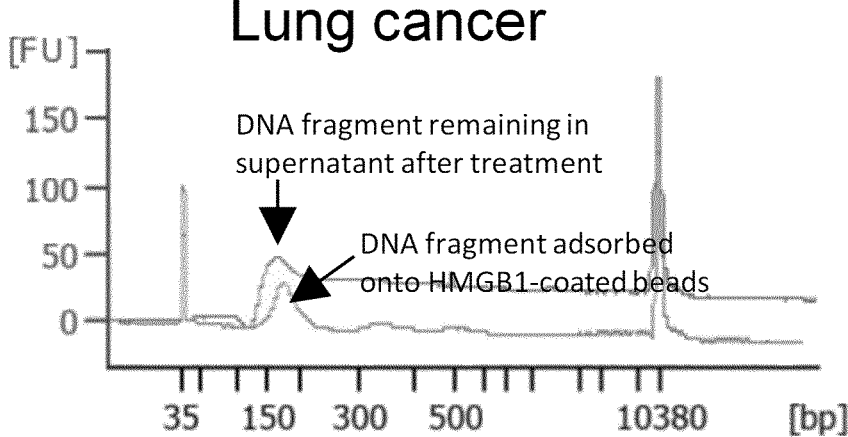
Figure 15:
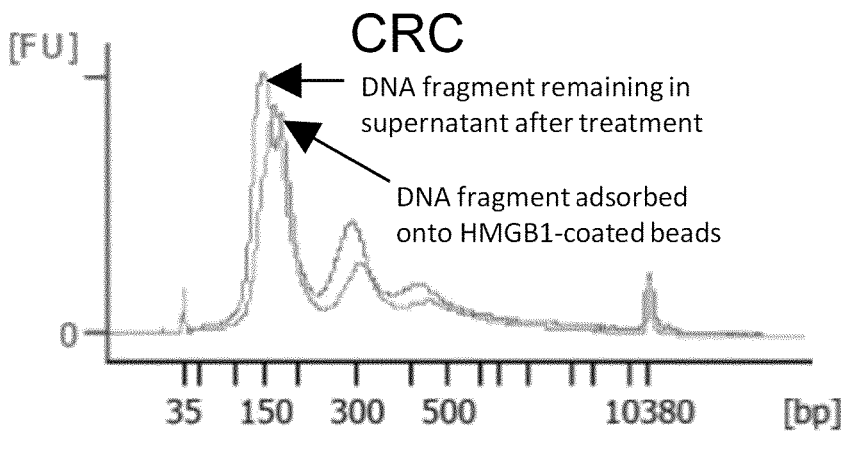

Plasma samples taken from 2 patients suffering from lung cancer and 1 patient suffering from colorectal cancer were analysed for the size of associated DNA fragments using an Agilent Bioanalyzer with and without prior separation by a method similar to that described in Example 23, but using MyOne Tosylactivated magnetic beads coated with a HMGB1 protein preparation purchased from HMGBiotech. The Bioanalyzer results for the cancer samples are shown in FIG. 15. The results for the 3 cancer patients are qualitatively similar to those observed for Hela nucleosomes in Example 22 and show that the unbound DNA fraction remaining in the supernatant after treatment of the sample with HMGB1 coated magnetic beads gave a Bioanalyzer peak corresponding to a DNA size of approximately 147 bp and that this peak is well separated from the peak corresponding to the longer DNA fragments that included linker DNA associated with HMGB1-bound nucleosomes (approximately 167 bp).

Example 25

A plasma sample taken from a patient suffering from colorectal cancer was enriched for nucleosomes containing short DNA fragments using histone H1 coated magnetic beads as described. DNA was isolated from the untreated plasma sample as well as the bead-bound and supernatant DNA fractions and single stranded libraries were prepared for Next Generation sequencing. Libraries were divided and half was subjected to Exome capture prior to sequencing (Whole Exome sequencing-WES) and the remaining went straight to sequencing (Whole Genome sequencing-WGS). Sequencing was performed on a Nova-seq from Illumina and ~300× coverage was obtained for WEC and 30× coverage for WGS. Libraries were successfully generated using commercially available kits (Swift 1S Accel and Claret Bio SRSLY). The DNA fragment size distribution found in the supernatant fraction, both pre and post library generation, was smaller than the DNA fragment size distribution of the bead-bound and untreated fractions. In addition to having smaller DNA fragments the supernatant fraction had increased frequency of known cancer mutations. For example, the mutant allele fraction of the BRAF gene was 42% in the bead-bound DNA fraction and 58% in the supernatant fraction. The mutant allele fraction of the untreated plasma was 50%.

REFERENCES

Bao et al, EMBO J., 23: 3314-3324 (2004)
Bonisch et al, Nucleic Adds Res., 40(13): 5951-5964 (2012)
Bowerman and Wereszczynski, Biophys. J., 110: 327-337 (2016)
Church et al, Gut 63: 317-325 (2014)
Conde e Silva et al, J. Mol. Biol. 370: 555-573 (2007)
Crowley et al, Nat. Rev. Clin. Oncol., 10(8): 472-484 (2013)
Dai et al, J. Vis. Exp., 50: 2593 (2011)
Dhaenens et al, Bioessays 37: 70-79 (2014)
Dhasarathy and Wade, Mutat Res., 647: 39-43 (2008)
Fong et al, Clin. Chem., 55(3): 587-589 (2009)
Guerrero-Preston et al, Epigenetics, 2(4): 223-226 (2007)
Holdenrieder et al, Int. J. Cancer (Pred. Oncol.), 95: 114-120 (2001)
Holdenrieder and Stieber, Crit. Rev. Clin. Lab. Sci., 46(1): 1-24 (2009)
Jung et al, Clin. Chimica Acta., 411: 1611-1624, (2010)
Mouliere et al, Sci Transl Med., 10: 466 (2018)
Nalabothula et al, BMC Genomics, 15:92 (2014)
Newman et al, Nat. Med., 20(5): 548-554 (2014)
Salgame et al, Nucleic Acids Res., 25(3): 680-681 (1997)
Schrader et al, PLoS ONE 10(10): e0140076 (2015)
Schwarzenbach et al, Nat. Rev. Cancer, 11(6): 426-437 (2011)
Sina et al, Nat. Comm., 9: 4915 (2018)
Snyder et al, Cell 164: 57-68 (2016)
Soares et al, Cancer, 85(1): 112-118 (1999)
Sultanov et al, AIMS Genetics, 4(1): 21-31 (2017)
Underhill et al, PLOS Genetics DOI:10.1371/journal.pgen.1006162 (2016)
van Nieuwenhuijze et al, Ann. Rheum. Dis., 62: 10-14 (2003)
Wiesler and Weinzierl, Methods Mol. Biol. 1286:97-106. Humana Press, New York, N.Y. (2015)

Yang et al, Int. J. Oncol., 52(4): 1235-1245 (2018)
Yi and Kim, BMB Reports, 51(5): 211-218 (2018)
Zhou et al, Semin. Oncol., 39(4): 440-448 (2012)

The invention claimed is:

1. A method for separating circulating cell free nucleosomes comprising linker DNA from a biological fluid sample, wherein said method comprises the steps of:
   (i) contacting the sample with a binding agent which binds to-nucleosome associated linker DNA and
   (ii) isolating nucleosomes from the sample which are bound to the binding agent in step (i),
   wherein the binding agent which binds to nucleosome associated linker DNA is selected from: histone H1, a binding fragment of histone H1, an engineered analogue of histone H1, a chromatin binding protein, a binding fragment of a chromatin binding protein, and an engineered analogue of a chromatin binding protein.

2. A method for separating circulating cell free nucleosomes which do not comprise linker DNA from a biological fluid sample, wherein said method comprises the steps of:
   (i) contacting the sample with a binding agent which binds to nucleosome associated linker DNA and
   (ii) isolating nucleosomes from the sample which are not bound to the binding agent in step (i),
   wherein the binding agent which binds to nucleosome associated linker DNA is selected from: histone H1, a binding fragment of histone H1, an engineered analogue of histone H1, a chromatin binding protein, a binding fragment of a chromatin binding protein, and an engineered analogue of a chromatin binding protein.

3. The method as defined in claim 1, wherein the binding agent which binds to nucleosome associated linker DNA is histone H1.

4. The method as defined in claim 1, wherein the binding agent which binds to nucleosome associated linker DNA is a chromatin binding protein.

5. The method as defined in claim 4, wherein the chromatin binding protein which binds to linker DNA is selected from:
   (a) a Chromodomain Helicase DNA Binding (CHD) protein;
   (b) a DNA (cytosine-5)-methyltransferase (DNMT) protein;
   (c) a High mobility group box protein (HMGB) protein;
   (d) a Poly [ADP-ribose] polymerase (PARP) protein; or
   (e) a Methyl-CpG-binding domain (MBD) protein.

6. The method as defined in claim 1, which additionally comprises:
   (iii) analysing the isolated cell free nucleosomes of step (ii) by immunoassay, mass spectroscopy and/or DNA analysis.

7. The method as defined in claim 6, wherein step (iii) comprises analysing the isolated cell free nucleosome for epigenetic nucleosome features that are selected from: histone type, post-translational modifications, histone isoforms, particular nucleotides or modified nucleotides, proteins adducted to the nucleosome or combinations thereof.

8. The method as defined in claim 6, wherein the DNA analysis comprises targeted Next Generation Sequencing, whole genome Next Generation Sequencing, methylated DNA sequencing analysis, BEAMing, PCR, digital PCR, cold PCR, isothermal amplification, MIDI-Activated Pyrophosphorolysis (MAP) or Personalized Analysis of Rearranged Ends (PARE).

9. The method as defined in claim 1, which additionally comprises contacting the sample bound in step (i) with a second binding agent which binds to nucleosomes or a component thereof.

10. The method as defined in claim 1, wherein the biological fluid sample is selected from a blood, serum or plasma sample.

11. The method as defined in claim 1, wherein the sample is contacted with more than one type of binding agent which binds to nucleosomes comprising linker DNA.

12. A method for isolating purified circulating tumour DNA (ctDNA) from a biological fluid sample, wherein said method comprises the steps of:

(i) performing the method as defined in claim 2; and (ii) extracting the DNA from the isolated nucleosomes.

\* \* \* \* \*